United States Patent
Kim et al.

(10) Patent No.: US 11,398,603 B2
(45) Date of Patent: *Jul. 26, 2022

(54) HETEROCYCLIC COMPOUND AND ORGANIC ELECTRONIC DEVICE COMPRISING SAME

(71) Applicant: LG CHEM, LTD., Seoul (KR)

(72) Inventors: Ji Hoon Kim, Daejeon (KR); Jiyoung Lee, Daejeon (KR); Songrim Jang, Daejeon (KR); Doowhan Choi, Daejeon (KR); Bogyu Lim, Daejeon (KR); Junghyun Park, Daejeon (KR)

(73) Assignee: LG CHEM, LTD.

( * ) Notice: Subject to any disclaimer, the term of this patent is extended or adjusted under 35 U.S.C. 154(b) by 0 days.

This patent is subject to a terminal disclaimer.

(21) Appl. No.: 16/470,759

(22) PCT Filed: Oct. 22, 2018

(86) PCT No.: PCT/KR2018/012476
§ 371 (c)(1),
(2) Date: Jun. 18, 2019

(87) PCT Pub. No.: WO2019/083235
PCT Pub. Date: May 2, 2019

(65) Prior Publication Data
US 2020/0251661 A1    Aug. 6, 2020

(30) Foreign Application Priority Data

Oct. 23, 2017 (KR) .................. 10-2017-0137489
Mar. 8, 2018 (KR) .................. 10-2018-0027346

(51) Int. Cl.
*H01L 51/00* (2006.01)
*C07D 495/22* (2006.01)
*H01L 51/42* (2006.01)

(52) U.S. Cl.
CPC ........ *H01L 51/0068* (2013.01); *C07D 495/22* (2013.01); *H01L 51/0074* (2013.01); *H01L 51/4253* (2013.01)

(58) Field of Classification Search
CPC ............ H01L 51/42–448; H01L 51/005–0074
See application file for complete search history.

(56) References Cited

U.S. PATENT DOCUMENTS

| | | | | |
|---|---|---|---|---|
| 11,008,343 B2 * | 5/2021 | Kim | .............. | H01L 51/0074 |
| 2018/0273760 A1 | 9/2018 | Rosselli et al. | | |
| 2019/0284210 A1 * | 9/2019 | Kim | .............. | C07D 495/04 |

FOREIGN PATENT DOCUMENTS

| | | |
|---|---|---|
| CN | 106467547 | 3/2017 |
| CN | 107011361 | 8/2017 |
| JP | 2010138077 | 6/2010 |

(Continued)

OTHER PUBLICATIONS

Zhang, et al. "Synergistic effect of fluorination on molecular energy level modulation in highly efficient photovoltaic polymers." Advanced Materials 26.7 (2014): 1118-1123.*

(Continued)

*Primary Examiner* — William E McClain
(74) *Attorney, Agent, or Firm* — Myers Bigel, P.A.

(57) ABSTRACT

The present specification relates to a heterocyclic compound represented by Formula 1 and an organic electronic device comprising the same.

14 Claims, 7 Drawing Sheets

(56) References Cited

FOREIGN PATENT DOCUMENTS

| JP | 6635530 | 1/2020 | | |
|---|---|---|---|---|
| KR | 101702306 | 2/2017 | | |
| KR | 20170026190 | 3/2017 | | |
| WO | WO-2018032945 A1 | * | 2/2018 | ............ C07D 495/04 |

OTHER PUBLICATIONS

Min, et al. "Fully Solution-Processed Small Molecule Semitransparent Solar Cells: Optimization of Transparent Cathode Architecture and Four Absorbing Layers." Advanced Functional Materials 26.25 (2016): 4543-4550.*
Ji, et al. "Synergistic effect of halogenation on molecular energy level and photovoltaic performance modulations of highly efficient small molecular materials." Nano Energy 40 (2017): 214-223.*
Machine Translation of CN-107011361-A.*
Machine Translation of WO-2018032945-A1.*
Cheng, et al. "Toward high open-circuit voltage by smart chain engineering in 2D-conjugated polymer for polymer solar cells." Solar Energy Materials and Solar Cells 149 (2016): 162-169.*
Cui, et al. "Improvement of open-circuit voltage and photovoltaic properties of2D-conjugated polymers by alkylthio substitution." Energy & Environmental Science 7.7 (2014): 2276-2284.*
Kan, et al. "Small-molecule acceptor based on the heptacyclic benzodi (cyclopentadithiophene) unit for highly efficient nonfullerene organic solar cells." Journal of the American Chemical Society 139.13 (2017): 4929-4934.*
Wang, et al. "Rational design and characterization of high-efficiency planar A-π-D-π-A type electron donors in small molecule organic solar cells: A quantum chemical approach." Materials Chemistry and Physics 145.3 (2014): 387-396.*
Wang, et al. "Effect of isomerization on high-performance nonfullerene electron acceptors." Journal of the American Chemical Society 140.29 (2018): 9140-9147.*
English translation of the International Search Report corresponding to International Patent Application No. PCT/KR2018/012476 (2 pages) (dated Jan. 31, 2019).
Wang et al. "Enhancing Performance of Nonfullerene Acceptors via Side-Chain Conjugation Strategy" Advanced Materials, 29:1702125 (2017).
English translation of First Office Action corresponding to Japanese Patent Application No. 2019-538215 (7 pages) (dated Jun. 8, 2020).
Yao et al. "Achieving Highly Efficient Nonfullerene Organic Solar Cells with Improved Intermolecular Interaction and Open-Circuit Voltage" Advanced Materials, 29(21):1700254, pp. 1-8 (2017).

* cited by examiner

HETEROCYCLIC COMPOUND AND ORGANIC ELECTRONIC DEVICE COMPRISING SAME

CROSS REFERENCE TO RELATED APPLICATIONS

This application is a 35 U.S.C. § 371 national stage application of PCT International Application No. PCT/KR2018/012476, filed Oct. 22, 2018, which claims priority from Korean Patent Application No. 10-2018-0027346, filed Mar. 8, 2018, and Korean Patent Application No. 10-2017-0137489, filed Oct. 23, 2017, the contents of which are incorporated herein in their entireties by reference. The above-referenced PCT International Application was published in the Korean language as International Publication No. WO 2019/083235 A1 on May 2, 2019.

TECHNICAL FIELD

The present specification relates to a heterocyclic compound and an organic electronic device comprising the same.

BACKGROUND ART

An organic electronic device means a device that requires an exchange of electric charges between electrodes using holes and/or electrons and organic materials. The organic electronic device may be largely divided into the following two categories depending on the operation principle. First, the organic electronic device is an electronic device in which an exciton is formed in an organic material layer by a photon that flows from an external light source to the device, the exciton is separated into electrons and holes, and the electrons and the holes are each transferred to the different electrodes and used as a current source (voltage source). Second, the organic electronic device is an electronic device in which holes and/or electrons are injected into an organic material semiconductor, which forms an interface with two or more electrodes, by applying a voltage or an electric current to the electrodes, and the device is operated by the injected electrons and holes.

Examples of an organic electronic device comprise an organic solar cell, an organic photoelectric device, an organic light emitting device, an organic transistor, and the like, and hereinafter, the organic solar cell will be mainly described in detail, but in the organic electronic devices, a hole injection or transport material, an electron injection or transport material, or a light emitting material is operated under similar principles.

For the organic solar cell, it is important to increase efficiency so as to output as much electric energy as possible from solar energy. In order to increase the efficiency of the organic solar cell, it is important to generate as many excitons as possible inside a semiconductor, but it is also important to pull the generated charges to the outside without loss. One of the reasons for the charge loss is the dissipation of generated electrons and holes due to recombination. Various methods have been proposed to deliver generated electrons and holes to an electrode without loss, but additional processes are required in most cases, and accordingly, manufacturing costs may be increased.

REFERENCES OF THE RELATED ART

Patent Document (Patent Document 1) U.S. Pat. No. 5,331,183
(Patent Document 2) U.S. Pat. No. 5,454,880

DETAILED DESCRIPTION OF THE INVENTION

Technical Problem

The present specification provides a heterocyclic compound and an organic electronic device comprising the same.

Technical Solution

The present specification provides a heterocyclic compound represented by the following Formula 1.

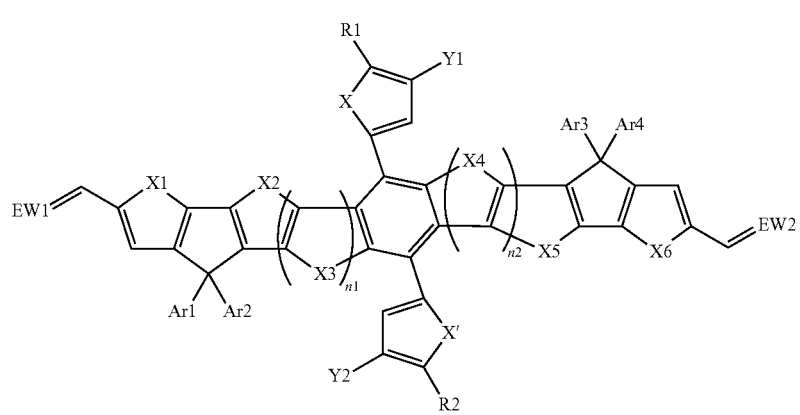

[Formula 1]

In Formula 1,

X, X' and X1 to X6 are the same as or different from each other, and are each independently O, S, or Se, R1 and R2 are the same as or different from each other, and are each independently a substituted or unsubstituted straight-chained or branched alkyl group; a substituted or unsubstituted straight-chained or branched alkoxy group; or a substituted or unsubstituted straight-chained or branched thioalkoxy group, Y1 and Y2 are the same as or different from each other, and are each independently hydrogen; a halogen group; a substituted or unsubstituted straight-chained or branched alkyl group; or a substituted or unsubstituted straight-chained or branched alkoxy group, EW1 and EW2 are the same as or different from each other, and are each independently a group which serves as an electron acceptor, Ar1 to Ar4 are the same as or different from each other, and are each independently a substituted or unsubstituted aryl group; or a substituted or unsubstituted heteroaryl group, n1 and n2 are each 0 or 1, and when n1 and n2 are 0, and R1 and R2 are the same as or different from each other, and are each independently a substituted or unsubstituted straight-chained or branched alkyl group, Y1 and Y2 are the same as or different from each other, and are each independently a halogen group; a substituted or unsubstituted straight-chained or branched alkyl group; or a substituted or unsubstituted straight-chained or branched alkoxy group.

The present specification provides a composition for an organic electronic device, comprising the above-described heterocyclic compound.

Further, the present specification provides an organic electronic device comprising: a first electrode; a second electrode provided to face the first electrode; and an organic material layer having one or more layers provided between the first electrode and the second electrode, in which one or more layers of the organic material layer comprise the above-described composition for an organic electronic device.

Advantageous Effects

An organic solar cell comprising the heterocyclic compound represented by Formula 1 according to an exemplary embodiment of the present specification has excellent photoelectric conversion efficiency.

BEST MODE

Figure 1:
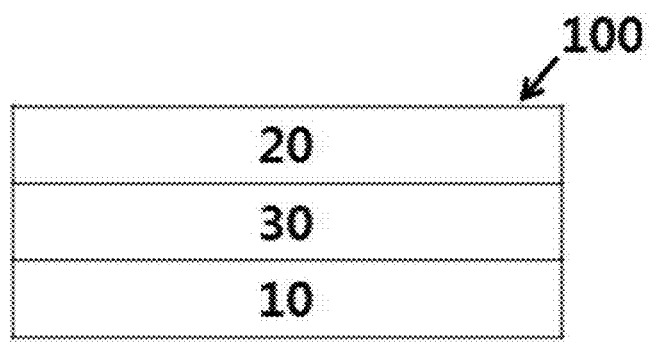
FIG. 1 is a view illustrating an organic electronic device according to an exemplary embodiment of the present specification.

Hereinafter, the present specification will be described in detail.

The present specification provides the heterocyclic compound represented by Formula 1.

The heterocyclic compound represented by Formula 1 according to an exemplary embodiment of the present specification absorbs light within a wide wavelength range by introducing an alkyl group, an alkoxy group, a thioalkoxy group (S-Alkyl group) and/or fluorine as a substituent and has high LUMO energy, so that an open-circuit voltage loss is low, and as a result, the heterocyclic compound has a high open-circuit voltage ($V_{oc}$) and excellent photoelectric conversion efficiency when the heterocyclic compound is used as an n-type organic material layer (electron acceptor material) of a photoactive layer of an organic solar cell.

In the heterocyclic compound represented by Formula 1 according to an exemplary embodiment of the present specification, when R1 and R2 are an alkyl group, Y1 and Y2 comprise a substituent other than hydrogen, particularly, fluorine, so that the heterocyclic compound absorbs light in a long wavelength region. Accordingly, an organic solar cell comprising the compound exhibits a higher short-circuit current than that of an organic solar cell comprising a compound of Formula 1 in which R1 and R2 are an alkyl group, and Y1 and Y2 are hydrogen.

When one part "includes" one constituent element in the present specification, unless otherwise specifically described, this does not mean that another constituent element is excluded, but means that another constituent element may be further included.

When one member is disposed "on" another member in the present specification, this comprises not only a case where the one member is brought into contact with another member, but also a case where still another member is present between the two members.

Examples of the substituents will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or more substituents selected from the group consisting of deuterium; a halogen group; an alkyl group; an alkenyl group; an alkoxy group; a thioalkoxy group; an ester group; a carbonyl group; a carboxyl group; a hydroxyl group; a cycloalkyl group; a silyl group; an arylalkenyl group; an aryloxy group;

an alkylthioxy group; an alkylsulfoxy group; an arylsulfoxy group; a boron group; an alkylamine group; an aralkylamine group; an arylamine group; a heterocyclic group; an arylamine group; an aryl group; a nitrile group; a nitro group; a hydroxyl group; and a heteroaryl group comprising one or more of N, O, and S atoms, or having no substituent.

The substituents may be unsubstituted or substituted with an additional substituent.

In the present specification, a halogen group may be fluorine, chlorine, bromine or iodine.

In the present specification, the number of carbon atoms of an imide group is not particularly limited, but is preferably 1 to 25. Specifically, the imide group may be a compound having the following structures, but is not limited thereto.

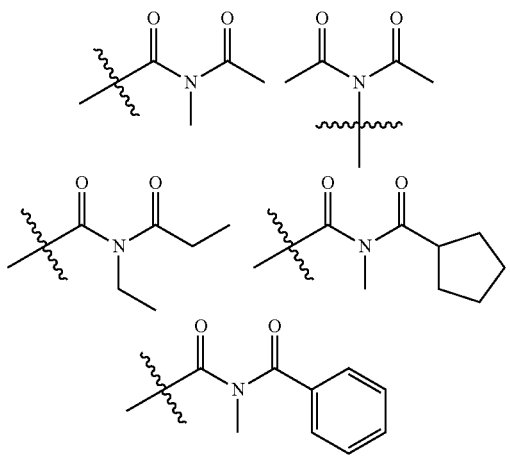

In the present specification, for the amide group, one or two nitrogen atoms of the amide group may be substituted with hydrogen, a straight-chained, branched, or cyclic alkyl group having 1 to 25 carbon atoms, or an aryl group having 6 to 25 carbon atoms. Specifically, the amide group may be a compound having the following structural formulae, but is not limited thereto.

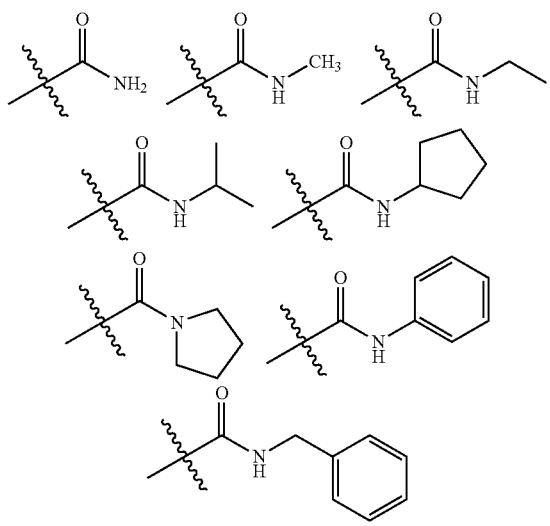

In the present specification, the alkyl group may be straight-chained or branched, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be straight-chained, branched, or cyclic. The number of carbon atoms of the alkoxy group is not particularly limited, but is preferably 1 to 20. Specific examples thereof include methoxy, ethoxy, n-propoxy, isopropoxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the description on the alkoxy group may be applied to the thioalkoxy group, except that O of the alkoxy group is S.

In the present specification, the alkenyl group may be straight-chained or branched, and the number of carbon atoms thereof is not particularly limited, but is preferably 2 to 40. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be —BR$_a$R$_b$, and R$_a$ and R$_b$ are the same as or different from each other, and may be each independently selected from the group consisting of hydrogen; deuterium; a halogen group; a nitrile group; a substituted or unsubstituted monocyclic or polycyclic cycloalkyl group having 3 to 30 carbon atoms; a substituted or unsubstituted straight-chained or branch-chained alkyl group having 1 to 30 carbon atoms; a substituted or unsubstituted monocyclic or polycyclic aryl group having 6 to 30 carbon atoms; and a substituted or unsubstituted monocyclic or polycyclic heteroaryl group having 2 to 30 carbon atoms.

In the present specification, specific examples of a phosphine oxide group include a diphenylphosphine oxide group, a dinaphthylphosphine oxide group, and the like, but are not limited thereto.

In the present specification, an aryl group may be a monocyclic aryl group or a polycyclic aryl group, and includes the case where an alkyl group having 1 to 25 carbon atoms or an alkoxy group having 1 to 25 carbon atoms is substituted. Further, the aryl group in the present specification may mean an aromatic ring.

When the aryl group is a monocyclic aryl group, the number of carbon atoms thereof is not particularly limited, but is preferably 6 to 25. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 24. Specific examples of the polycyclic aryl group include a naphthyl group, an anthracenyl group, a phenanthryl group, a pyrenyl group, a perylenyl group, a chrysenyl group, a fluorenyl group, and the like, but are not limited thereto.

In the present specification, a fluorenyl group has a structure in which two cyclic organic compounds are linked to each other through one atom.

In the present specification, the fluorenyl group may be substituted, and adjacent substituents may be bonded to each other to form a ring.

When the fluorenyl group is substituted, the substituent may be

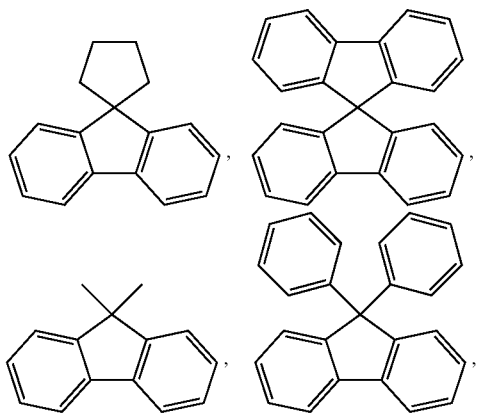

and the like. However, the fluorenyl group is not limited thereto.

In the present specification, a heteroaryl group is a heteroaryl group including one or more of O, N, and S as a hetero element, and the number of carbon atoms thereof is not particularly limited, but is preferably 2 to 60. Examples of the heteroaryl group include a selenophene group, a thiophene group, a furan group, a pyrrole group, an imidazole group, a thiazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, an isoxazolyl group, a thiadiazolyl group, a benzothiadiazolyl group, a phenothiazinyl group, a thienothiophene group, a dibenzofuranyl group, and the like, but are not limited thereto.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, a hetero ring includes one or more atoms other than carbon, that is, one or more heteroatoms, and specifically, the heteroatom may include one or more atoms selected from the group consisting of O, N, Se, S, and the like. The hetero ring may be monocyclic or polycyclic, may be an aromatic ring, an aliphatic ring, or a fused ring of the aromatic ring and the aliphatic ring, and may be selected from the examples of the heteroaryl group or the heterocyclic group, except for the hetero ring which is not monovalent.

In the present specification, a group (EDG: electron donative group) serving as an electron donor or an electron donor material generally means a substituent or material which has a negative charge or an unshared electron pair, and donates electrons to a portion which lacks a positive charge or an electron pair. Additionally, in the present specification, a group (EDG: electron donative group) serving as an electron donor or an electron donor material comprises a substituent capable of transferring an excited electron to an electron acceptor having large electronegativity due to excellent electron-retention properties of the molecule itself when accepting light in a mixed stated with an electron acceptor even though the group (EDG: electron donative group) or the electron donor material does not have a negative charge or an unshared electron pair.

In the present specification, a group (EWG: electron withdrawing group) serving as an electron acceptor or an electron acceptor material collectively means a substituent or material accepting electrons from an electron donative group.

According to an exemplary embodiment of the present specification, in Formula 1, n1 is 0.

According to an exemplary embodiment of the present specification, in Formula 1, n1 is 1.

According to an exemplary embodiment of the present specification, in Formula 1, n2 is 0.

According to an exemplary embodiment of the present specification, in Formula 1, n2 is 1.

According to an exemplary embodiment of the present specification, in Formula 1, X is O.

According to an exemplary embodiment of the present specification, in Formula 1, X is S.

According to an exemplary embodiment of the present specification, in Formula 1, X is Se.

According to an exemplary embodiment of the present specification, in Formula 1, X' is O.

According to an exemplary embodiment of the present specification, in Formula 1, X' is S.

According to an exemplary embodiment of the present specification, in Formula 1, X' is Se.

According to an exemplary embodiment of the present specification, in Formula 1, X1 is O.

According to an exemplary embodiment of the present specification, in Formula 1, X1 is S.

According to an exemplary embodiment of the present specification, in Formula 1, X1 is Se.

According to an exemplary embodiment of the present specification, in Formula 1, X2 is O.

According to an exemplary embodiment of the present specification, in Formula 1, X2 is S.

According to an exemplary embodiment of the present specification, in Formula 1, X2 is Se.

According to an exemplary embodiment of the present specification, in Formula 1, X3 is O.

According to an exemplary embodiment of the present specification, in Formula 1, X6 is O.

According to an exemplary embodiment of the present specification, in Formula 1, X6 is S.

According to an exemplary embodiment of the present specification, in Formula 1, X6 is Se.

According to an exemplary embodiment of the present specification, Formula 1 is represented by the following Formula 1-1 or 1-2.

[Formula 1-1]

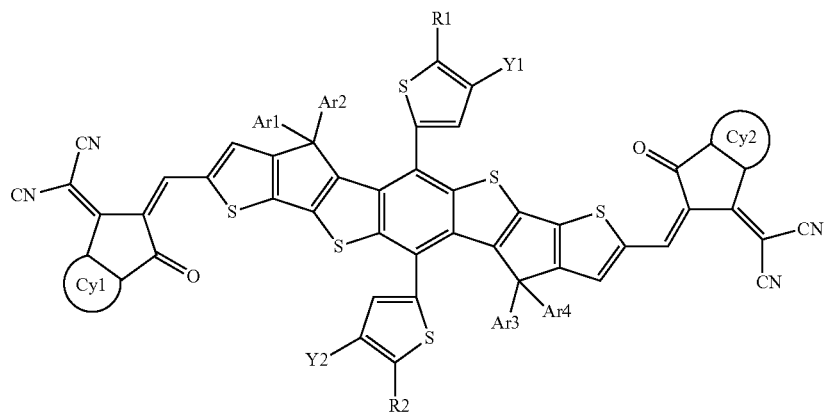

[Formula 1-2]

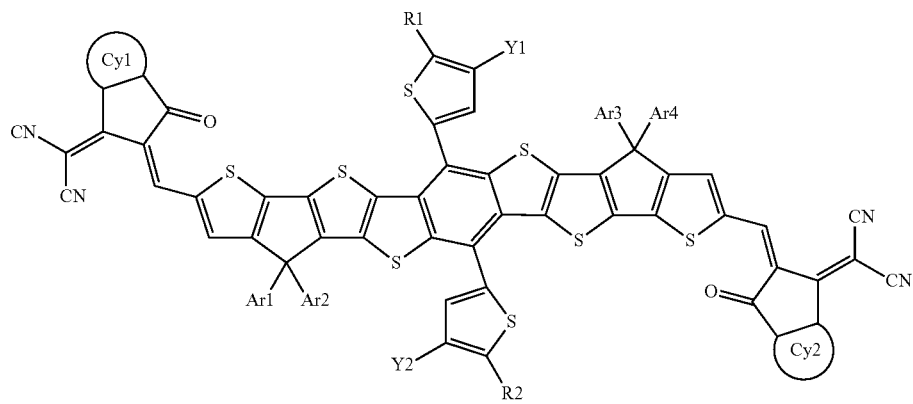

According to an exemplary embodiment of the present specification, in Formula 1, X3 is S.

According to an exemplary embodiment of the present specification, in Formula 1, X3 is Se.

According to an exemplary embodiment of the present specification, in Formula 1, X4 is O.

According to an exemplary embodiment of the present specification, in Formula 1, X4 is S.

According to an exemplary embodiment of the present specification, in Formula 1, X4 is Se.

According to an exemplary embodiment of the present specification, in Formula 1, X5 is O.

According to an exemplary embodiment of the present specification, in Formula 1, X5 is S.

According to an exemplary embodiment of the present specification, in Formula 1, X5 is Se.

In Formulae 1-1 and 1-2, the definitions of R1, R2, Y1, Y2, and Ar1 to Ar4 are the same as those defined in Formula 1, and Cy1 and Cy2 are the same as or different from each other, and are each independently an aromatic hydrocarbon ring unsubstituted or substituted with a halogen group, a straight-chained or branched alkyl group, or a straight-chained or branched alkoxy group; or a hetero ring unsubstituted or substituted with a halogen group, a straight-chained or branched alkyl group, or a straight-chained or branched alkoxy group.

According to an exemplary embodiment of the present specification, Formula 1 is represented by any one of the following Formulae 1-3 to 1-5.

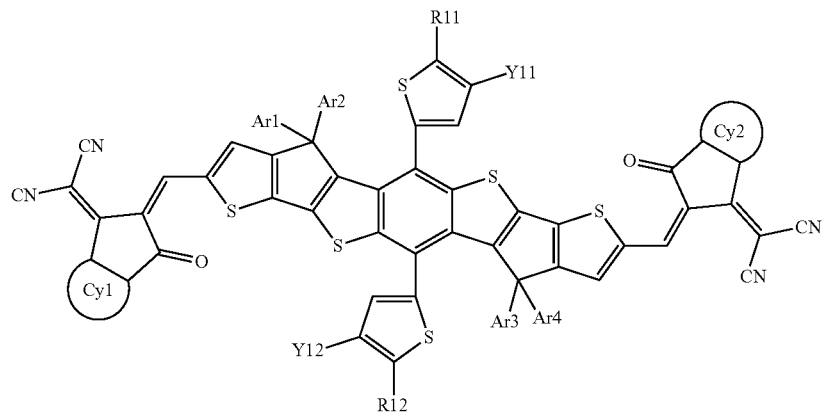

[Formula 1-3]

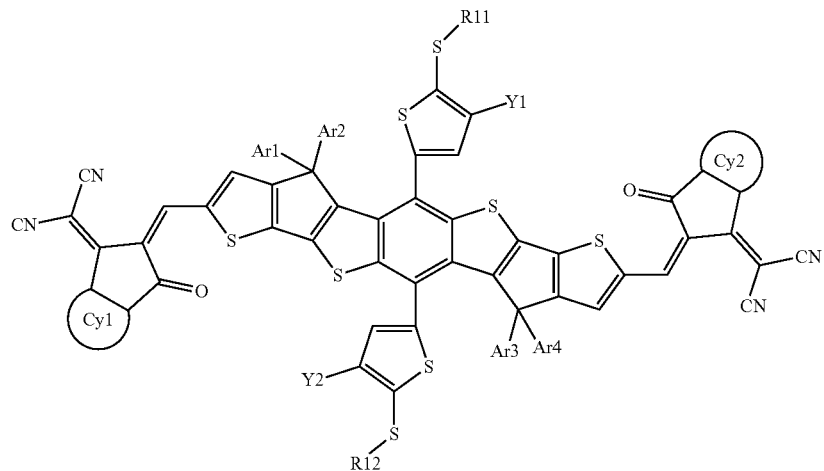

[Formula 1-4]

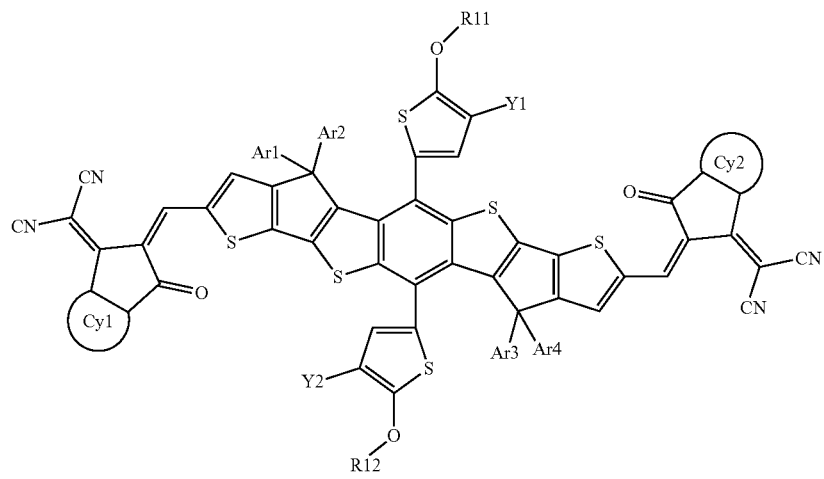

[Formula 1-5]

In formulae 1-3 to 1-5, the definitions of Y1, Y2, and Ar1 to Ar4 are the same as those defined in Formula 1, R11 and R12 are the same as or different from each other, and are each independently a substituted or unsubstituted straight-chained or branched alkyl group, Y11 and Y12 are the same as or different from each other, and are each independently a halogen group, and Cy1 and Cy2 are the same as or different from each other, and are each independently an aromatic hydrocarbon ring unsubstituted or substituted with a halogen group, a straight-chained or branched alkyl group, or a straight-chained or branched alkoxy group; or a hetero ring unsubstituted or substituted with a halogen group, a straight-chained or branched alkyl group, or a straight-chained or branched alkoxy group.

According to another exemplary embodiment of the present specification, R11 and R12 are the same as or different from each other, and are each independently a straight-chained or branched alkyl group.

According to still another exemplary embodiment of the present specification, R11 and R12 are the same as or different from each other, and are each independently a branched alkyl group.

According to yet another exemplary embodiment of the present specification, R11 and R12 are the same as or different from each other, and are each independently a branched alkyl group having 3 to 20 carbon atoms.

According to still yet another exemplary embodiment of the present specification, R11 and R12 are the same as or different from each other, and are each independently a branched alkyl group having 3 to 10 carbon atoms.

According to a further exemplary embodiment of the present specification, R11 and R12 are the same as or different from each other, and are each independently a 2-ethylhexyl group.

According to another further exemplary embodiment of the present specification, Y11 and Y12 are fluorine.

According to an exemplary embodiment of the present specification, Formula 1 is represented by any one of the following Formulae 2-1 to 2-6.

[Formula 2-1]

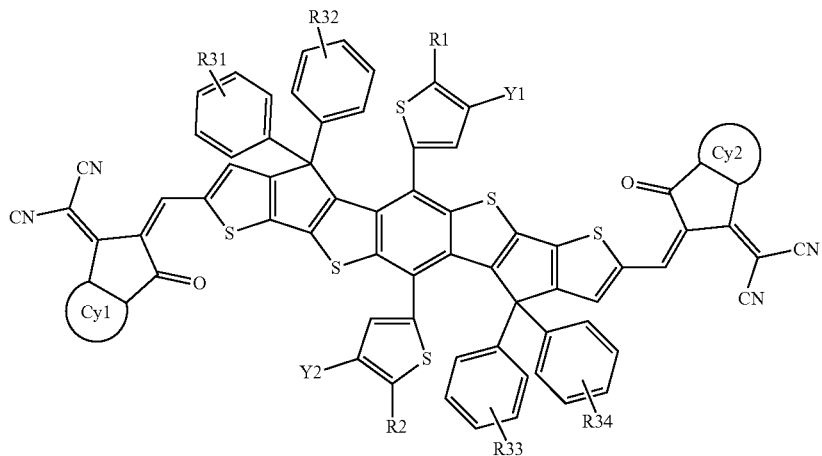

[Formula 2-2]

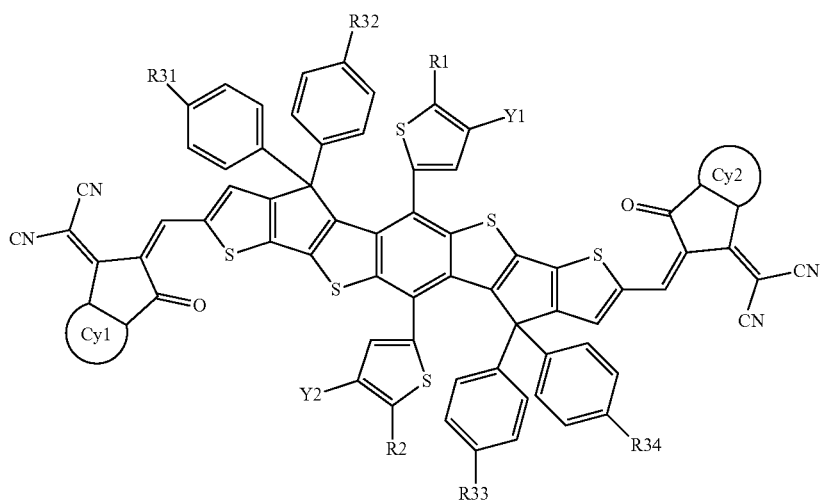

-continued
[Formula 2-3]
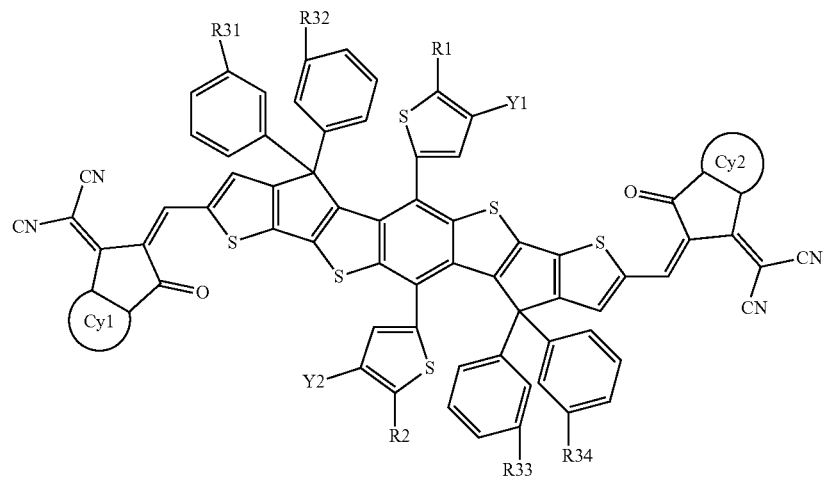
[Formula 2-4]
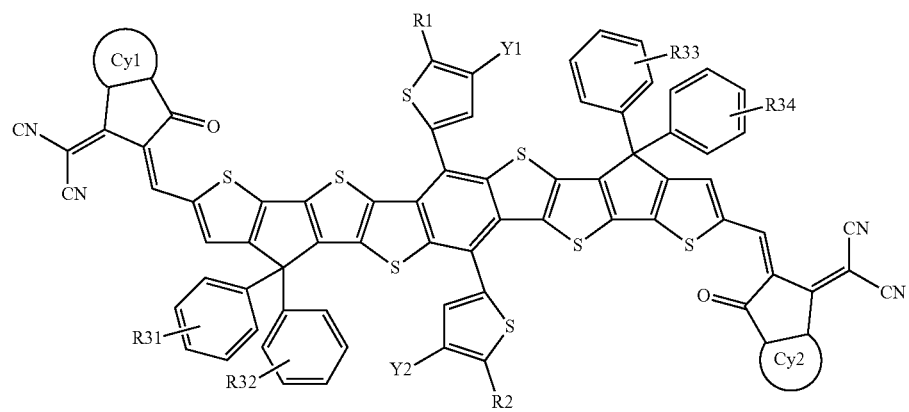
[Formula 2-5]
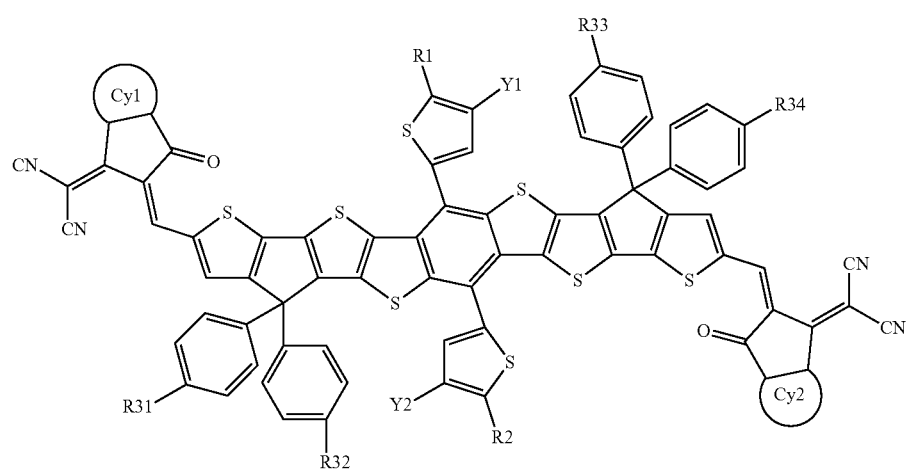

[Formula 2-6]

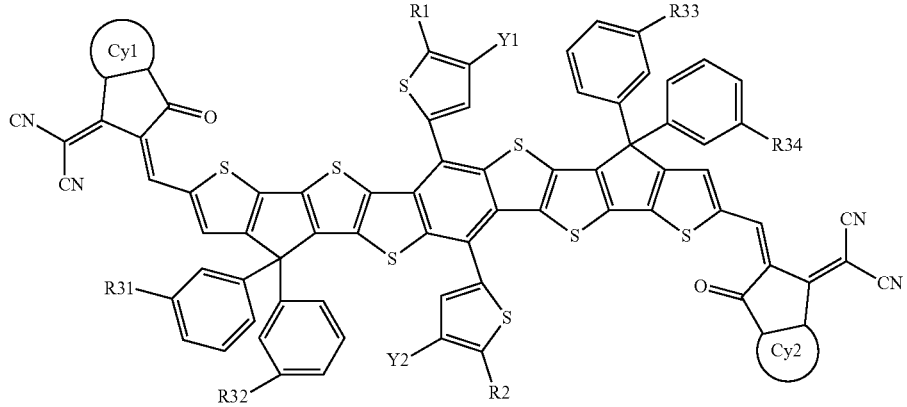

In Formulae 2-1 to 2-6, the definitions of R1, R2, Y1, and Y2 are the same as those defined in Formula 1, R31 to R34 are the same as or different from each other, and are each independently a straight-chained or branched alkyl group; a straight-chained or branched alkoxy group; or a straight-chained or branched thioalkoxy group, and Cy1 and Cy2 are the same as or different from each other, and are each independently an aromatic hydrocarbon ring unsubstituted or substituted with a halogen group, a straight-chained or branched alkyl group, or a straight-chained or branched alkoxy group; or a hetero ring unsubstituted or substituted with a halogen group, a straight-chained or branched alkyl group, or a straight-chained or branched alkoxy group.

According to an exemplary embodiment of the present specification, in Formulae 2-1 to 2-6, R31 to R34 are the same as or different from each other, and are each independently a straight-chained or branched alkyl group; a straight-chained or branched alkoxy group; or a straight-chained or branched thioalkoxy group.

According to an exemplary embodiment of the present specification, in Formulae 2-1 to 2-6, R31 to R34 are the same as or different from each other, and are each independently a branched alkyl group; a branched alkoxy group; or a branched thioalkoxy group.

According to an exemplary embodiment of the present specification, in Formulae 2-1 to 2-6, R31 to R34 are the same as or different from each other, and are each independently a branched alkyl group having 3 to 20 carbon atoms; a branched alkoxy group having 3 to 20 carbon atoms; or a branched thioalkoxy group having 3 to 20 carbon atoms.

According to an exemplary embodiment of the present specification, in Formulae 2-1 to 2-6, R31 to R34 are the same as or different from each other, and are each independently a branched alkyl group having 3 to 10 carbon atoms; a branched alkoxy group having 3 to 10 carbon atoms; or a branched thioalkoxy group having 3 to 10 carbon atoms.

According to an exemplary embodiment of the present specification, in Formulae 2-1 to 2-6, R31 to R34 are the same as or different from each other, and are each independently a 2-ethylhexyl group; a 2-ethylhexyloxy group; or a 2-ethylhexylthioxy group.

According to an exemplary embodiment of the present specification, in Formula 1, R1 and R2 are the same as or different from each other, and are each independently a straight-chained or branched alkyl group; a straight-chained or branched alkoxy group; or a straight-chained or branched thioalkoxy group.

According to an exemplary embodiment of the present specification, in Formula 1, R1 and R2 are the same as or different from each other, and are each independently a branched alkyl group; a branched alkoxy group; or a branched thioalkoxy group.

According to an exemplary embodiment of the present specification, in Formula 1, R1 and R2 are the same as or different from each other, and are each independently a branched alkyl group having 3 to 20 carbon atoms; a branched alkoxy group having 3 to 20 carbon atoms; or a branched thioalkoxy group having 3 to 20 carbon atoms.

According to an exemplary embodiment of the present specification, in Formula 1, R1 and R2 are the same as or different from each other, and are each independently a branched alkyl group having 3 to 10 carbon atoms; a branched alkoxy group having 3 to 10 carbon atoms; or a branched thioalkoxy group having 3 to 10 carbon atoms.

According to an exemplary embodiment of the present specification, in Formula 1, R1 and R2 are the same as or different from each other, and are each independently a 2-ethylhexyl group; a 2-ethylhexyloxy group; or a 2-ethylhexylthioxy group.

According to an exemplary embodiment of the present specification, in Formula 1, Y1 and Y2 are the same as or different from each other, and are each independently hydrogen; or a halogen group.

According to an exemplary embodiment of the present specification, in Formula 1, Y1 and Y2 are the same as or different from each other, and are each independently hydrogen; or fluorine.

According to an exemplary embodiment of the present specification, in Formula 1, Y1 and Y2 are hydrogen.

According to an exemplary embodiment of the present specification, in Formula 1, Y1 and Y2 are fluorine.

According to an exemplary embodiment of the present specification, in Formula 1, Y1 is hydrogen.

According to an exemplary embodiment of the present specification, in Formula 1, Y2 is hydrogen.

According to an exemplary embodiment of the present specification, in Formula 1, Y1 is fluorine.

According to an exemplary embodiment of the present specification, in Formula 1, Y2 is fluorine.

According to an exemplary embodiment of the present specification, in Formula 1, n1 and n2 are 0, R1 and R2 are the same as or different from each other, and are each independently a straight-chained or branched alkyl group, and Y1 and Y2 are the same as or different from each other, and are each independently a halogen group.

According to an exemplary embodiment of the present specification, in Formula 1, n1 and n2 are 0, R1 and R2 are the same as or different from each other, and are each independently a branched alkyl group, and Y1 and Y2 are fluorine.

According to an exemplary embodiment of the present specification, in Formula 1, n1 and n2 are 0, R1 and R2 are the same as or different from each other, and are each independently a branched alkyl group having 3 to 20 carbon atoms, and Y1 and Y2 are fluorine.

According to an exemplary embodiment of the present specification, in Formula 1, n1 and n2 are 0, R1 and R2 are the same as or different from each other, and are each independently a branched alkyl group having 3 to 10 carbon atoms, and Y1 and Y2 are fluorine.

According to an exemplary embodiment of the present specification, in Formula 1, n1 and n2 are 0, R1 and R2 are a 2-ethylhexyl group, and Y1 and Y2 are fluorine.

According to an exemplary embodiment of the present specification, EW1 and EW2 are the same as or different from each other, and are each independently represented by the following Formula a.

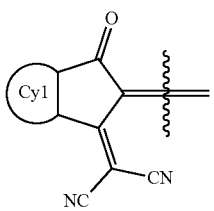

[Formula a]

In Formula a,

Cy1 is an aromatic hydrocarbon ring unsubstituted or substituted with a halogen group, a straight-chained or branched alkyl group, or a straight-chained or branched alkoxy group; or a hetero ring unsubstituted or substituted with a halogen group, a straight-chained or branched alkyl group, or a straight-chained or branched alkoxy group, and ⫽ is a moiety bonded to Formula 1.

According to an exemplary embodiment of the present specification, in Formula a, Cy1 is a benzene ring unsubstituted or substituted with a halogen group, a straight-chained or branched alkyl group, or a straight-chained or branched alkoxy group; a thienothiophene ring; a dibenzothiophene ring; or a thiophene ring unsubstituted or substituted with a halogen group, a straight-chained or branched alkyl group, or a straight-chained or branched alkoxy group.

According to an exemplary embodiment of the present specification, in Formula a, Cy1 is a benzene ring unsubstituted or substituted with fluorine, a methyl group, or a methoxy group; a thienothiophene ring; a dibenzothiophene ring; or a thiophene ring unsubstituted or substituted with a methyl group.

According to an exemplary embodiment of the present specification, EW1 and EW2 are the same as or different from each other, and are each independently selected from the following structures.

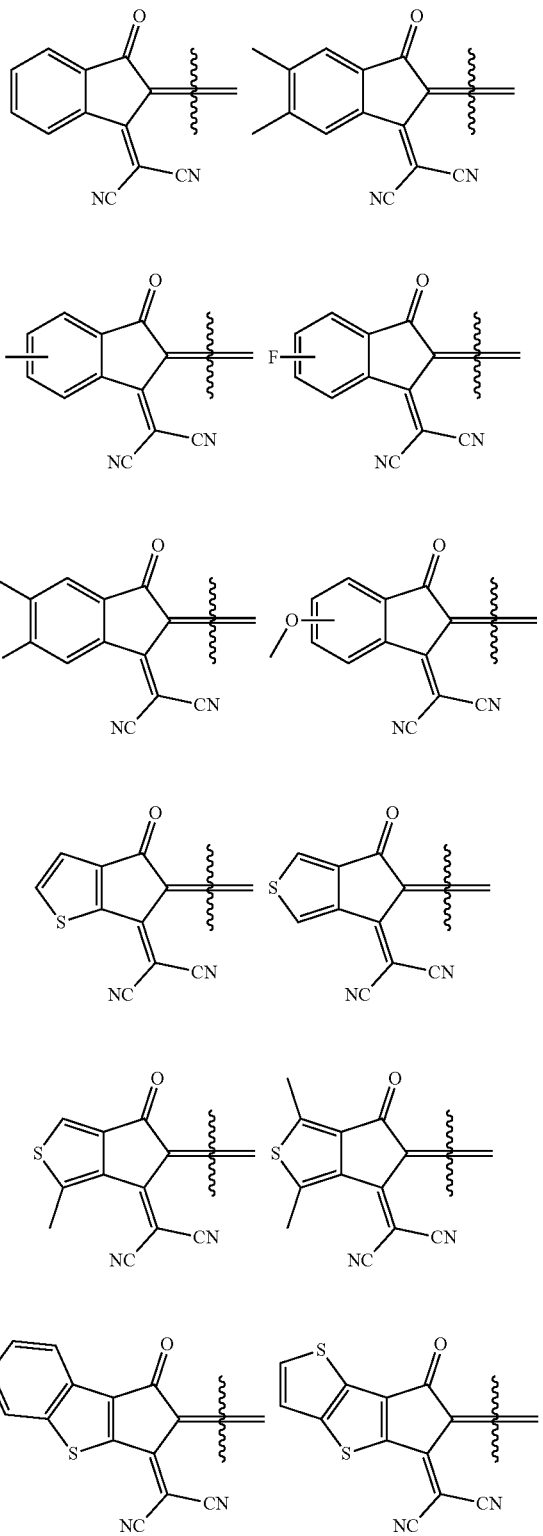

The structures of EW1 and EW2 adjust the energy level of Formula 1, that is, an absorption wavelength of light, and as a result, an organic solar cell comprising the same has an effect of increasing an open-circuit voltage ($V_{oc}$) and a short-circuit current ($J_{sc}$). Specifically, when Cy1 of Formula a is a benzene ring substituted with a halogen group, the absorption region of light is transferred toward the long wavelength, so that a high short-circuit current may be obtained, and when Cy1 is a benzene ring substituted with an alkyl group, the LUMO energy level is increased, so that a high open-circuit voltage may be obtained.

According to an exemplary embodiment of the present specification, in Formula 1, Ar1 to Ar4 are the same as or different from each other, and are each independently an aryl group unsubstituted or substituted with a straight-chained or branched alkyl group, a straight-chained or branched alkoxy group, or a straight-chained or branched thioalkoxy group; or a heteroaryl group unsubstituted or substituted with a straight-chained or branched alkyl group, a straight-chained or branched alkoxy group, or a straight-chained or branched thioalkoxy group.

According to an exemplary embodiment of the present specification, in Formula 1, Ar1 to Ar4 are the same as or different from each other, and are each independently a phenyl group unsubstituted or substituted with a straight-chained or branched alkyl group, a straight-chained or branched alkoxy group, or a straight-chained or branched thioalkoxy group; a furan group unsubstituted or substituted with a straight-chained or branched alkyl group, a straight-chained or branched alkoxy group, or a straight-chained or branched thioalkoxy group; a thiophene group unsubstituted or substituted with a straight-chained or branched alkyl group, a straight-chained or branched alkoxy group, or a straight-chained or branched thioalkoxy group; or a selenophene group unsubstituted or substituted with a straight-chained or branched alkyl group, a straight-chained or branched alkoxy group, or a straight-chained or branched thioalkoxy group.

According to an exemplary embodiment of the present specification, in Formula 1, Ar1 to Ar4 are the same as or different from each other, and are each independently a phenyl group unsubstituted or substituted with a straight-chained or branched alkyl group; a furan group unsubstituted or substituted with a straight-chained or branched alkyl group; a thiophene group unsubstituted or substituted with a straight-chained or branched alkyl group; or a selenophene group unsubstituted or substituted with a straight-chained or branched alkyl group.

According to an exemplary embodiment of the present specification, in Formula 1, Ar1 to Ar4 are the same as or different from each other, and are each independently a phenyl group unsubstituted or substituted with a straight-chained or branched alkyl group having 1 to 30 carbon atoms; a furan group unsubstituted or substituted with a straight-chained or branched alkyl group having 1 to 30 carbon atoms; a thiophene group unsubstituted or substituted with a straight-chained or branched alkyl group having 1 to 30 carbon atoms; or a selenophene group unsubstituted or substituted with a straight-chained or branched alkyl group having 1 to 30 carbon atoms.

According to an exemplary embodiment of the present specification, in Formula 1, Ar1 to Ar4 are the same as or different from each other, and are each independently a phenyl group unsubstituted or substituted with a straight-chained or branched alkyl group having 1 to 10 carbon atoms; a furan group unsubstituted or substituted with a straight-chained or branched alkyl group having 1 to 10 carbon atoms; a thiophene group unsubstituted or substituted with a straight-chained or branched alkyl group having 1 to 10 carbon atoms; or a selenophene group unsubstituted or substituted with a straight-chained or branched alkyl group having 1 to 10 carbon atoms.

According to an exemplary embodiment of the present specification, in Formula 1, Ar1 to Ar4 are the same as or different from each other, and are each independently a phenyl group substituted with an n-hexyl group; a furan group substituted with an n-hexyl group; a thiophene group substituted with an n-hexyl group; or a selenophene group substituted with an n-hexyl group.

According to an exemplary embodiment of the present specification, in Formula 1, Ar1 to Ar4 are the same as or different from each other, and are each independently selected from the following structures.

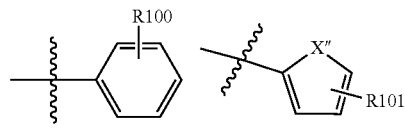

In the structures,

X" is S, O, or Se,

R100 and R101 are the same as or different from each other, and are each independently a straight-chained or branched alkyl group, a straight-chained or branched alkoxy group, or a straight-chained or branched thioalkoxy group, and ⊹ is a moiety bonded to Formula 1.

According to another exemplary embodiment of the present specification, R100 and R101 are the same as or different from each other, and are each independently a straight-chained or branched alkyl group.

According to still another exemplary embodiment of the present specification, R100 and R101 are the same as or different from each other, and are each independently a straight-chained or branched alkyl group having 1 to 30 carbon atoms.

According to yet another exemplary embodiment of the present specification, R100 and R101 are the same as or different from each other, and are each independently a straight-chained or branched alkyl group having 1 to 10 carbon atoms.

According to still yet another exemplary embodiment of the present specification, R100 and R101 are the same as or different from each other, and are each independently a straight-chained alkyl group having 1 to 30 carbon atoms.

According to a further exemplary embodiment of the present specification, R100 and R101 are the same as or different from each other, and are each independently a straight-chained alkyl group having 1 to 10 carbon atoms.

According to another further exemplary embodiment of the present specification, R100 and R101 are an n-hexyl group.

According to an exemplary embodiment of the present specification, in Formula 1, Ar1 to Ar4 are the same as or different from each other, and are each independently selected from the following structures.

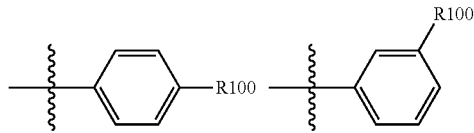

-continued

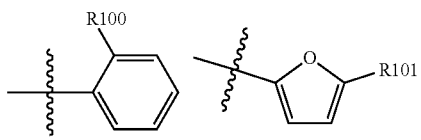
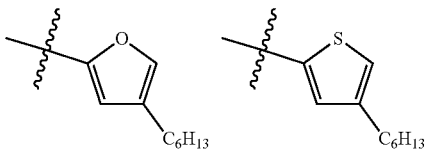

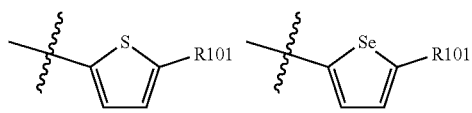
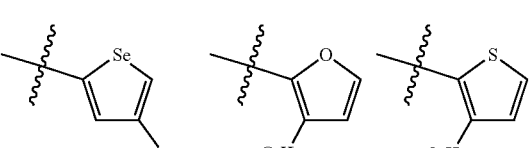

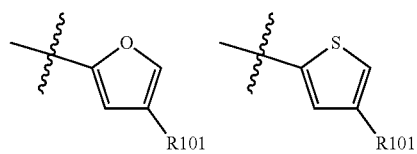
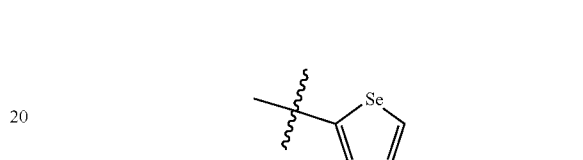

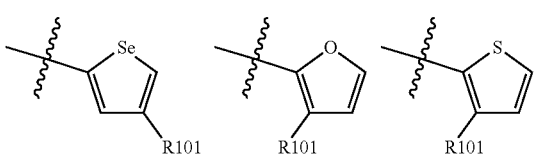
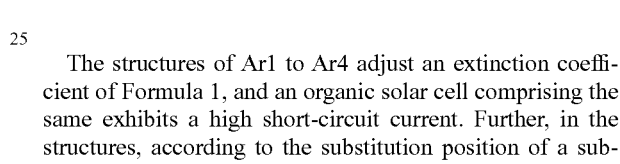

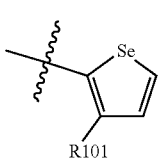

In the structures, R100 and R101 are the same as those described above.

According to an exemplary embodiment of the present specification, in Formula 1, Ar1 to Ar4 are the same as or different from each other, and are each independently selected from the following structures.

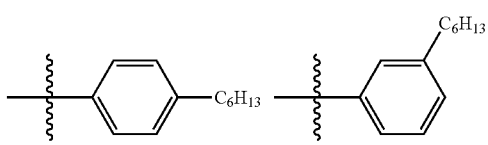

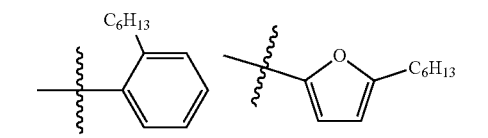

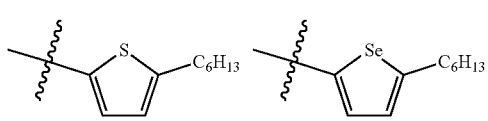

The structures of Ar1 to Ar4 adjust an extinction coefficient of Formula 1, and an organic solar cell comprising the same exhibits a high short-circuit current. Further, in the structures, according to the substitution position of a substituted alkyl group in a phenyl group, thiophene, and thienothiophene, the HOMO and LUMO energy levels of Formula 1 can be adjusted, thereby bringing an effect of increasing the open-circuit voltage of an organic solar cell. In addition, for the position of a substituted alkyl group in the phenyl group, thiophene, and thienothiophene, the arrangement of the molecules in a film state can induce a face-on molecular arrangement favorable to a device of an organic solar cell, so that an organic solar cell comprising the same exhibits a high short-circuit current and a high fill factor.

According to an exemplary embodiment of the present specification, in Formula 1, Ar1 to Ar4 have a substituent at the meta position with the following structure.

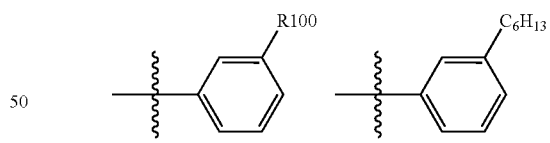

In the structure, R100 is the same as that described above.

In particular, when Ar1 to Ar4 have a substituent at the meta position, it is possible to obtain higher photoelectric conversion efficiency than the case where Ar1 to Ar4 have a substituent at the para position. Specifically, the solubility problem is improved, so that a thin film in a blend state of a donor and an acceptor is easily formed. Further, the mobility is increased due to the increase in interaction between molecules. As a result, the photoelectric conversion efficiency is increased.

According to an exemplary embodiment of the present specification, Formula 1 is selected from the following compounds.

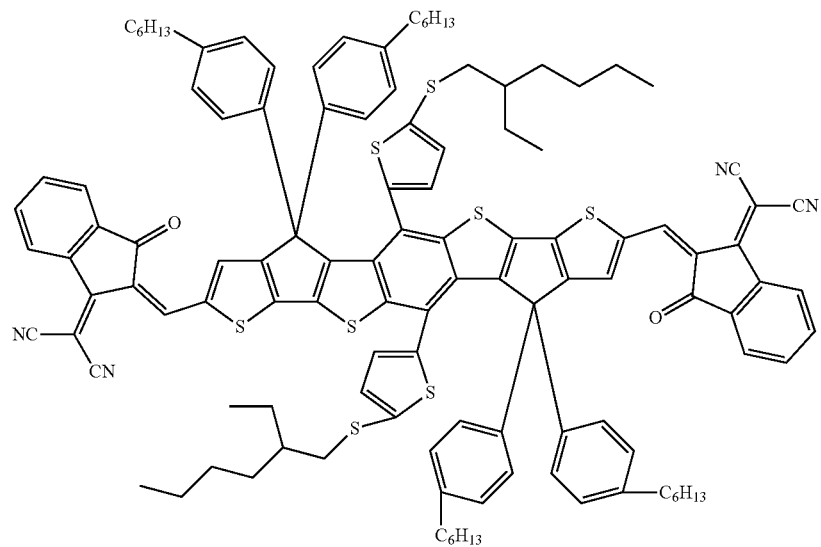
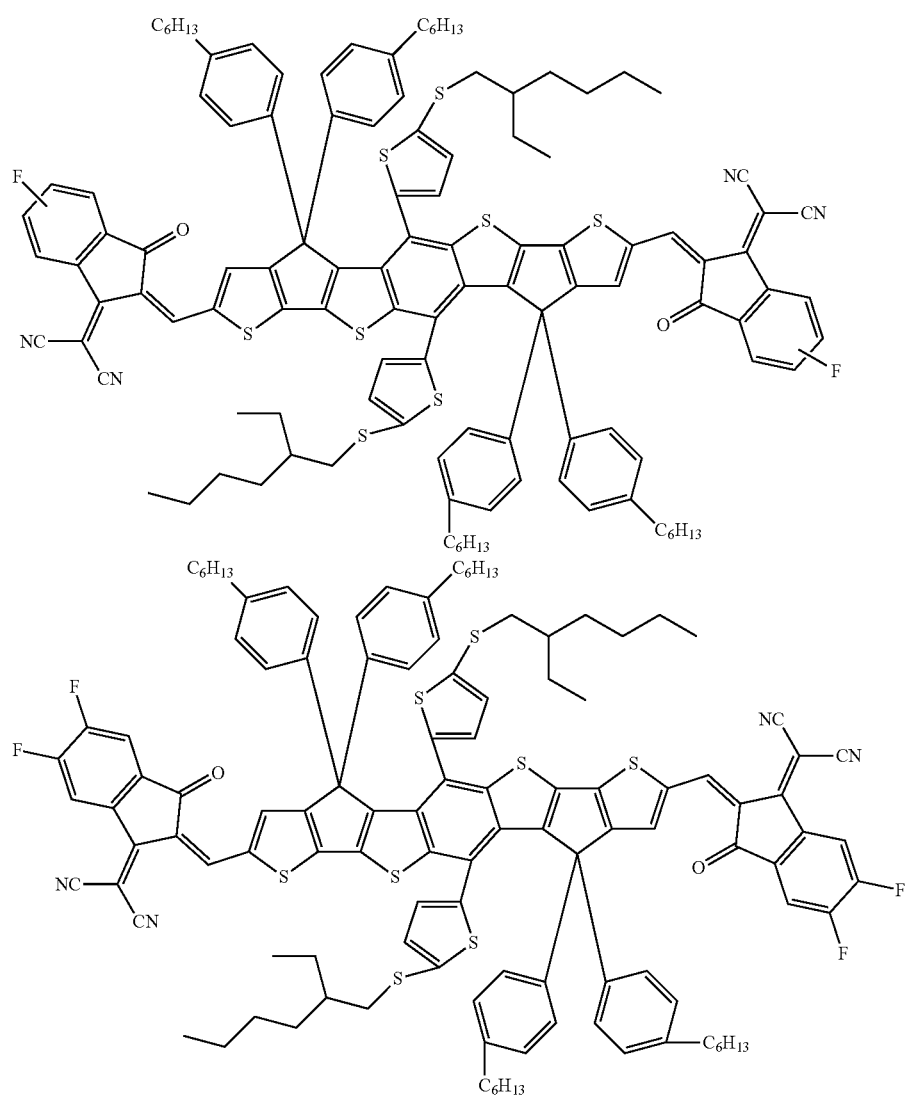

-continued
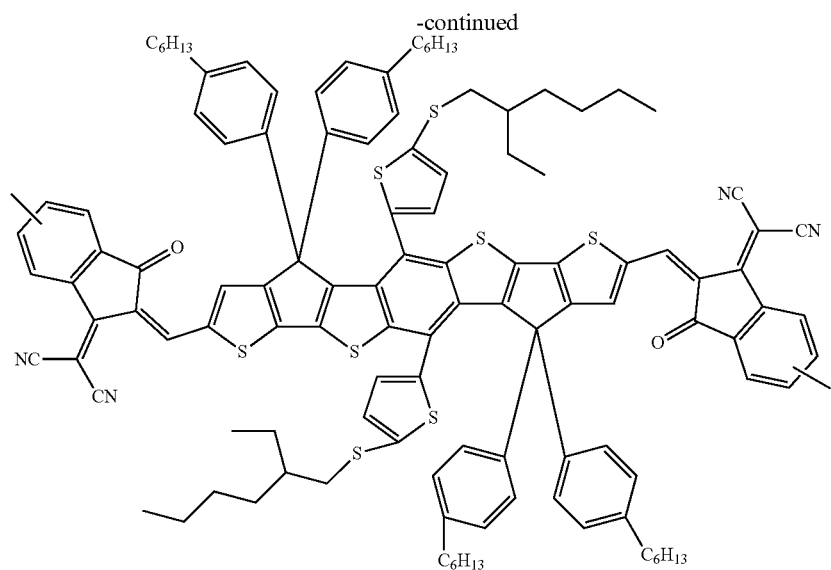
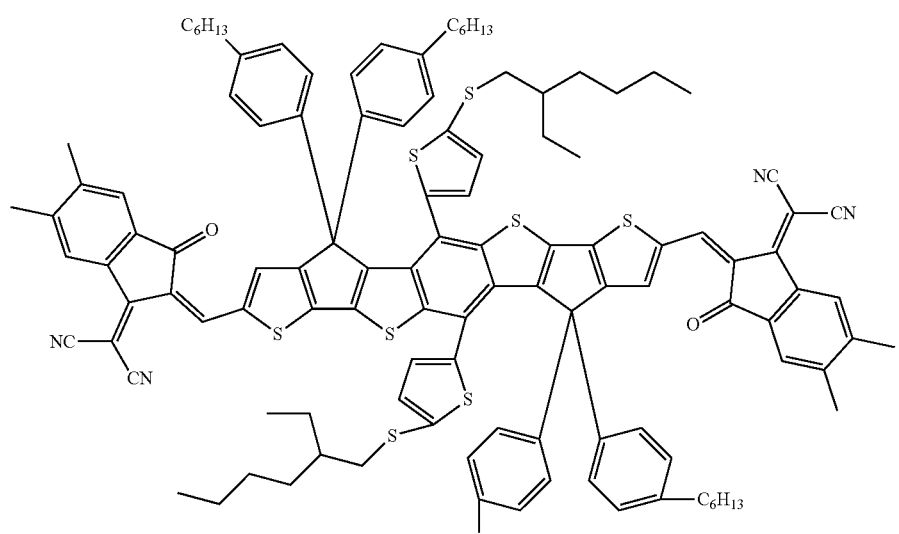
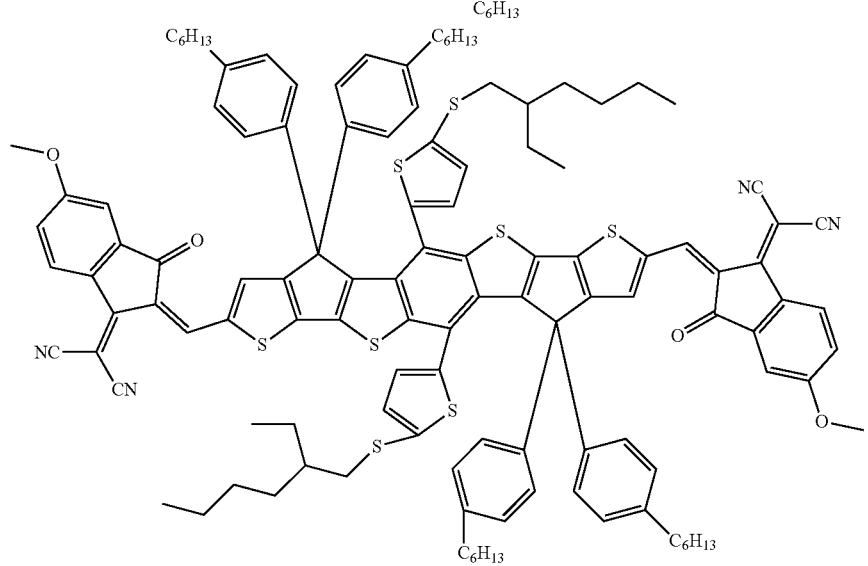

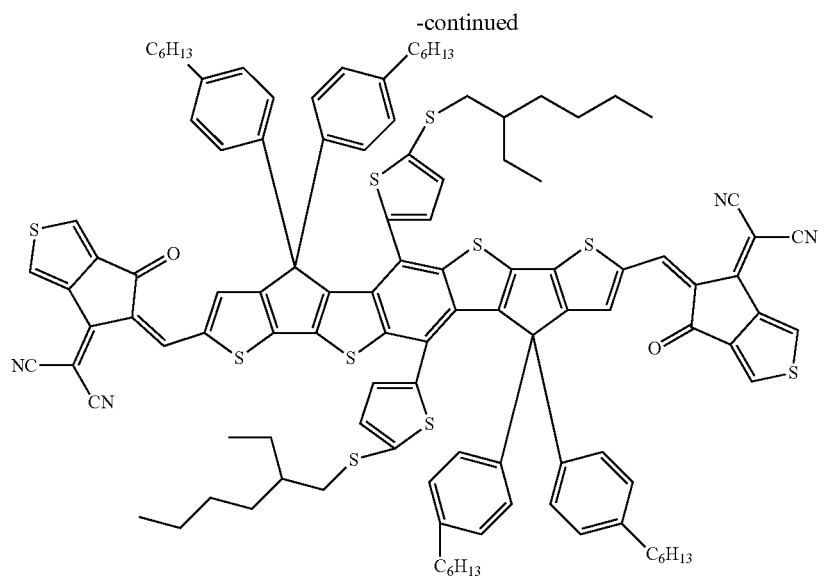
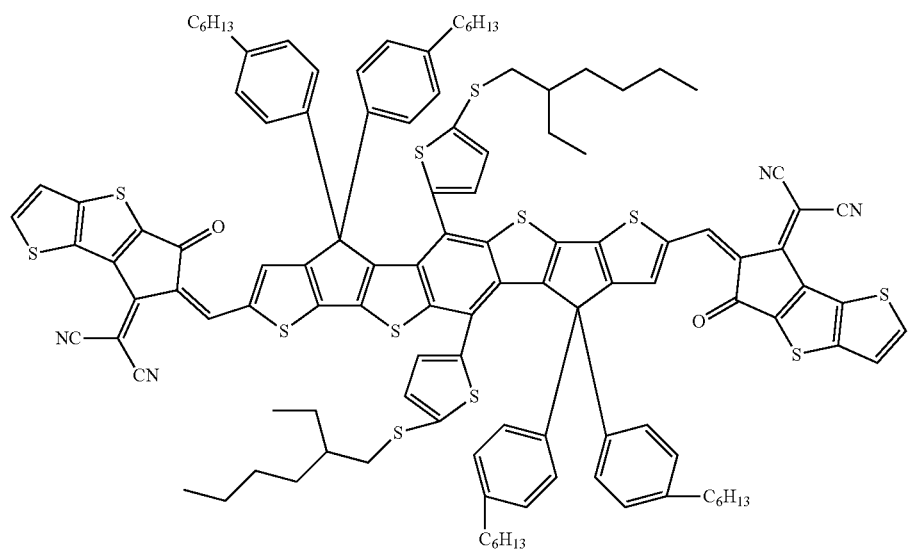
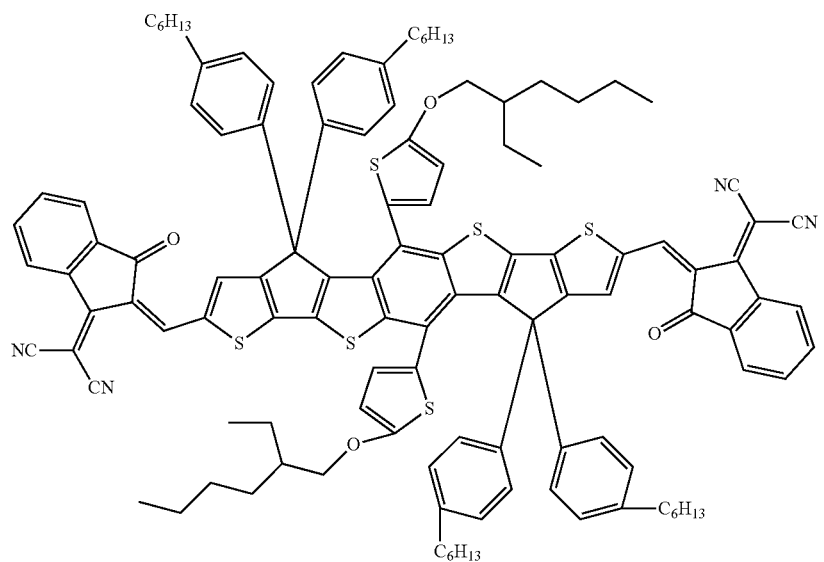

-continued
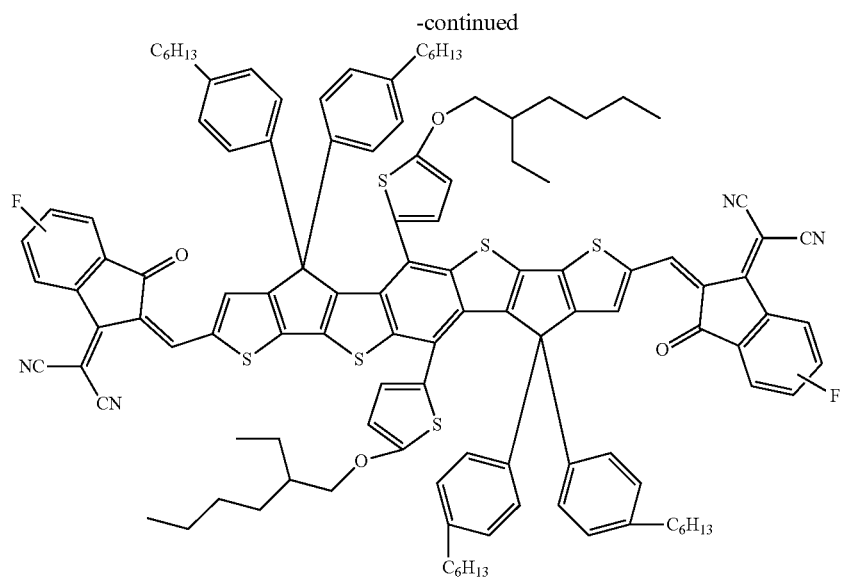
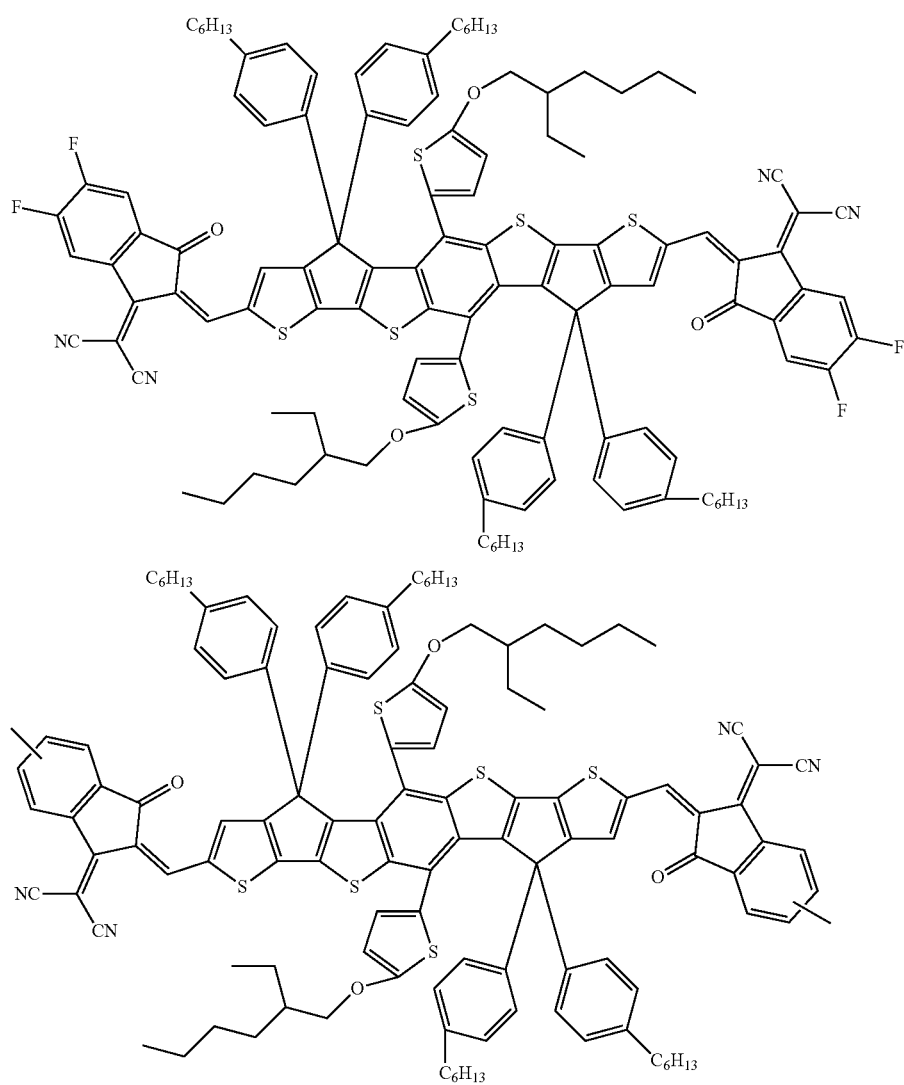

-continued
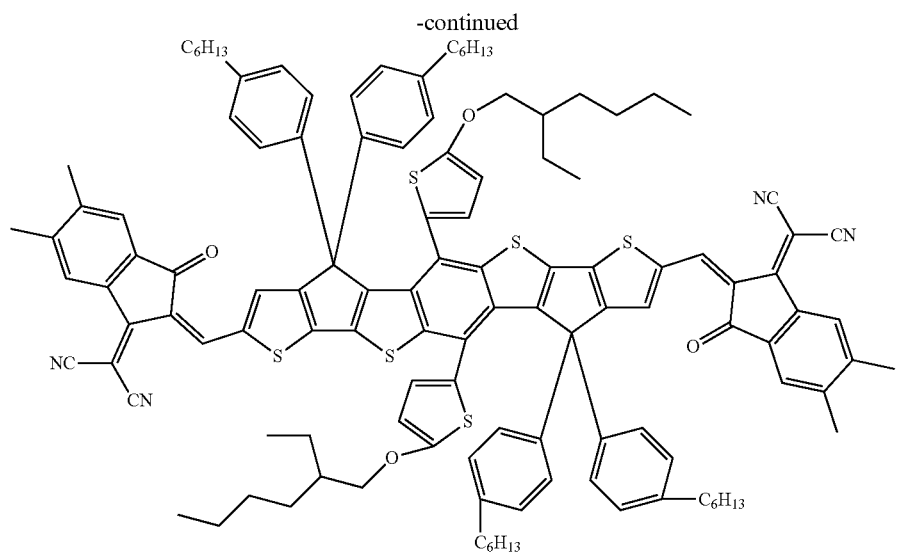
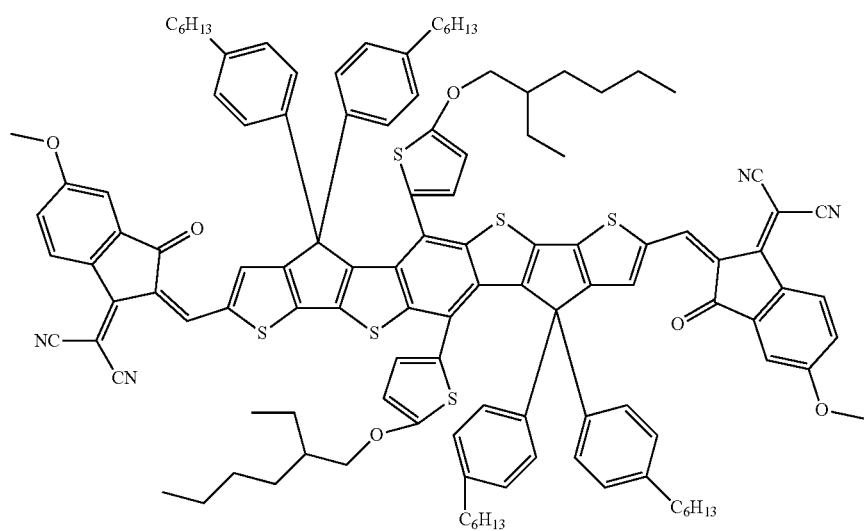
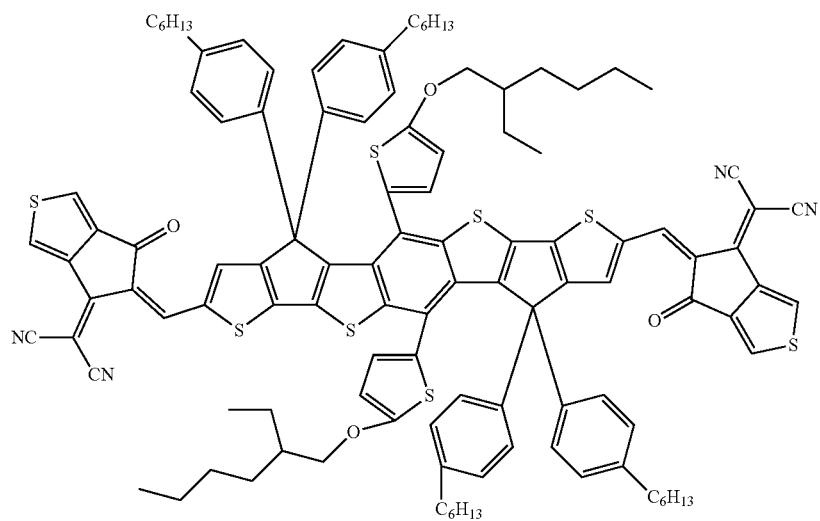

-continued
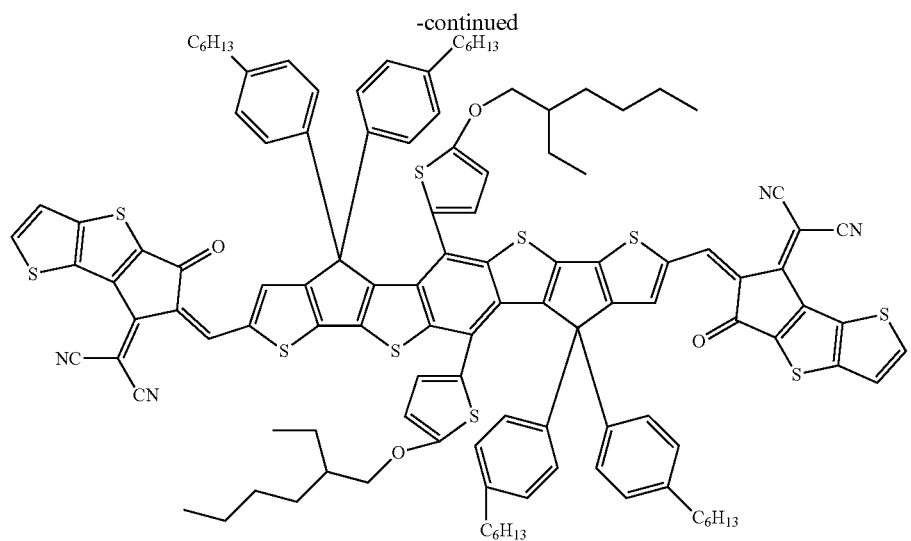
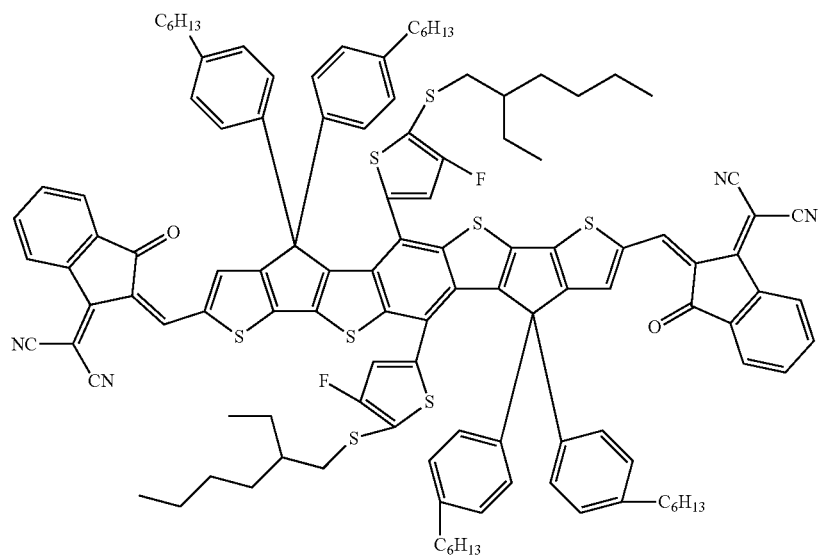
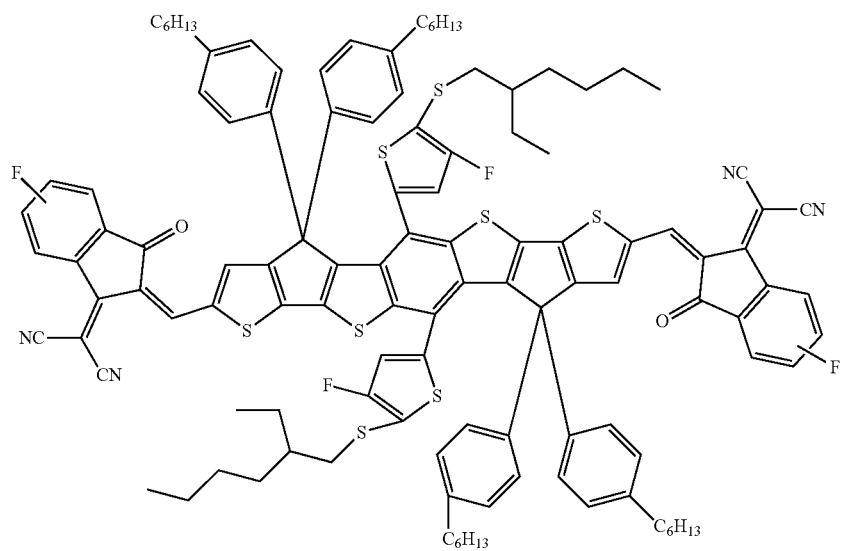

-continued
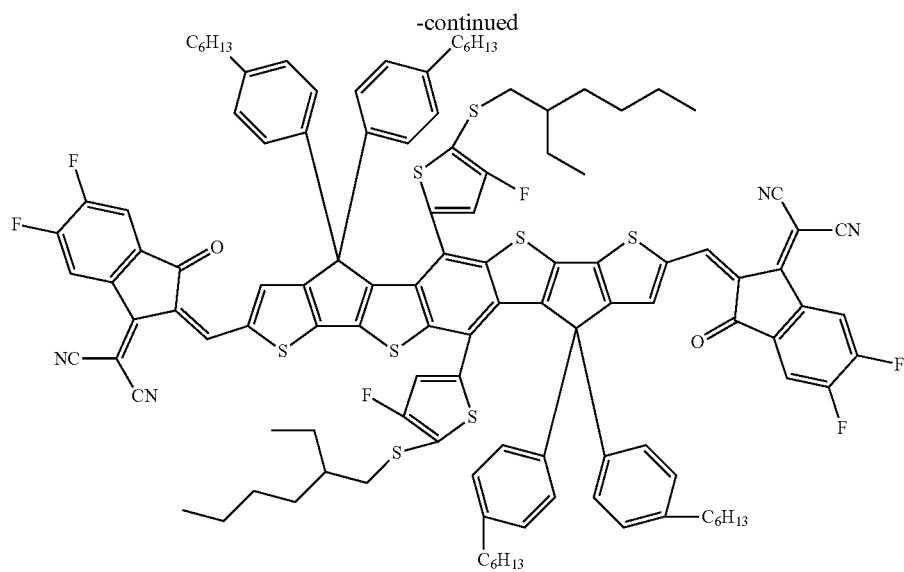
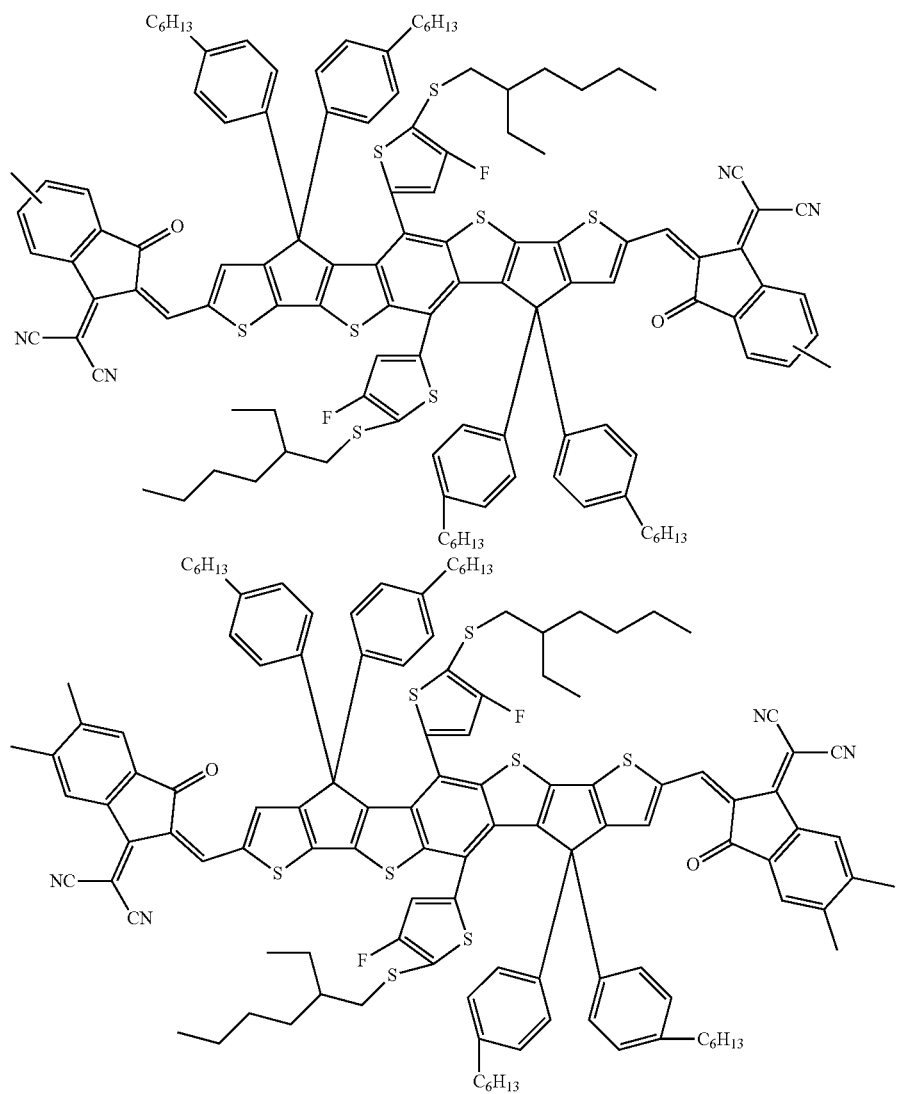

-continued
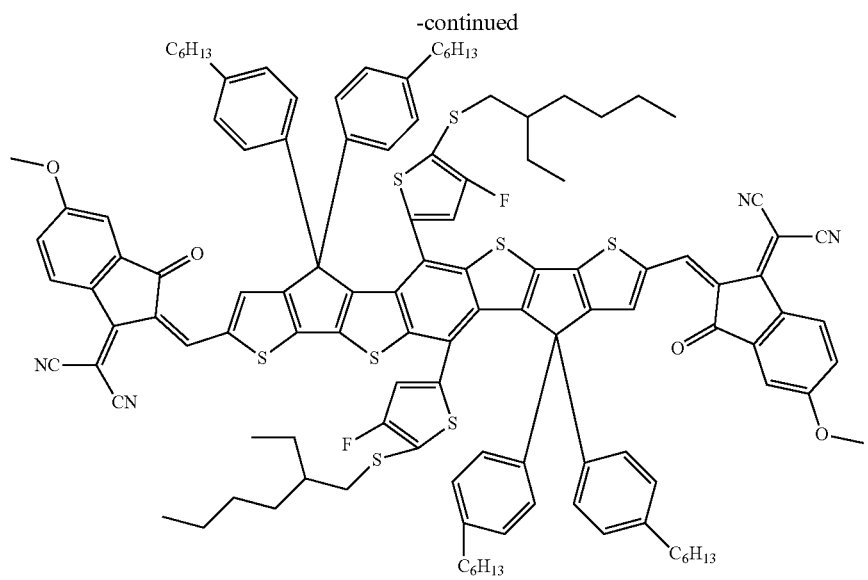
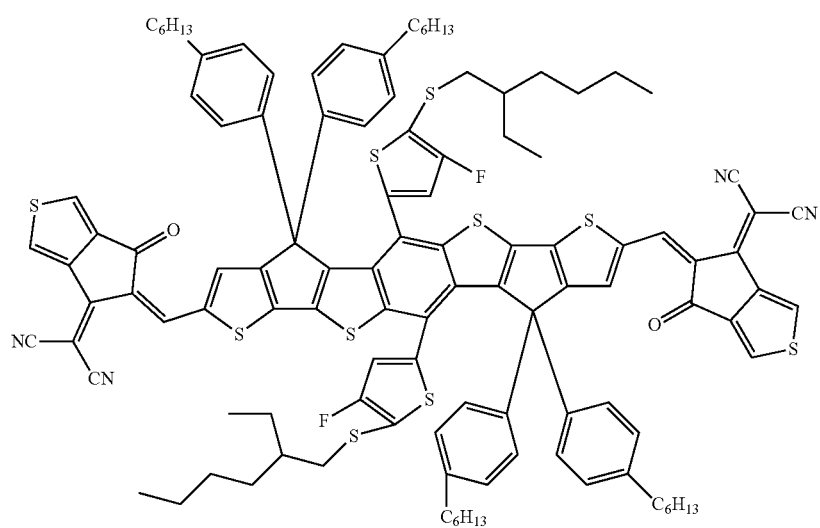
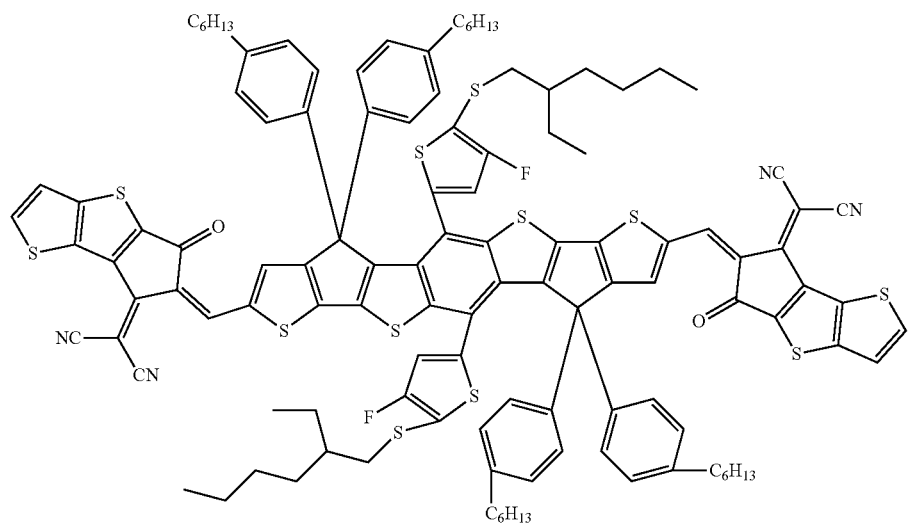

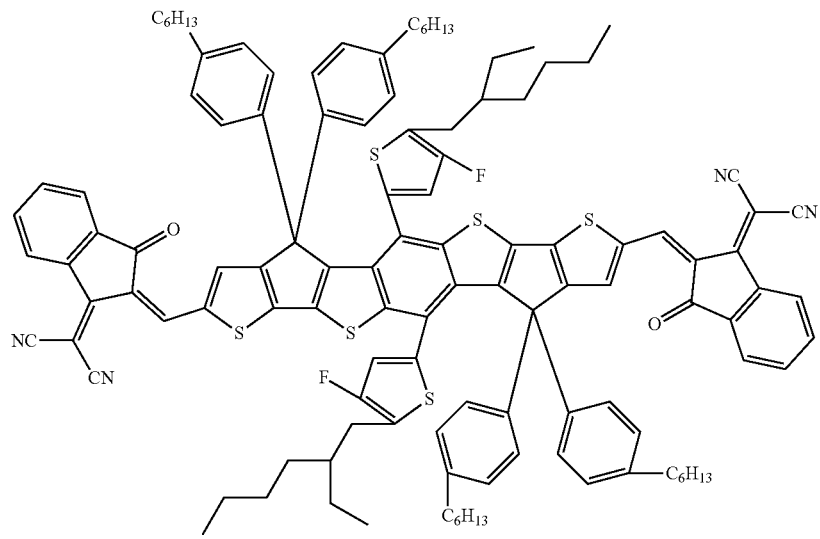
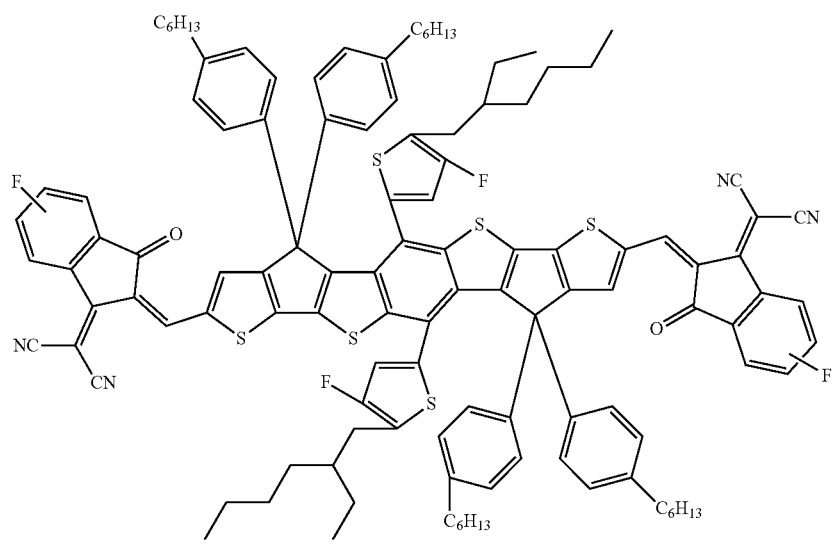
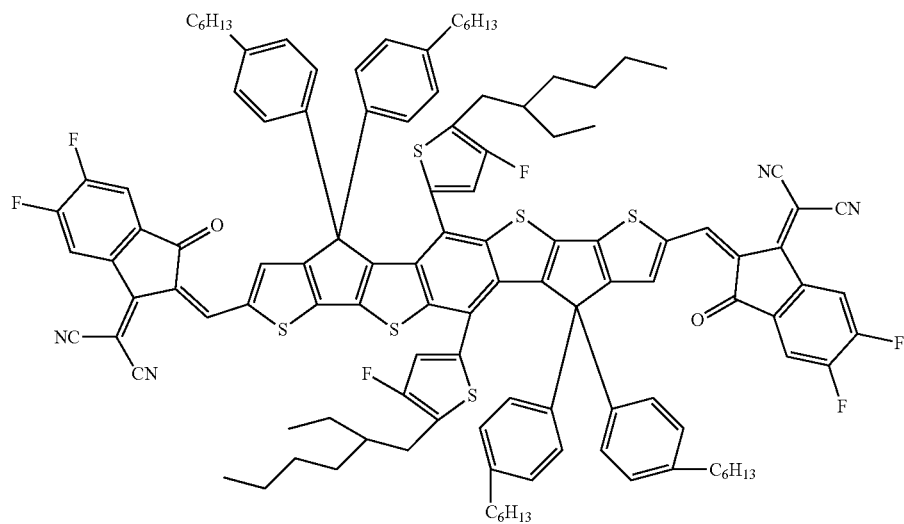

-continued
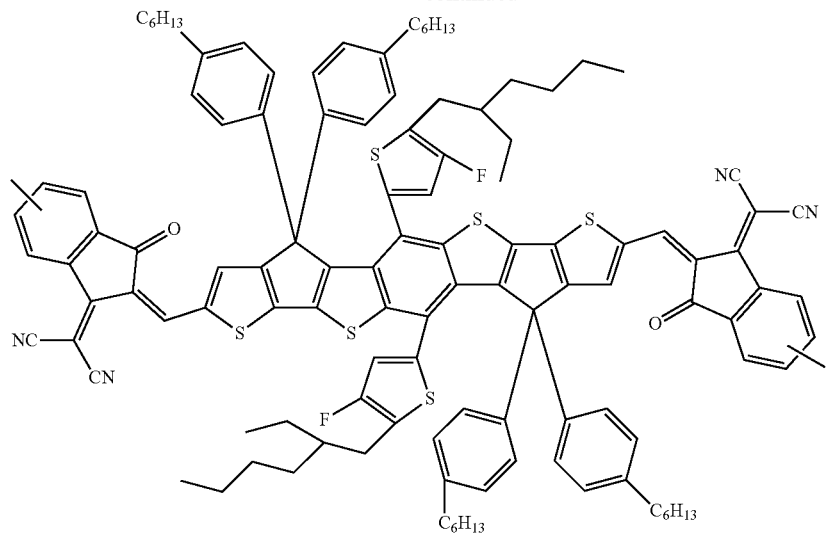
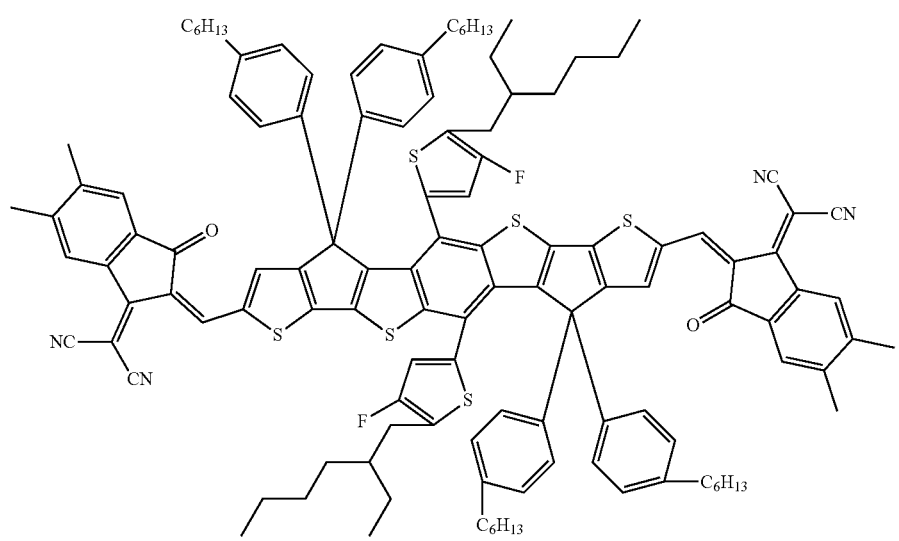
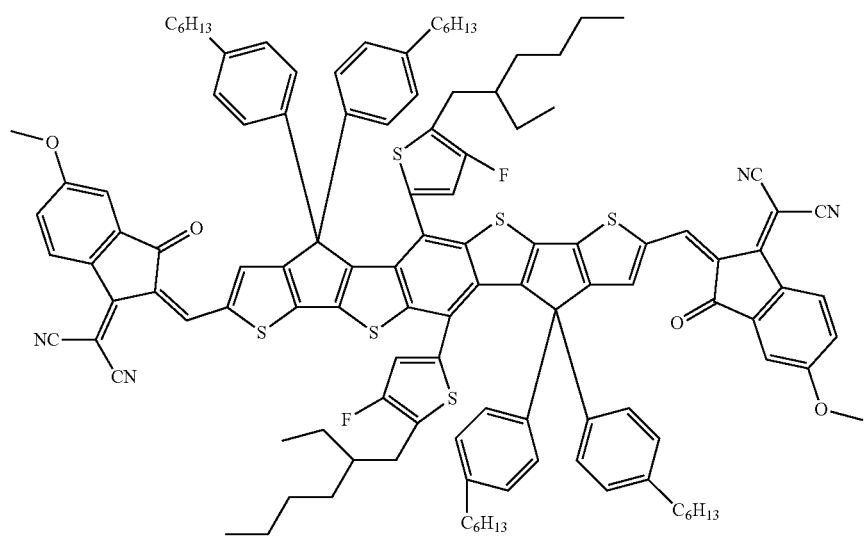

-continued
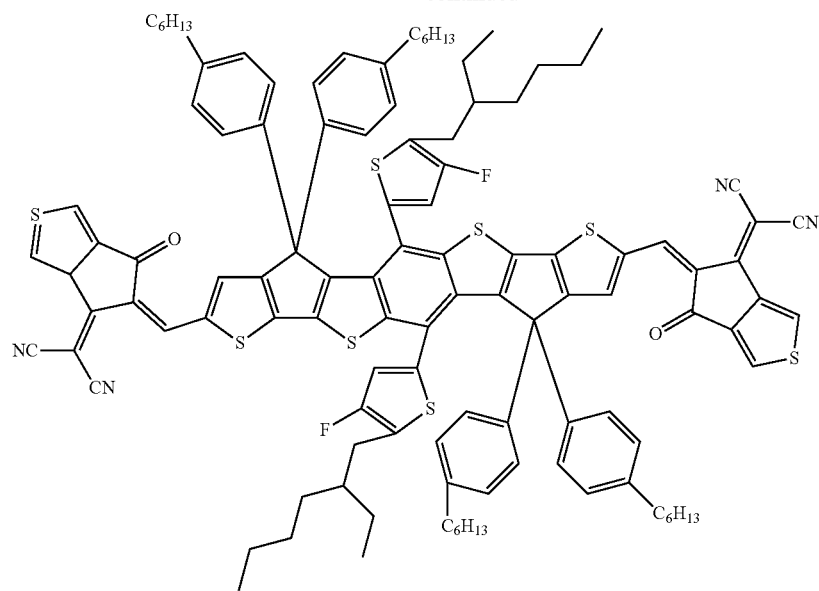
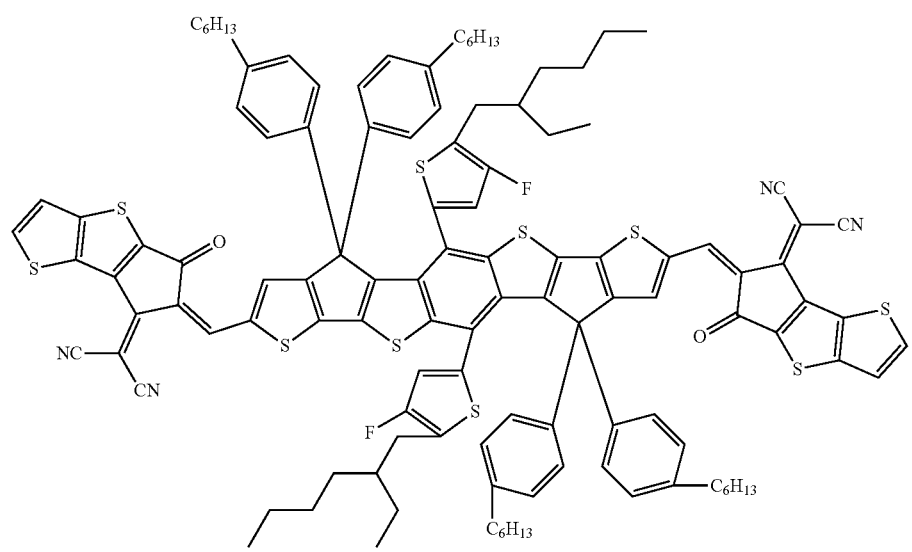
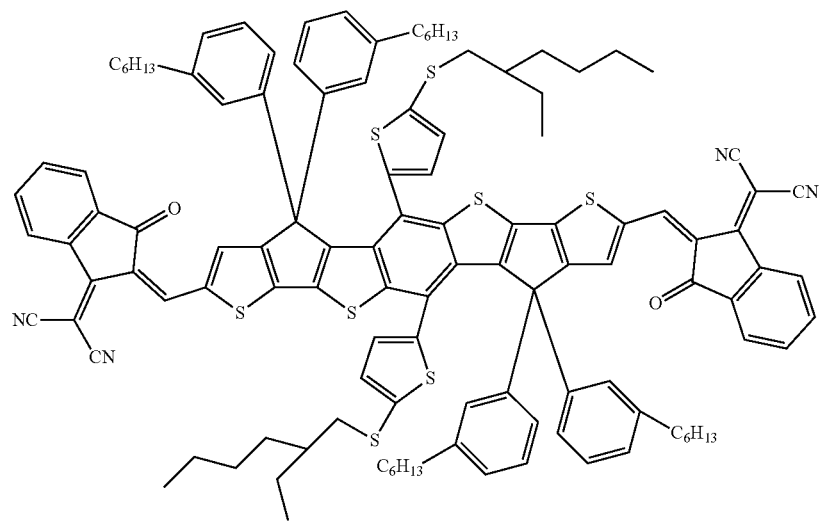

-continued
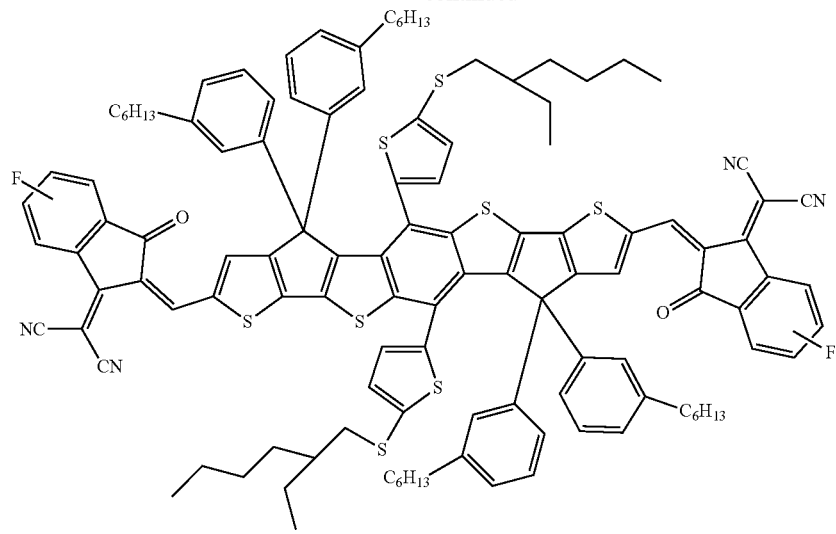
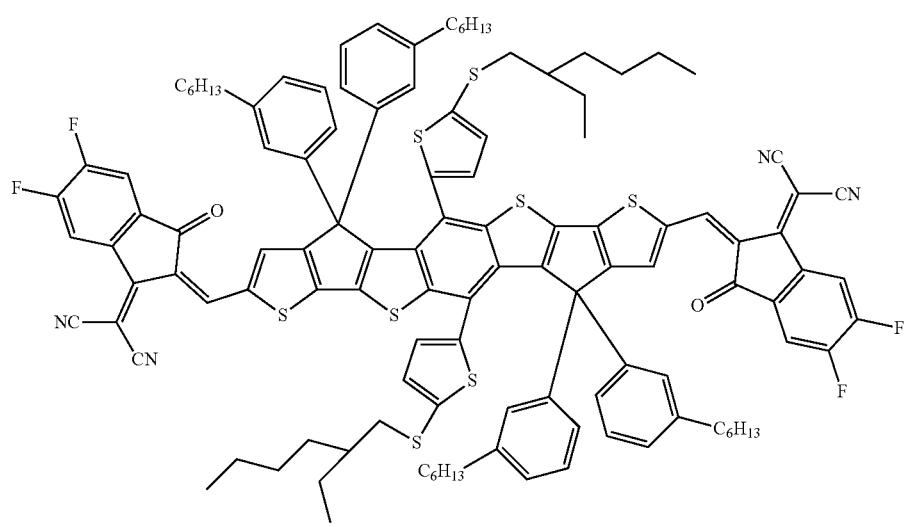
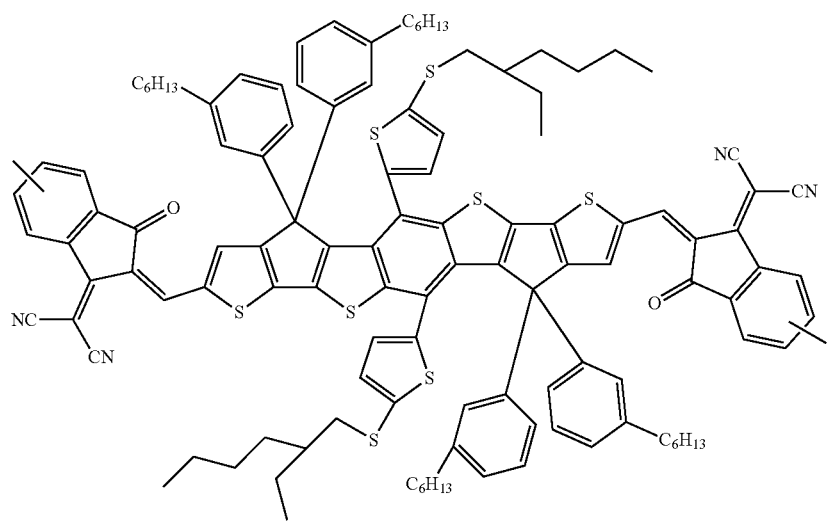

-continued
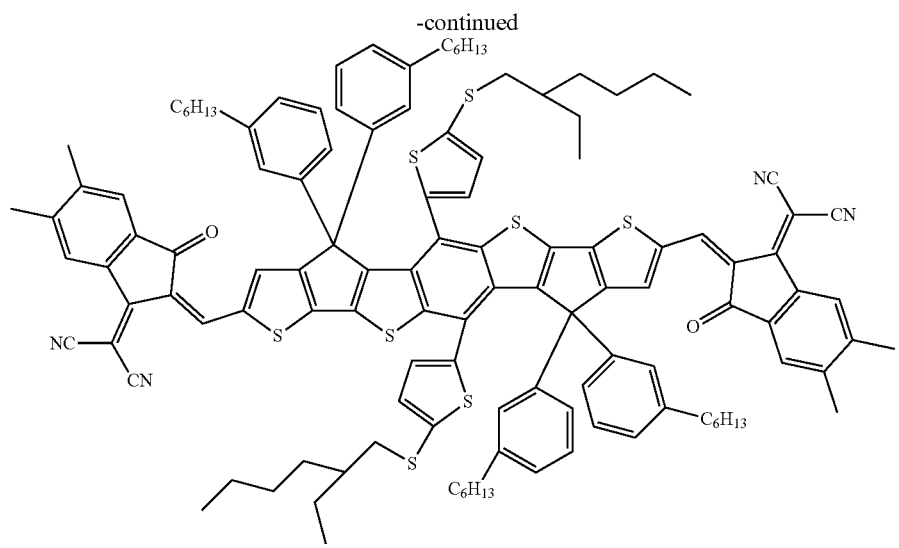
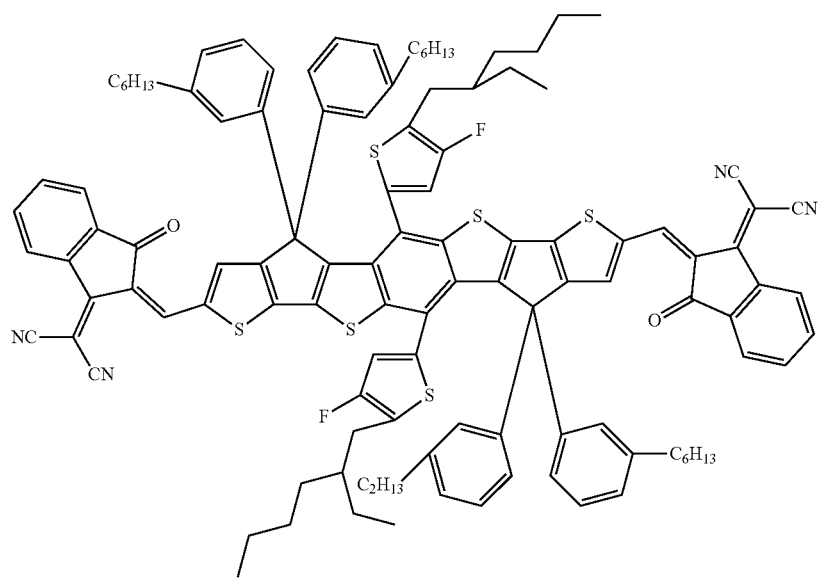
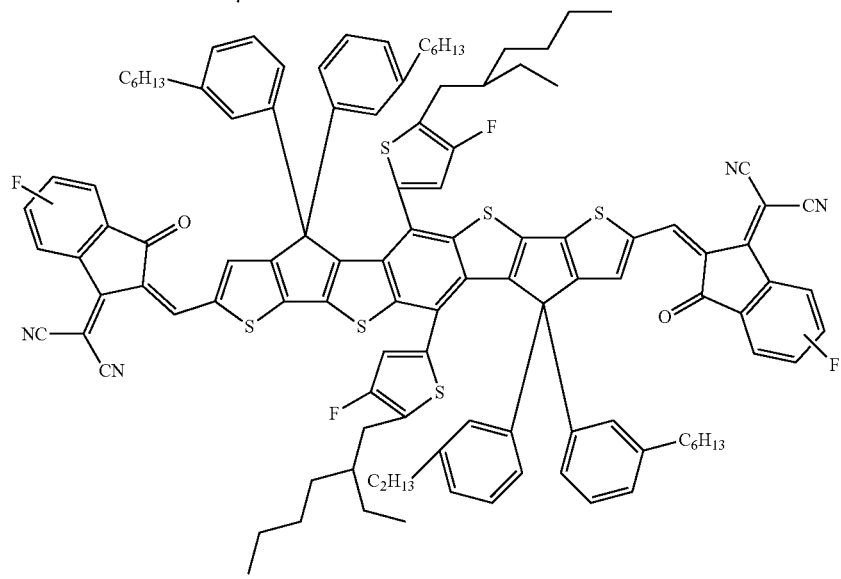

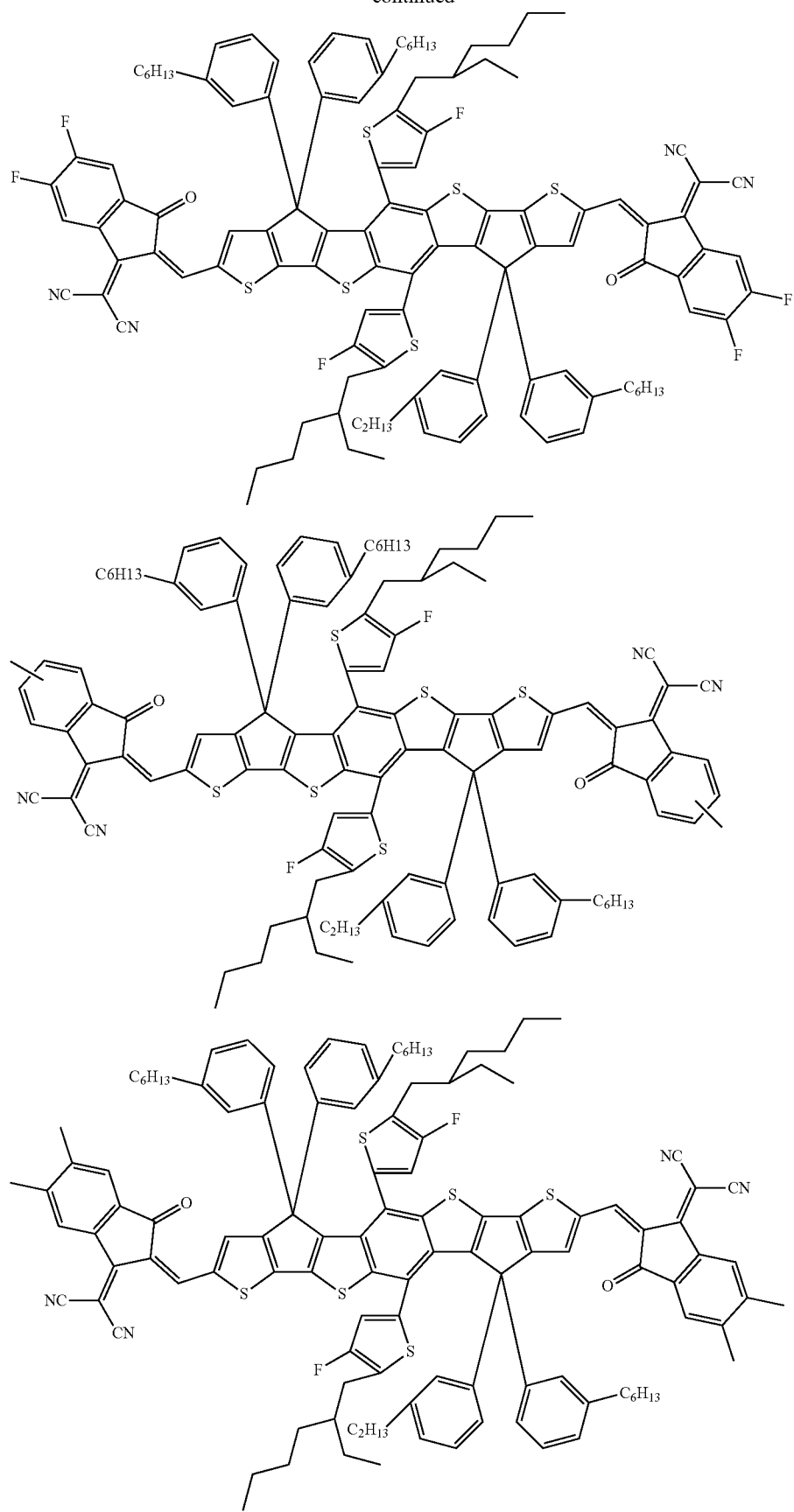

-continued
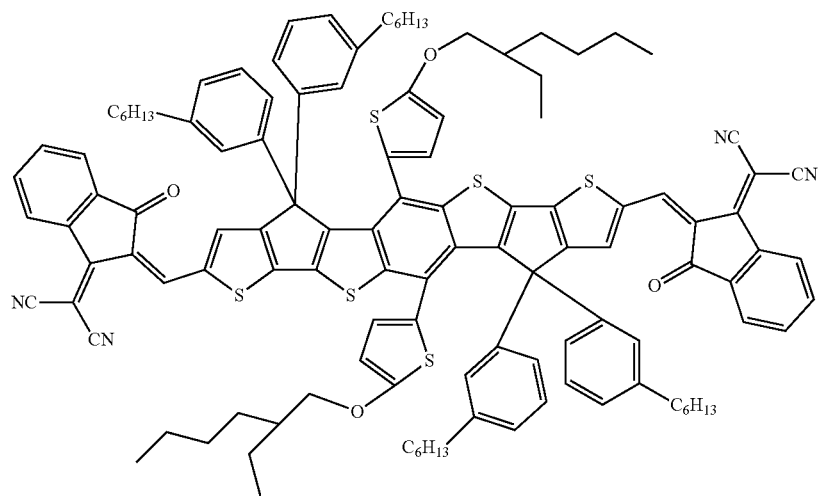
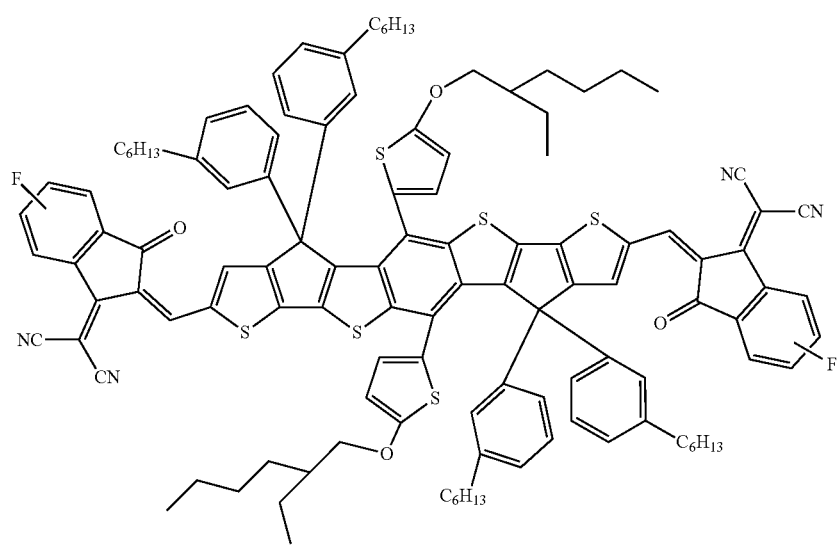
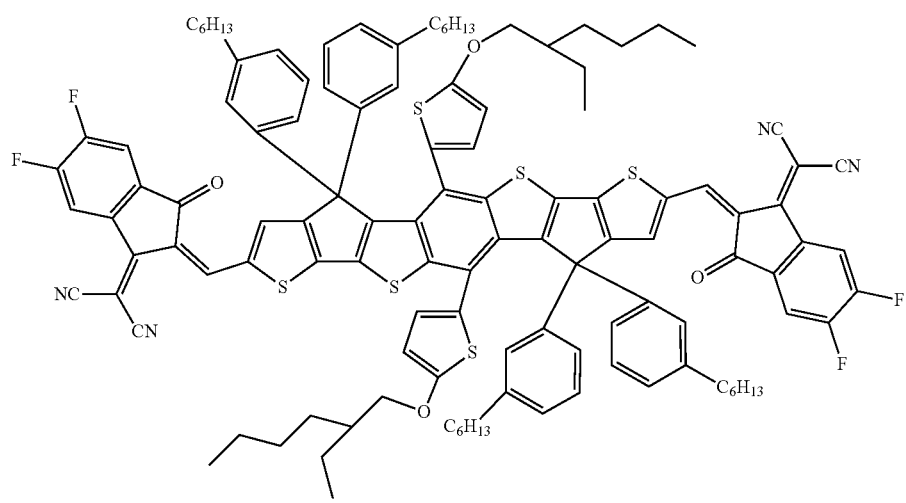

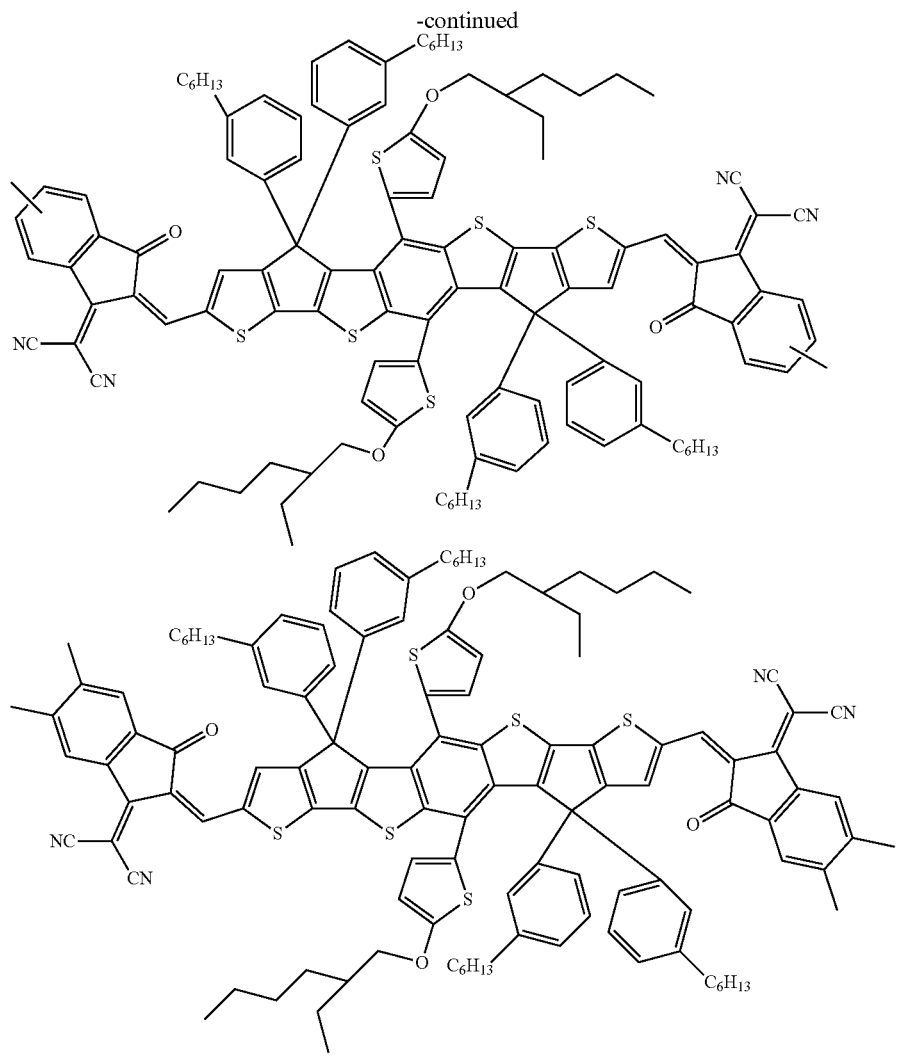

The present specification provides a composition for an organic electronic device, including the heterocyclic compound represented by Formula 1.

According to an exemplary embodiment of the present specification, the composition for an organic electronic device comprises an electron donor material and an electron acceptor material, and the electron acceptor material includes the heterocyclic compound.

Further, it is possible to apply most of the electron donor materials having a maximum absorption wavelength in a visible ray region to the electron donor material in the composition for an organic electronic device, but the electron donor material is not limited thereto.

According to an exemplary embodiment of the present specification, a material applied in the art may be used as the electron donor material, and the electron donor material may include, for example, one or more materials selected from the group consisting of poly 3-hexyl thiophene (P3HT), poly[N-9'-heptadecanyl-2,7-carbazole-alt-5,5-(4'-7'-di-2-thienyl-2',1',3'-benzothiadiazole)] (PCDTBT), poly[2,6-(4,4-bis-(2-ethylhexyl)-4H-cyclopenta[2,1-b;3,4-b]dithiophene)-alt-4,7-(2,1,3-benzothiadiazole)] (PCPDTBT), poly[2,7-(9,9-dioctyl-fluorene)-alt-5,5-(4,7-di 2-thienyl-2,1,3-benzothiadiazole)] (PFO-DBT), poly[[4,8-bis[(2-ethylhexyl)oxy]benzo[1,2-b:4,5-b']dithiophene-2,6-diyl][3-fluoro-2-[(2-ethylhexyl)carbonyl]thieno[3,4-b]thiophenediyl]] (PTB7 or PTB7-Th), poly[2,7-(9,9-dioctyl-dibenzosilole)-alt-4,7-bis(thiophen-2-yl)benzo-2,1,3-thiadiazole] (PSiF-DBT), and poly(benzodithiophene-benzotriazole) (PBDB-T).

According to an exemplary embodiment of the present specification, the composition for an organic electronic device comprises an electron donor material and an electron acceptor material, and comprises the electron donor material and the electron acceptor material at a weight ratio of 1:99 to 99:1.

According to an exemplary embodiment of the present specification, the photoactive layer comprises an electron donor material and an electron acceptor material, and comprises the electron donor material and the electron acceptor material at a weight ratio of 1:5 to 5:1.

According to an exemplary embodiment of the present specification, the electron donor and the electron acceptor constitute a bulk heterojunction (BHJ).

According to an exemplary embodiment of the present specification, the composition for an organic electronic device may further comprise a solvent.

In an exemplary embodiment of the present specification, the composition for an organic electronic device may be in a liquid phase. The "liquid phase" means that the composition is in a liquid state at room temperature under atmospheric pressure.

In an exemplary embodiment of the present specification, examples of the solvent include: a chlorine-based solvent such as chloroform, methylene chloride, 1,2-dichloroethane, 1,1,2-trichloroethane, chlorobenzene, and o-dichlorobenzene; an ether-based solvent such as tetrahydrofuran and dioxane; an aromatic hydrocarbon-based solvent such as toluene, xylene, trimethylbenzene, and mesitylene; an aliphatic hydrocarbon-based solvent such as cyclohexane, methylcyclohexane, n-pentane, n-hexane, n-heptane, n-octane, n-nonane, and n-decane; a ketone-based solvent such as acetone, methyl ethyl ketone, and cyclohexanone; an ester-based solvent such as ethyl acetate, butyl acetate, and ethyl cellosolve acetate; a polyhydric alcohol such as ethylene glycol, ethylene glycol monobutyl ether, ethylene glycol monoethyl ether, ethylene glycol monomethyl ether, dimethoxy ethane, propylene glycol, diethoxymethane, triethylene glycol monoethyl ether, glycerin, and 1,2-hexanediol and a derivative thereof; an alcohol-based solvent such as methanol, ethanol, propanol, isopropanol, and cyclohexanol; a sulfoxide-based solvent such as dimethyl sulfoxide; an amide-based solvent such as N-methyl-2-pyrrolidone and N,N-dimethylformamide; a benzoate-based solvent such as methyl benzoate, butyl benzoate, and 3-phenoxybenzoate; and a solvent such as tetralin, but the solvent is sufficient as long as the solvent may dissolve or disperse the compound according to an exemplary embodiment of the present specification, and is not limited thereto.

In another exemplary embodiment, the solvents may be used either alone or in a mixture of two or more solvents.

In still another exemplary embodiment, a boiling point of the solvent is preferably 40 to 250° C., and more preferably 60 to 230° C., but is not limited thereto.

In yet another exemplary embodiment, a viscosity of the single solvent or the mixed solvent is preferably 1 CP to 10 CP, and more preferably 3 CP to 8 CP, but is not limited thereto.

In still yet another exemplary embodiment, a concentration of the composition for an organic electronic device is preferably 0.1 wt/v % to 20 wt/v %, and more preferably 0.5 wt/v % to 5 wt/v %, but is not limited thereto.

According to an exemplary embodiment of the present specification, the composition for an organic electronic device further comprises an additive.

According to an exemplary embodiment of the present specification, the additive has a molecular weight of 50 g/mol to 1,000 g/mol.

According to an exemplary embodiment of the present specification, the additive is comprised in an amount of 0.1 to 10 parts by weight based on the composition for an organic electronic device.

In another exemplary embodiment, the additive is an organic material having a boiling point of 30° C. to 300° C.

In the present specification, the organic material means a material including at least one or more carbon atoms.

In one exemplary embodiment, the additive may further include one or two additives selected from the group consisting of 1,8-diiodooctane (DIO), 1-chloronaphthalene (1-CN), diphenylether (DPE), octane dithiol, and tetrabromothiophene.

The present specification provides an organic electronic device formed by using the composition for an organic electronic device.

The present specification provides an organic electronic device comprising: a first electrode; a second electrode provided to face the first electrode; and an organic material layer having one or more layers provided between the first electrode and the second electrode, in which one or more layers of the organic material layer comprise the composition for an organic electronic device.

According to an exemplary embodiment of the present specification, the organic electronic device is selected from the group consisting of an organic photoelectric device, an organic transistor, an organic solar cell, and an organic light emitting device.

According to an exemplary embodiment of the present specification, the organic electronic device may be an organic solar cell.

According to an exemplary embodiment of the present specification, the organic electronic device is an organic solar cell comprising: a first electrode; a second electrode provided to face the first electrode; and an organic material layer having one or more layers provided between the first electrode and the second electrode, in which one or more layers of the organic material layer comprise the composition for an organic electronic device.

According to an exemplary embodiment of the present specification, the organic material layer comprises a photoactive layer, and the photoactive layer comprises the composition for an organic electronic device.

According to an exemplary embodiment of the present specification, the photoactive layer comprises the composition for an organic electronic device, the composition for an organic electronic device comprises the above-described heterocyclic compound, and a bandgap of the heterocyclic compound is 1 eV to 3 eV, specifically 1 eV to 2 eV, and more specifically 1 eV to 1.6 eV.

For the bandgap, the HOMO and LUMO energy levels were measured through the cyclic voltammetry (CV), and a difference between the HOMO and LUMO energy levels is the bandgap. In the cyclic voltammetry (CV), the HOMO and LUMO energy levels are measured by using glassy carbon as a working electrode through 0.1 M $[nBu_4N]^+$ $[PF_6]^-$ and an acetonitrile solution, but the measurement method is not limited thereto.

The organic solar cell according to an exemplary embodiment of the present specification comprises a first electrode, a photoactive layer, and a second electrode. The organic solar cell may further comprise a substrate, a hole transport layer, and/or an electron transport layer.

According to an exemplary embodiment of the present specification, when the organic solar cell accepts a photon from an external light source, an electron and a hole are generated between an electron donor and an electron acceptor. The generated hole is transported to a positive electrode through an electron donor layer.

FIG. 1 is a view illustrating an organic electronic device according to an exemplary embodiment of the present specification, the organic electronic device has a structure in which a first electrode 10, a photoactive layer 30, and a second electrode 20 are sequentially stacked, the structure is not limited thereto, and an additional organic material layer may be provided between the first electrode 10 and the second electrode 20.

According to an exemplary embodiment of the present specification, the organic solar cell may further comprise an additional organic material layer. The organic solar cell may reduce the number of organic material layers by using an organic material which simultaneously has various functions.

According to an exemplary embodiment of the present specification, the first electrode is an anode, and the second electrode is a cathode. In another exemplary embodiment, the first electrode is a cathode, and the second electrode is an anode.

According to an exemplary embodiment of the present specification, in the organic solar cell, a cathode, a photoactive layer, and an anode may be arranged in this order, and an anode, a photoactive layer, and a cathode may be arranged in this order, but the arrangement order is not limited thereto.

In another exemplary embodiment, in the organic solar cell, an anode, a hole transport layer, a photoactive layer, an electron transport layer, and a cathode may also be arranged in this order, and a cathode, an electron transport layer, a photoactive layer, a hole transport layer, and an anode may also be arranged in this order, but the arrangement order is not limited thereto.

According to an exemplary embodiment of the present specification, the organic solar cell has a normal structure. In the normal structure, a substrate, an anode, an organic material layer comprising a photoactive layer, and a cathode may be stacked in this order.

According to an exemplary embodiment of the present specification, the organic solar cell has an inverted structure. In the inverted structure, a substrate, a cathode, an organic material layer comprising a photoactive layer, and an anode may be stacked in this order.

According to an exemplary embodiment of the present specification, the organic solar cell has a tandem structure.

The organic solar cell according to an exemplary embodiment of the present specification may have one or two or more photoactive layers. The tandem structure may comprise two or more photoactive layers.

In another exemplary embodiment, a buffer layer may be provided between the photoactive layer and the hole transport layer, or between the photoactive layer and the electron transport layer. In this case, a hole injection layer may be further provided between the anode and the hole transport layer. Further, an electron injection layer may be further provided between the cathode and the electron transport layer.

In the present specification, the substrate may be a glass substrate or a transparent plastic substrate having excellent transparency, surface smoothness, ease of handling, and waterproofing properties, but is not limited thereto, and the substrate is not limited as long as the substrate is typically used in the organic solar cell. Specific examples thereof include glass or polyethylene terephthalate (PET), polyethylene naphthalate (PEN), polypropylene (PP), polyimide (PI), triacetyl cellulose (TAC), and the like, but are not limited thereto.

The anode electrode may be made of a material which is transparent and has excellent conductivity, but is not limited thereto. Examples thereof include: a metal, such as vanadium, chromium, copper, zinc, and gold, or an alloy thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly[3,4-(ethylene-1,2-dioxy)thiophene] (PEDOT), polypyrrole, and polyaniline; and the like, but are not limited thereto.

A method of forming the anode electrode is not particularly limited, but the anode electrode may be formed, for example, by being applied onto one surface of a substrate using a method such as sputtering, e-beam, thermal deposition, spin coating, screen printing, inkjet printing, doctor blade, or gravure printing, or by being coated in the form of a film.

When the anode electrode is formed on a substrate, the anode electrode may be subjected to processes of cleaning, removing moisture, and hydrophilic modification.

For example, a patterned ITO substrate is sequentially cleaned with a cleaning agent, acetone, and isopropyl alcohol (IPA), and then dried on a hot plate at 100° C. to 150° C. for 1 to 30 minutes, preferably at 120° C. for 10 minutes in order to remove moisture, and when the substrate is completely cleaned, the surface of the substrate is hydrophilically modified.

Through the surface modification as described above, the junction surface potential may be maintained at a level suitable for a surface potential of a photoactive layer. Further, during the modification, a polymer thin film may be easily formed on an anode electrode, and the quality of the thin film may also be improved.

Examples of a pre-treatment technology for an anode electrode comprise a) a surface oxidation method using a parallel flat plate-type discharge, b) a method of oxidizing a surface through ozone produced by using UV rays in a vacuum state, c) an oxidation method using oxygen radicals produced by plasma, and the like.

One of the methods may be selected depending on the state of the anode electrode or the substrate. However, commonly in all the methods, it is preferred to prevent oxygen from being separated from the surface of the anode electrode or the substrate, and maximally inhibit moisture and organic materials from remaining. In this case, it is possible to maximize a substantial effect of the pre-treatment.

As a specific example, it is possible to use a method of oxidizing the surface through ozone produced by using UV. In this case, a patterned ITO substrate after being ultrasonically cleaned is baked on a hot plate and dried well, and then introduced into a chamber, and the patterned ITO substrate may be cleaned by ozone generated by allowing an oxygen gas to react with UV light by operating a UV lamp.

However, the surface modification method of the patterned ITO substrate in the present specification need not be particularly limited, and any method may be used as long as the method is a method of oxidizing a substrate.

The cathode electrode may be a metal having a low work function, but is not limited thereto. Specific examples thereof include: a metal such as magnesium, calcium, sodium, potassium, titanium, indium, yttrium, lithium, gadolinium, aluminum, silver, tin, and lead, or an alloy thereof; and a multi-layer structured material such as LiF/Al, $LiO_2$/Al, LiF/Fe, Al:Li, Al:$BaF_2$, and Al:$BaF_2$:Ba, but are not limited thereto.

The cathode electrode may be deposited and formed in a thermal evaporator showing a vacuum degree of $5 \times 10^{-7}$ torr or less, but the forming method is not limited to this method.

A material for the hole transport layer and/or a material for the electron transport layer serve to efficiently transfer electrons and holes separated from a photoactive layer to an electrode, and the materials are not particularly limited.

The material for the hole transport layer may be poly(3,4-ethylenedioxythiophene) doped with poly(styrenesulfonic acid) (PEDOT:PSS) and molybdenum oxide ($MoO_x$); vanadium oxide ($V_2O_5$); nickel oxide (NiO); tungsten oxide ($WO_x$); and the like, but is not limited thereto.

The material for the electron transport layer may be electron-extracting metal oxides, and specific examples thereof include: metal complexes of 8-hydroxyquinoline; complexes including $Alq_3$; metal complexes including Liq; LiF; Ca; titanium oxide ($TiO_x$); zinc oxide (ZnO); cesium carbonate ($Cs_2CO_3$); and the like, but are not limited thereto.

The photoactive layer may be formed from the composition for an organic electronic device by a method such as spin coating, dip coating, screen printing, spray coating, doctor blade, brush painting, roll-to-roll printing, inkjet printing, nozzle printing, offset printing, transfer printing or screen printing, but the forming method is not limited thereto.

A solution process is suitable for the composition for an organic electronic device according to an exemplary embodiment of the present specification due to the structural characteristics, so that there is an effect in that the composition is economically feasible in terms of time and cost when a device is manufactured.

Further, since the composition for an organic electronic device comprises the heterocyclic compound of Formula 1, the photoactive layer has an effect of having constantly excellent photoelectric conversion efficiency within a thickness range of 50 nm to 150 nm.

According to an exemplary embodiment of the present specification, the photoactive layer has a thickness of 50 nm to 150 nm, specifically, 100 nm to 150 nm.

In an exemplary embodiment of the present specification, the organic electronic device may be an organic transistor.

An exemplary embodiment of the present specification provides an organic transistor comprising a source, a drain, a gate, and an organic material layer having one or more layers, in which one or more layers of the organic material layer comprise the heterocyclic compound.

According to an exemplary embodiment of the present specification, the organic material layer comprises an n-type semiconductor layer and a p-type semiconductor layer, and the n-type semiconductor layer comprises the heterocyclic compound.

A preparation method of the heterocyclic compound and the manufacture of an organic electronic device comprising the same will be described in detail in the following Preparation Examples and Examples. However, the following Examples are provided for exemplifying the present specification, and the scope of the present specification is not limited thereby.

<Preparation Example 1> Preparation of Compound 1

1) Preparation of Compound A-1

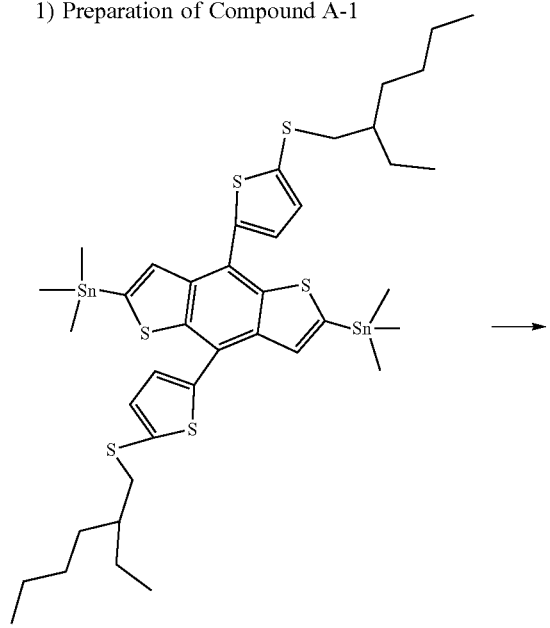

(4,8-bis(5-((2-ethylhexyl)thio)thiophen-2-yl)benzo[1,2-b:4,5-b']dithiophene-2,6-diyl(bis)trimethylstannane)

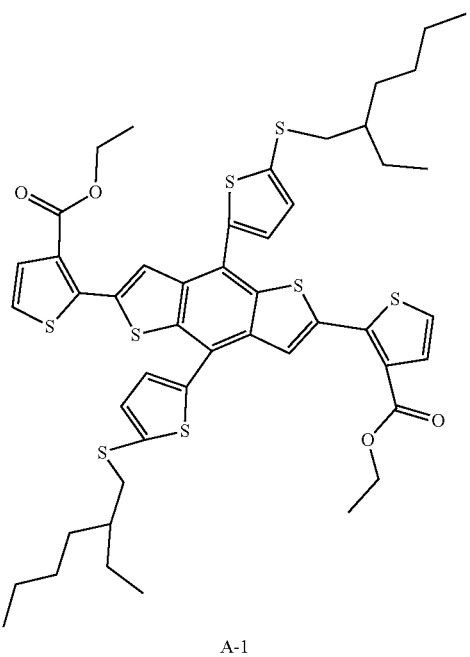

A-1

After 6 g of (4,8-bis(5-((2-ethylhexyl)thio)thiophen-2-yl)benzo[1,2-b':4,5-b']dithiophene-2,6-diyl)bis(trimethylstannane), 3.28 g (2.5 eq) of ethyl 2-bromo-thiophene-3-carboxylate, 0.27 g (0.05 eq) of tris(dibenzylideneacetone)dipalladium(0) (Pd$_2$(dba)$_3$), and 0.30 g (0.1 eq) of tri(o-tolyl)phosphine were dissolved in toluene in a round flask equipped with a condenser, the resulting solution was refluxed for 12 hours. After the reaction was terminated with dichloromethane and a product was extracted with distilled water, the product was purified with column chromatography to obtain Compound A-1.

2) Preparation of Compound A-2

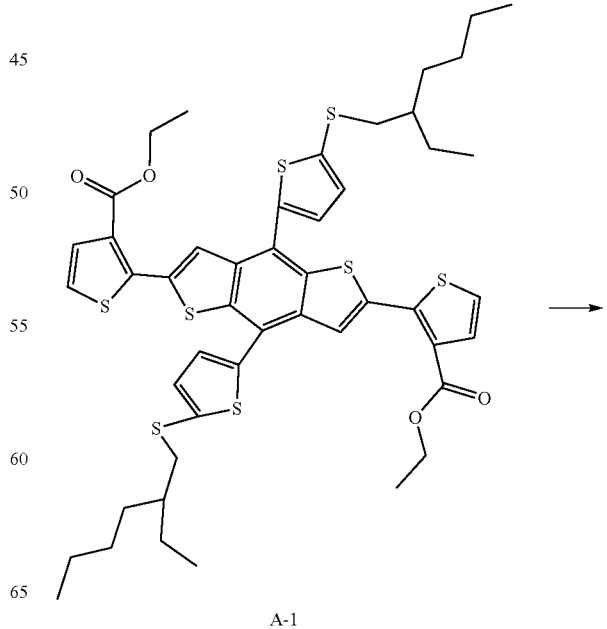

A-1

-continued

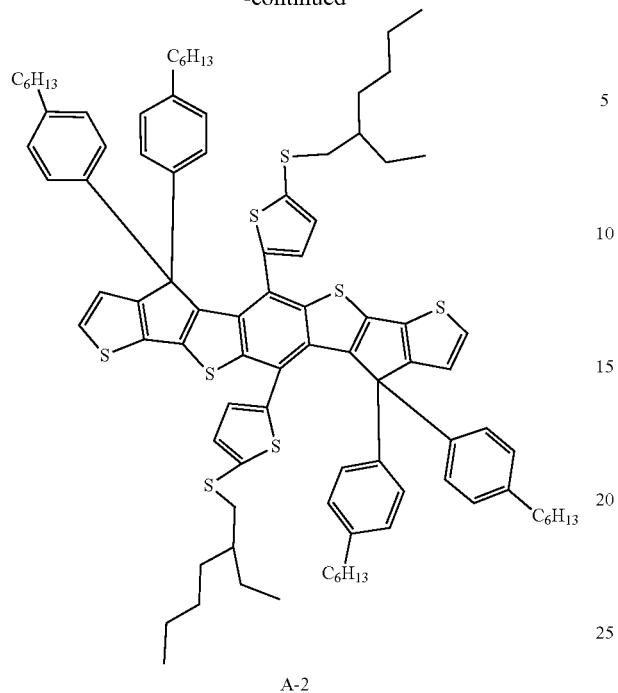

A-2

After 7.28 g (5.3 eq) of 1-bromo-4-hexylbenzene was dissolved in tetrahydrofuran in a round flask, 12.08 mL (1.0 eq) of n-butyllithium was slowly injected thereto at −78° C., and the resulting mixture was stirred at the same temperature for 1 hour. Thereafter, Compound A-1 (5.3 g) was dissolved in tetrahydrofuran and the resulting solution was slowly injected thereto. After the mixture was stirred at room temperature for 12 hours, the reaction was terminated with distilled water, a product was extracted with dichloromethane and purified with column chromatography, and then the product was refluxed under a condition of acetic acid/HCl (40 mL/0.5 mL) for 4 hours to obtain Compound A-2.

3) Preparation of Compound A-3

-continued

A-3

After Compound A-2 (2.6 g) was dissolved in tetrahydrofuran in a round flask, 2.0 mL (2.5 eq) of n-butyllithium was slowly injected thereto at −78° C., and the resulting mixture was stirred at the same temperature for 1 hour. Thereafter, 0.39 mL of dimethylformamide was slowly injected thereinto. After the mixture was stirred at room temperature for 12 hours, the reaction was terminated with distilled water, and the resulting product was purified with column chromatography to obtain Compound A-3.

4) Preparation of Compound 1

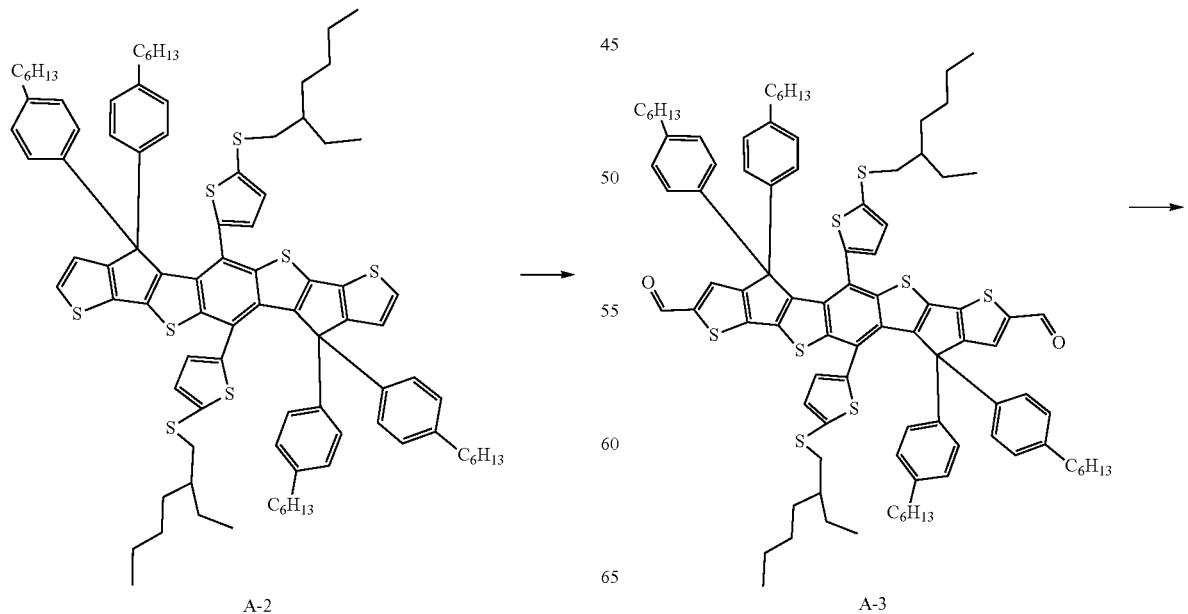

A-2 → A-3 →

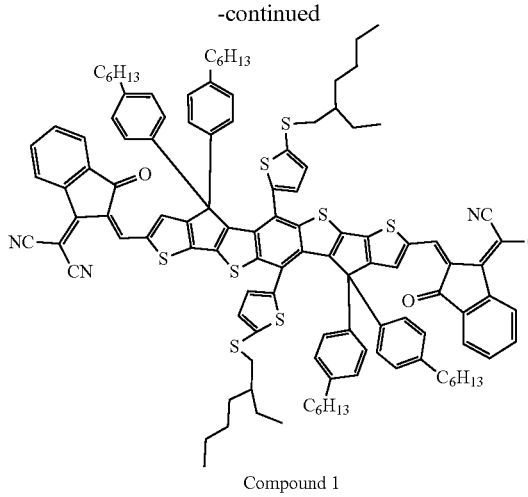

Compound 1

After Compound A-3 (0.4 g) and 0.2 g (5 eq) of 2-(3-oxo-2,3-dihydro-1H-inden-1-ylidene)malononitrile were dissolved in chloroform in a round flask equipped with a condenser, 1 mL of pyridine was injected thereto, and the resulting mixture was refluxed at 65° C. After 12 hours, a solid produced by methanol was purified with column chromatography to obtain Compound 1.

Figure 2:
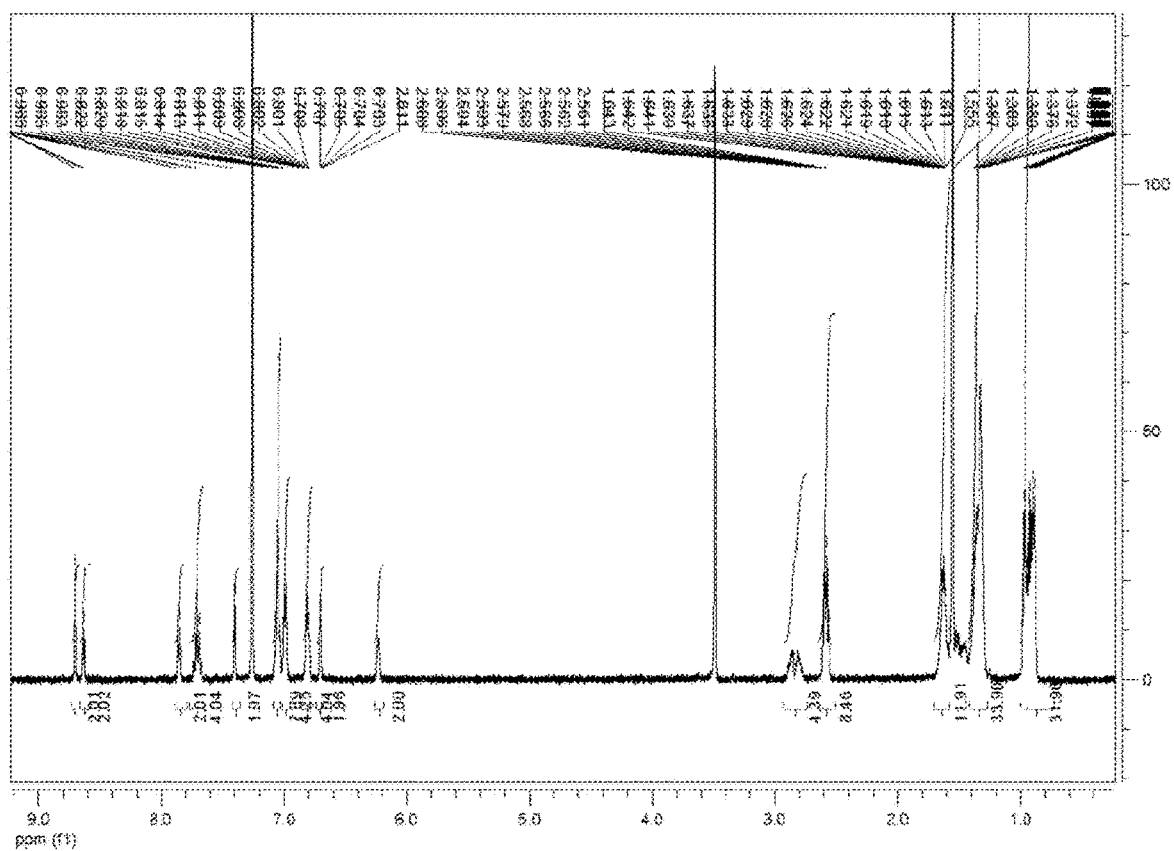
FIG. 2 is a view illustrating NMR data of Compound 1 according to an exemplary embodiment of the present specification.

FIG. 2 is a view illustrating NMR data of Compound 1.

<Preparation Examples 2 to 5> Preparation of Compounds 2 to 5

The following Compounds 2 to 5 were prepared in the same manner as in Preparation Example 1, except that the respective materials in the following Table 1 were used instead of 2-(3-oxo-2,3-dihydro-1H-inden-1-ylidene)malononitrile in 4) of Preparation Example 1.

TABLE 1

| Target compound | Used material |
|---|---|
| Compound 2 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |
| Compound 3 | 2-(5,6-difluoro-3-oxo-2,3-dihydro-1H-inden-1-ylidene)malononitrile |
| Compound 4 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 5 | 2-(5,6-dimethyl-3-oxo-2,3-dihydro-1H-inden-1-ylidene)malononitrile |

[Compound 2]

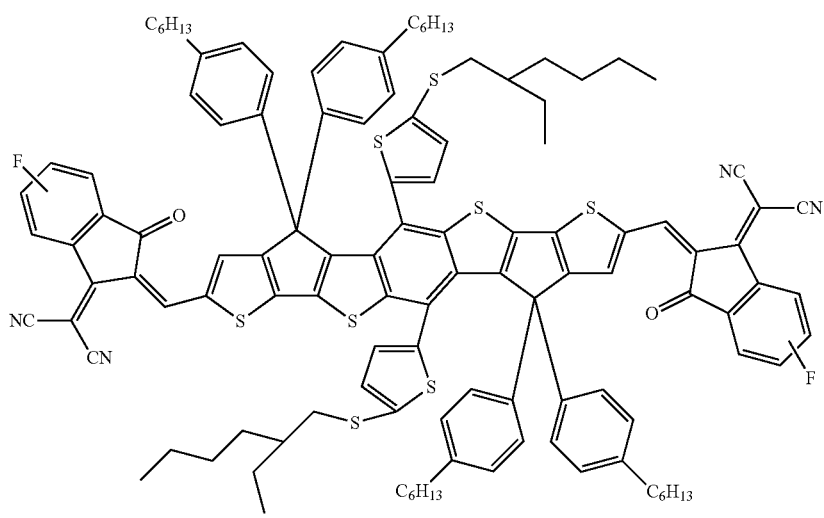

Figure 3:
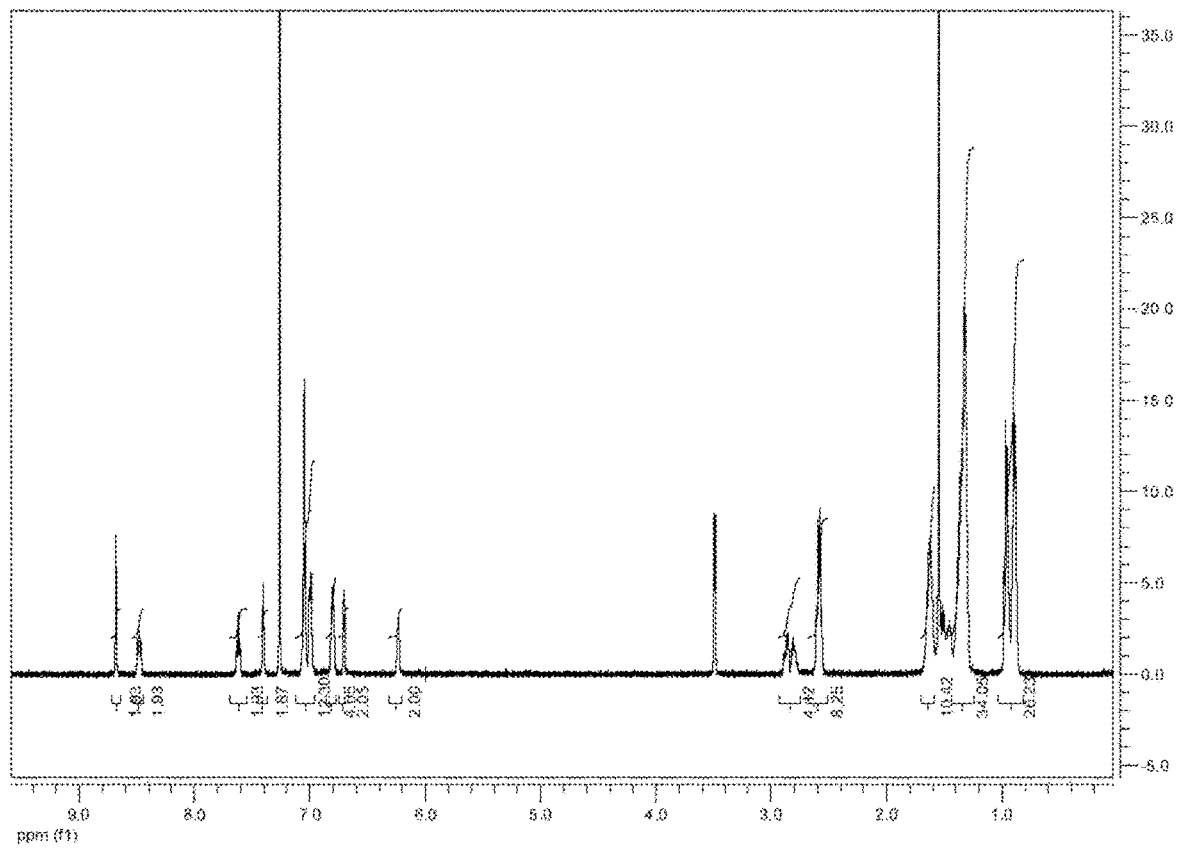
FIG. 3 is a view illustrating NMR data of Compound 3 according to an exemplary embodiment of the present specification.
Figure 4:
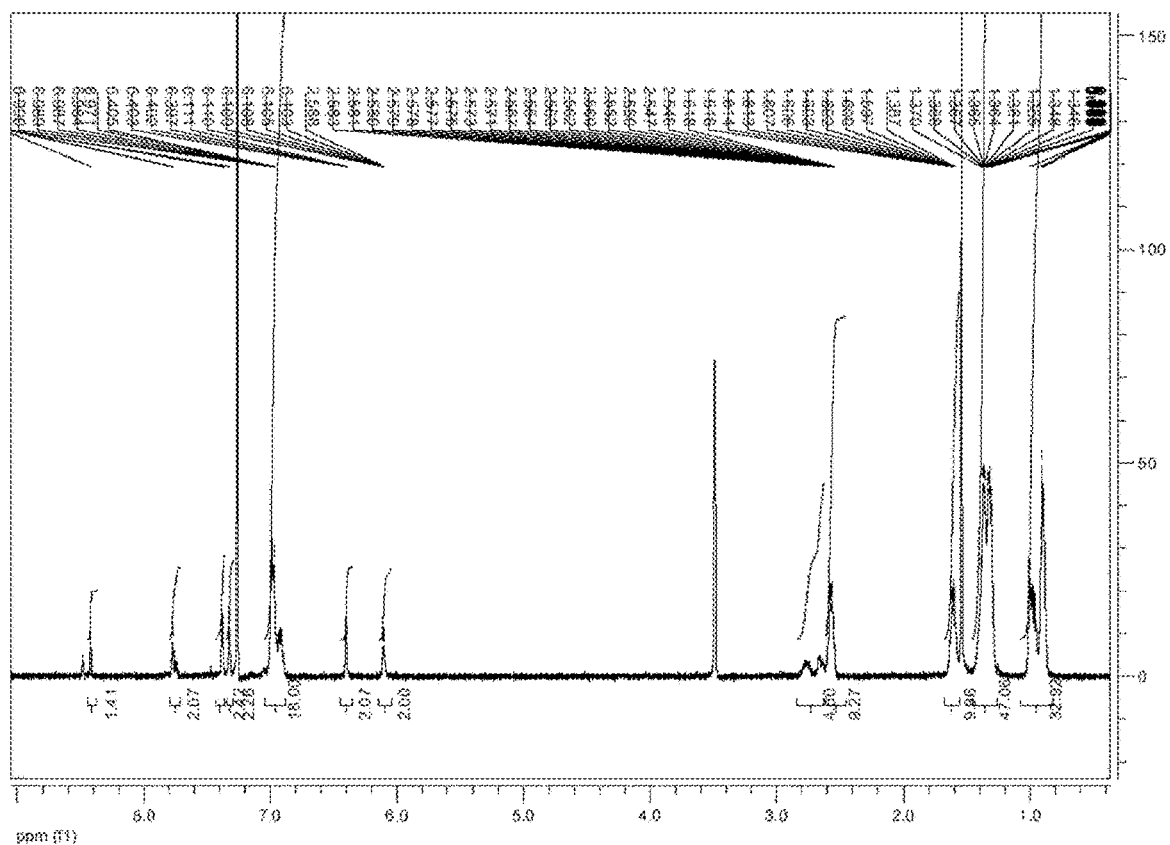
FIG. 4 is a view illustrating NMR data of Compound 6 according to an exemplary embodiment of the present specification.

[Compound 3]
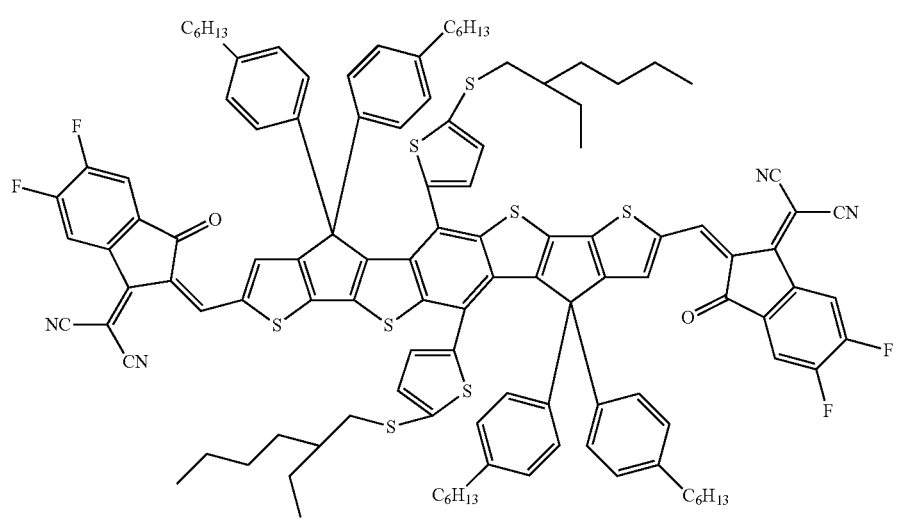
[Compound 4]
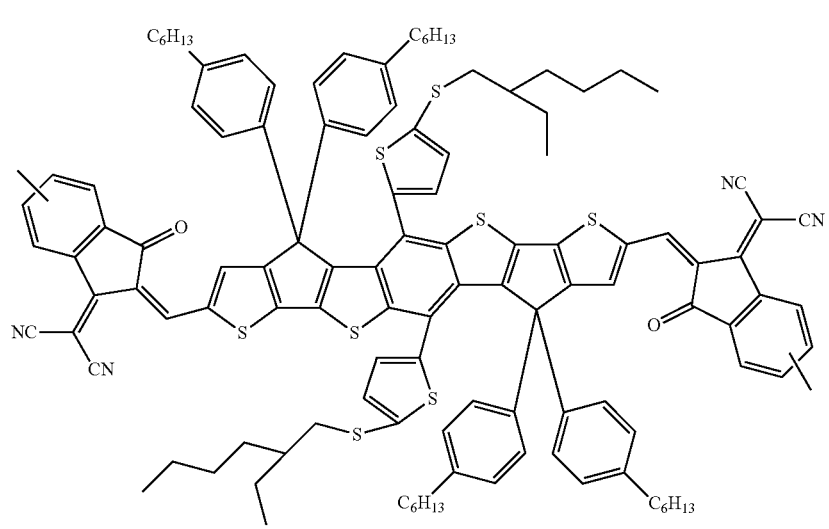
[Compound 5]
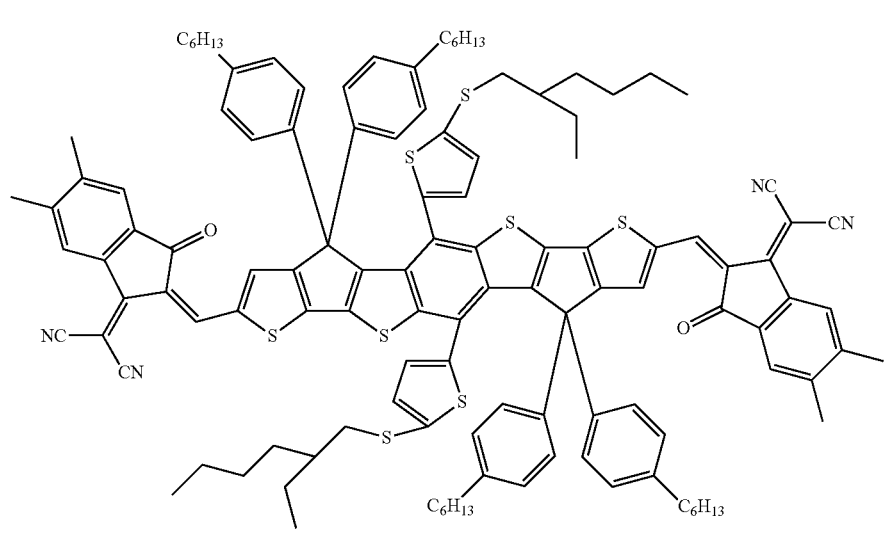
FIG. 3 is a view illustrating NMR data of Compound 3.

<Preparation Example 6> Preparation of Compound 6
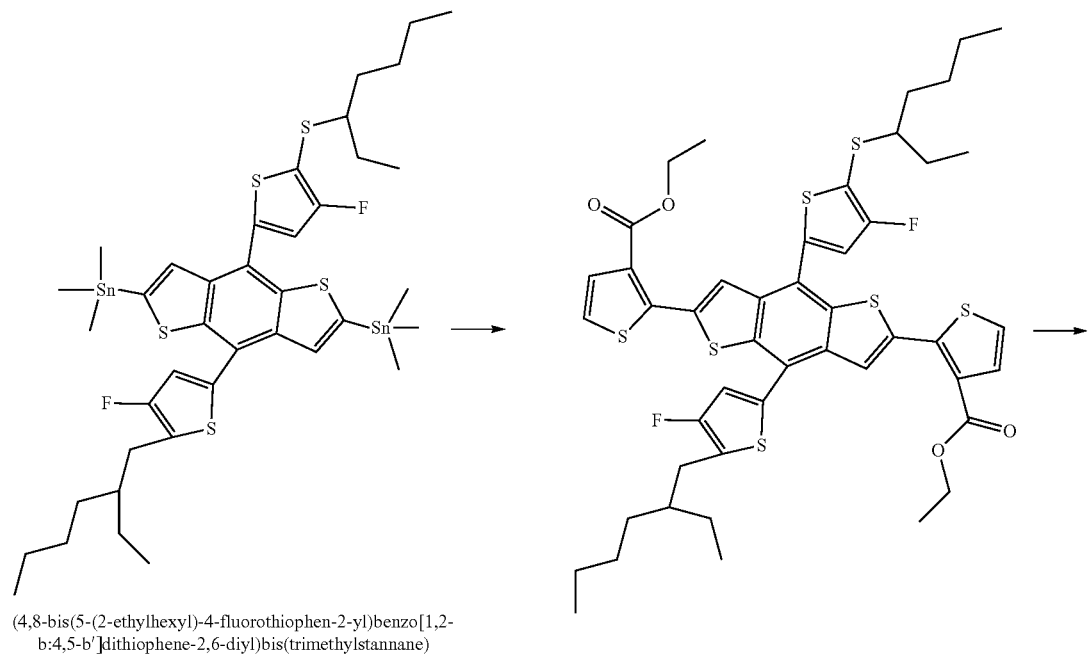
(4,8-bis(5-(2-ethylhexyl)-4-fluorothiophen-2-yl)benzo[1,2-b:4,5-b']dithiophene-2,6-diyl)bis(trimethylstannane)
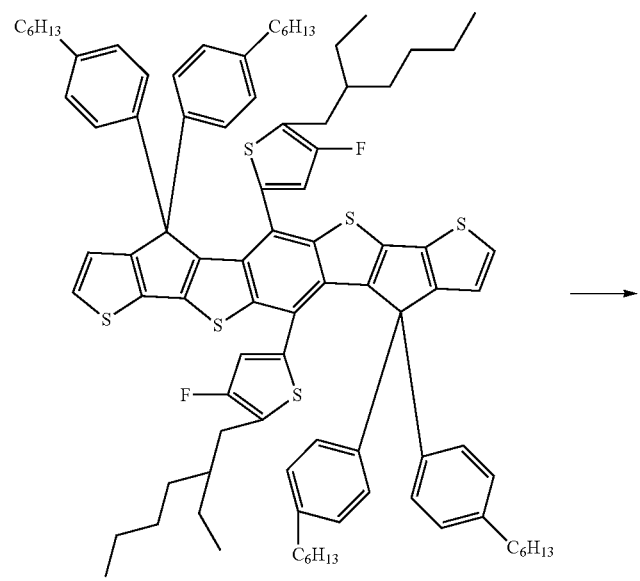

-continued

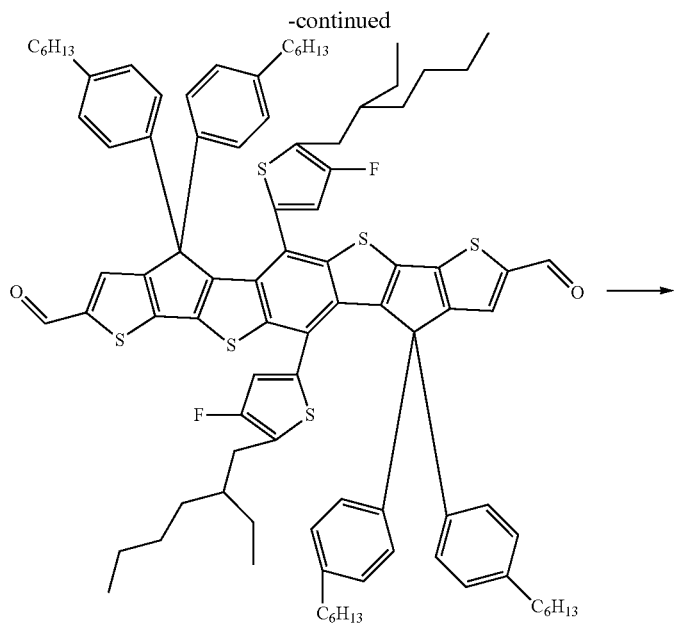

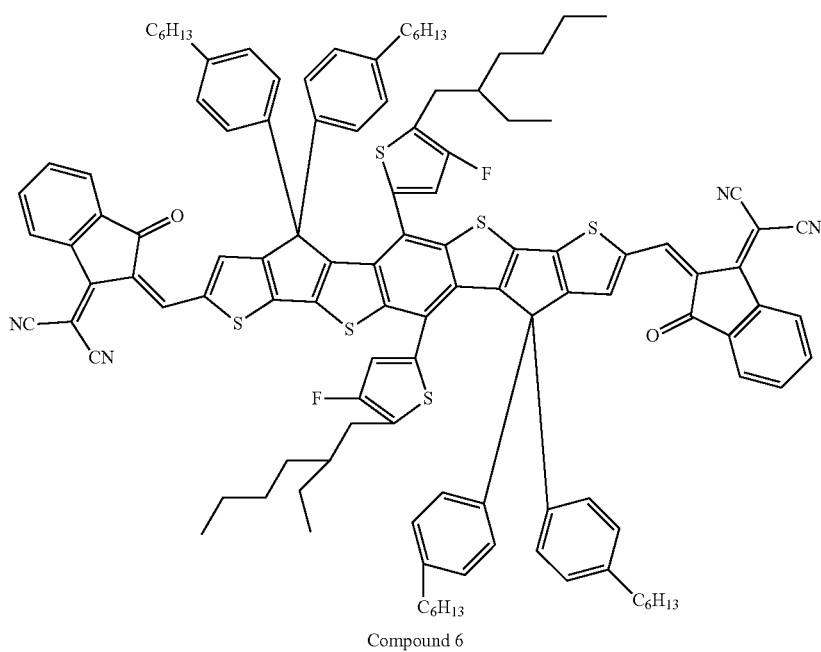

Compound 6

Compound 6 was prepared in the same manner as in Preparation Example 1, except that 4,8-bis(5-(2-ethylhexyl)-4-fluorothiophen-2-yl)benzo[1,2-b':4,5-b']dithiophene-2,6-diyl)bis(trimethylstannane) was used instead of 4,8-bis(5-((2-ethylhexyl)thio)thiophen-2-yl)benzo[1,2-b':4,5-b']dithiophene-2,6-diyl)bis(trimethylstannane) in 1) of Preparation Example 1.

<Preparation Examples 7 to 10> Preparation of Compounds 7 to 10

The following Compounds 7 to 10 were prepared in the same manner as in Preparation Example 6, except that the respective materials in the following Table 2 were used instead of 2-(3-oxo-2,3-dihydro-1H-inden-1-ylidene)malononitrile in Preparation Example 6.

TABLE 2

| Target compound | Used material |
| --- | --- |
| Compound 7 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |
| Compound 8 | 2-(5,6-difluoro-3-oxo-2,3-dihydro-1H-inden-1-ylidene)malononitrile |
| Compound 9 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 10 | 2-(5,6-dimethyl-3-oxo-2,3-dihydro-1H-inden-1-ylidene)malononitrile |

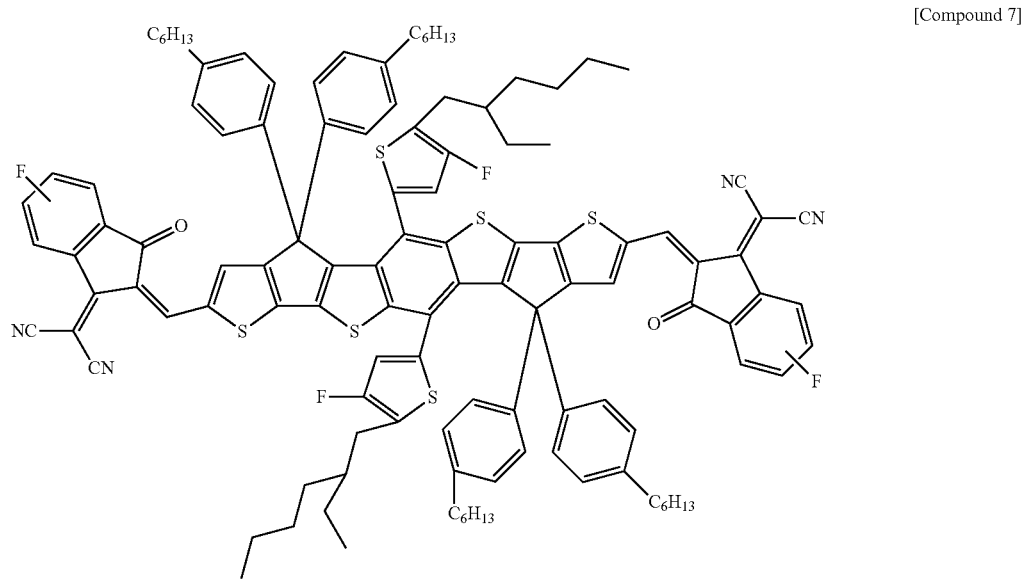

[Compound 7]

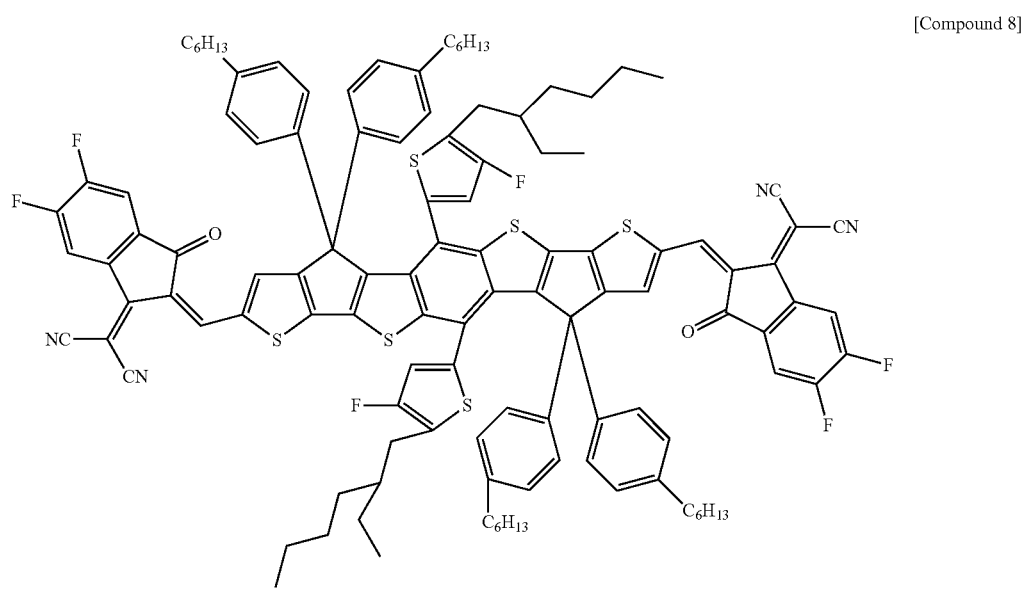

[Compound 8]

-continued

[Compound 9]

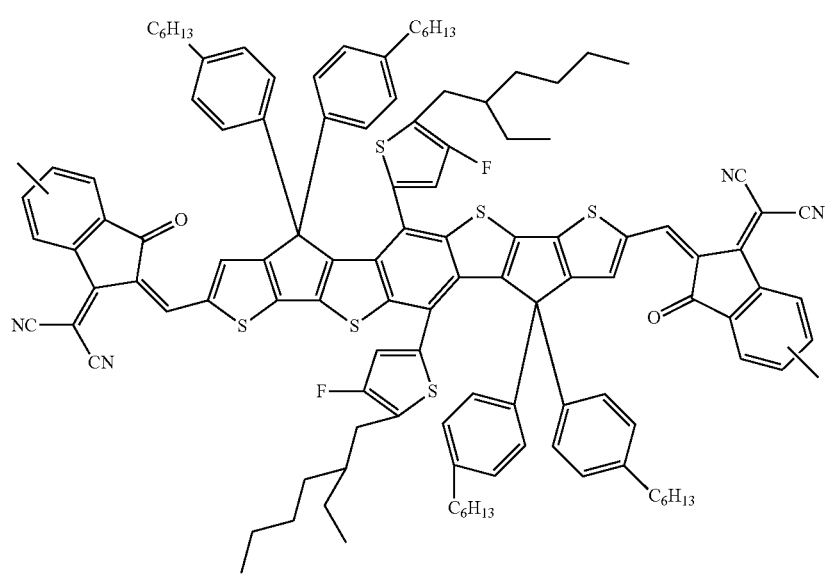

[Compound 10]

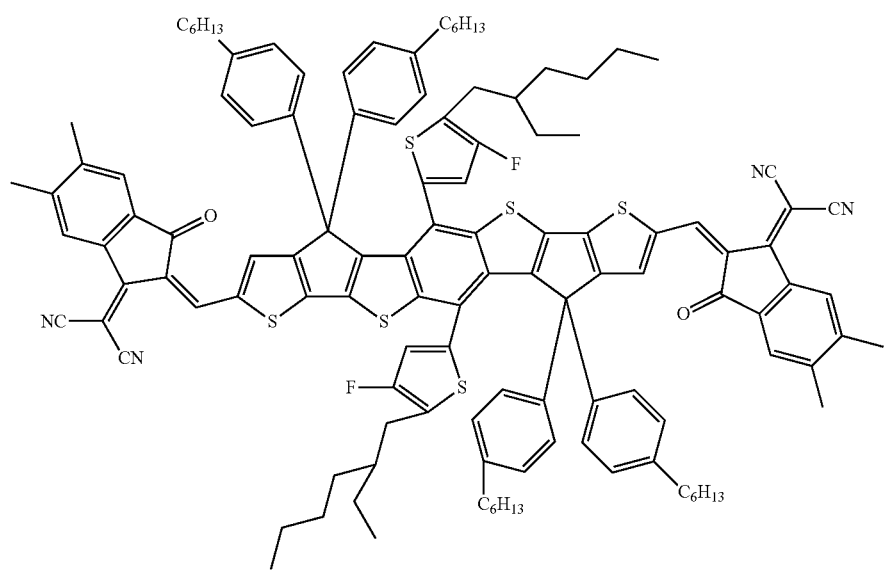

Figure 5:
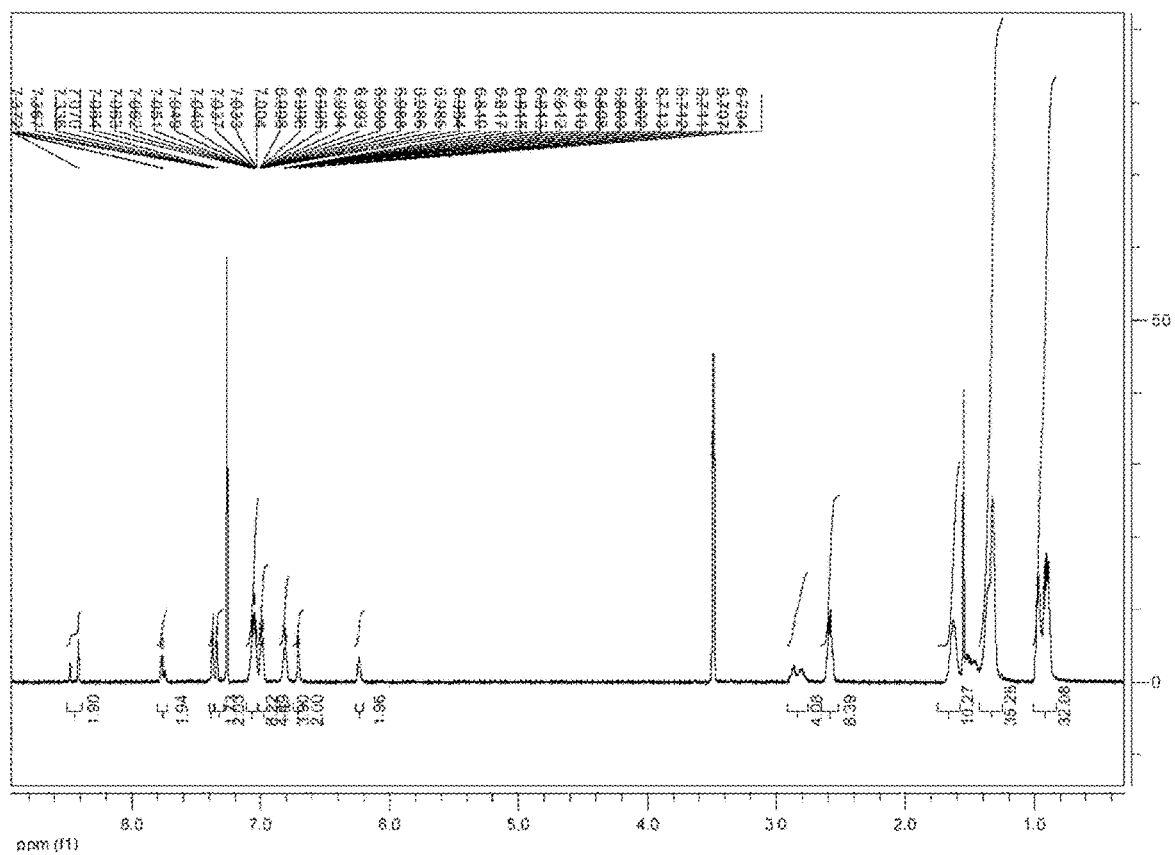
FIG. 5 is a view illustrating NMR data of Compound 8 according to an exemplary embodiment of the present specification.

FIG. 5 is a view illustrating NMR data of Compound 8.

Figure 6:
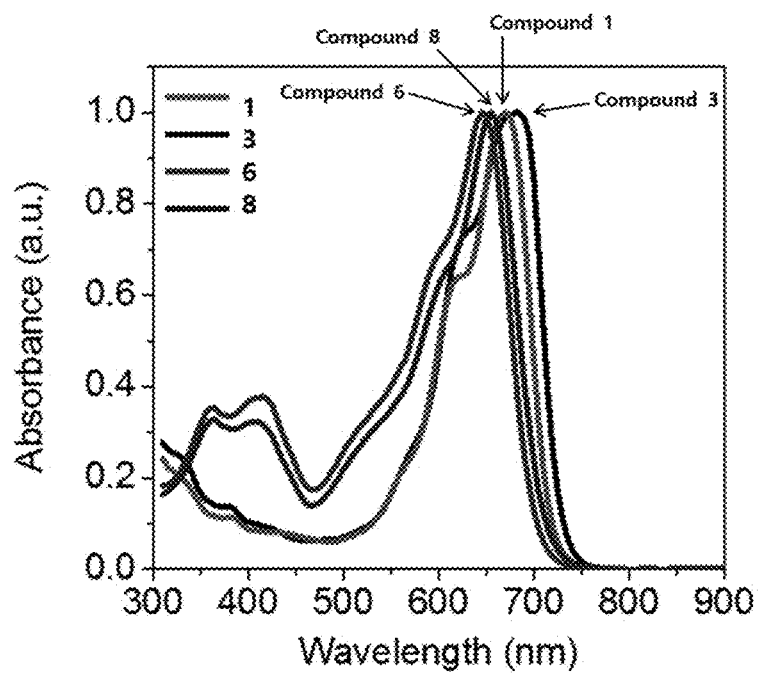
FIG. 6 is a view illustrating UV-vis absorption spectra of Compounds 1, 3, 6, and 8 in a solution state according to an exemplary embodiment of the present specification.
Figure 7:
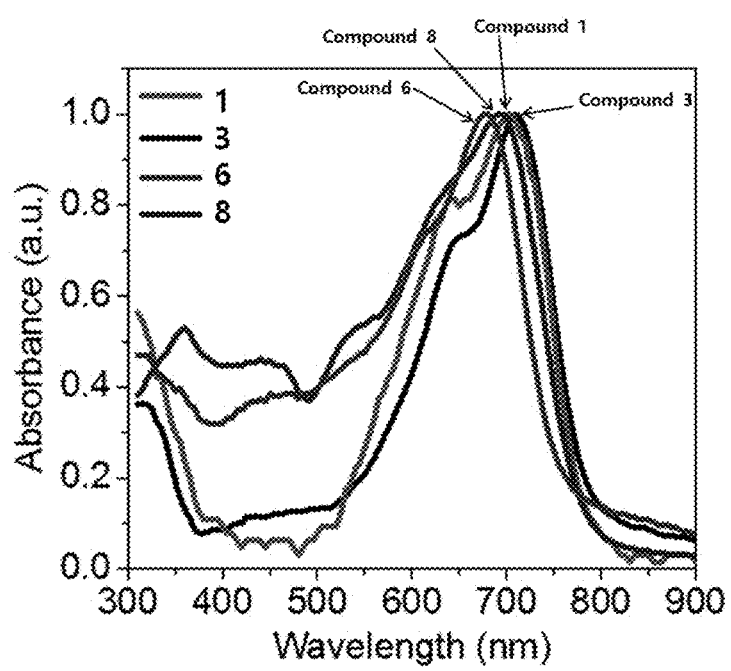
FIG. 7 is a view illustrating UV-vis absorption spectra of Compounds 1, 3, 6, and 8 in a film state according to an exemplary embodiment of the present specification.

FIG. 6 is a view illustrating UV-vis absorption spectra of Compounds 1, 3, 6, and 8 in a solution state, and FIG. 7 is a view illustrating UV-vis absorption spectra of Compounds 1, 3, 6, and 8 in a film state.

Specifically, FIG. 6 illustrates data obtained by measuring the UV-vis absorption spectrum after each of Compounds 1, 3, 6, and 8 was dissolved in chlorobenzene, and FIG. 7 illustrates data obtained by measuring the UV-vis absorption spectrum after each of Compounds 1, 3, 6, and 8 was dissolved in chlorobenzene and prepared as a film by a spin-coating method.

<Preparation Example 11> Preparation of Compound 11
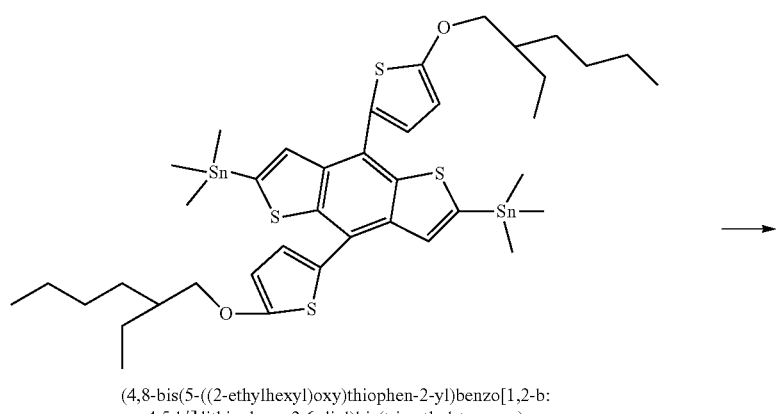
(4,8-bis(5-((2-ethylhexyl)oxy)thiophen-2-yl)benzo[1,2-b: 4,5-b']dithiophene-2,6-diyl)bis(trimethylstannane)
→
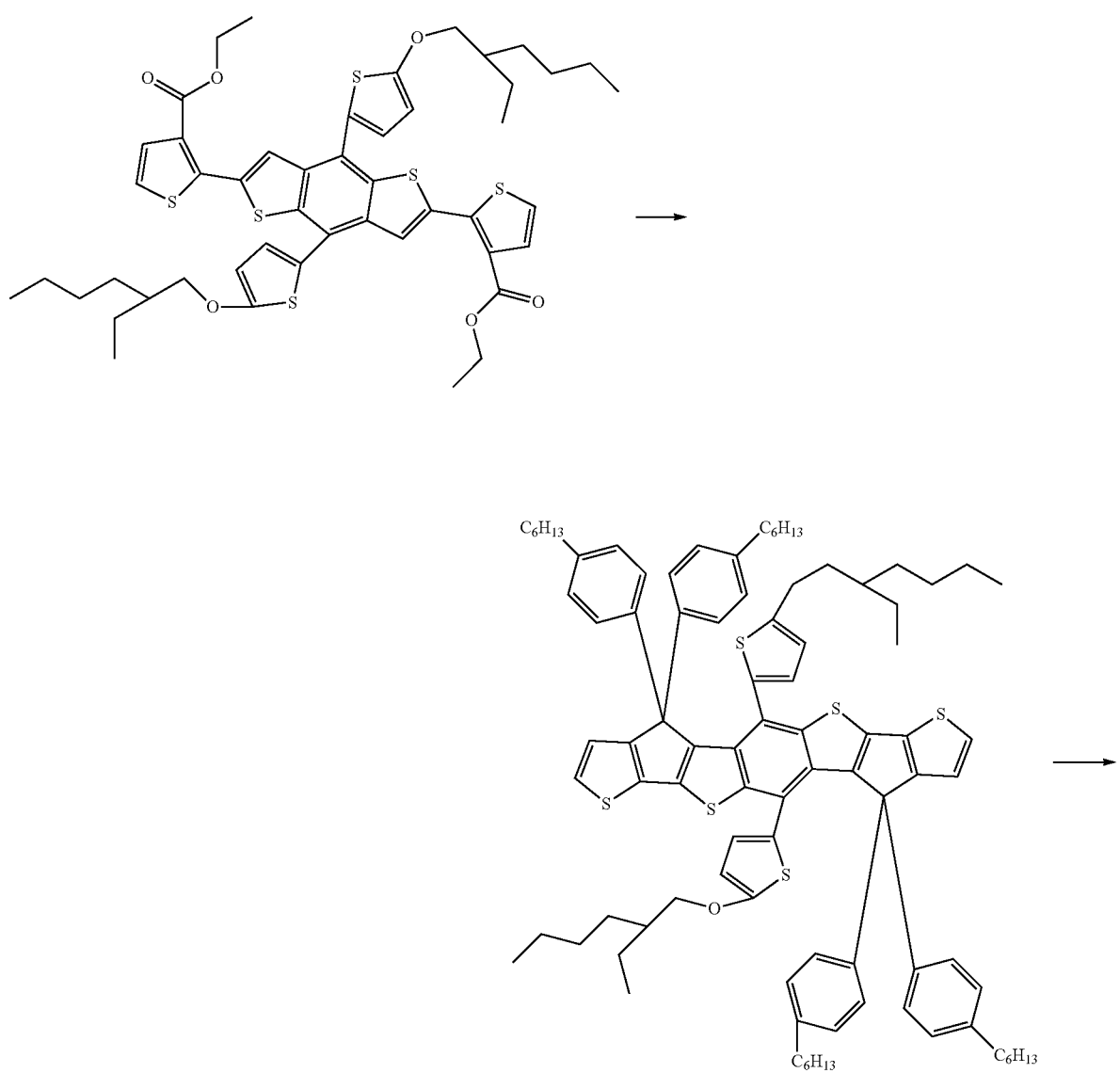
→

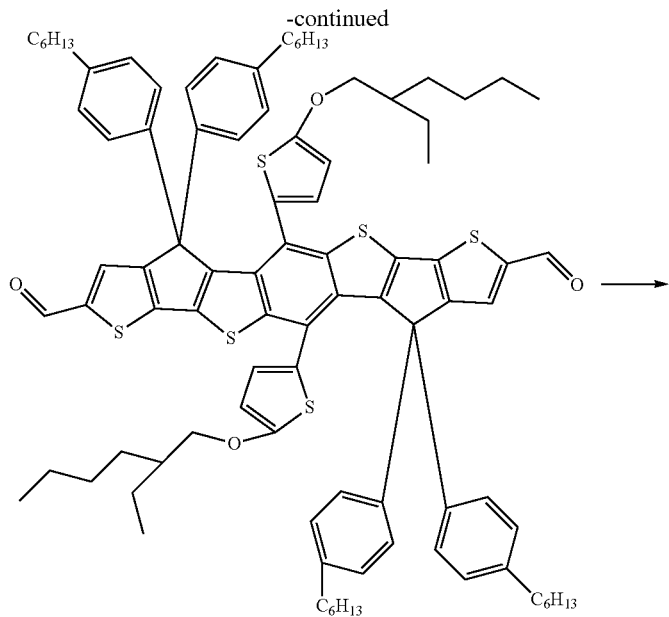

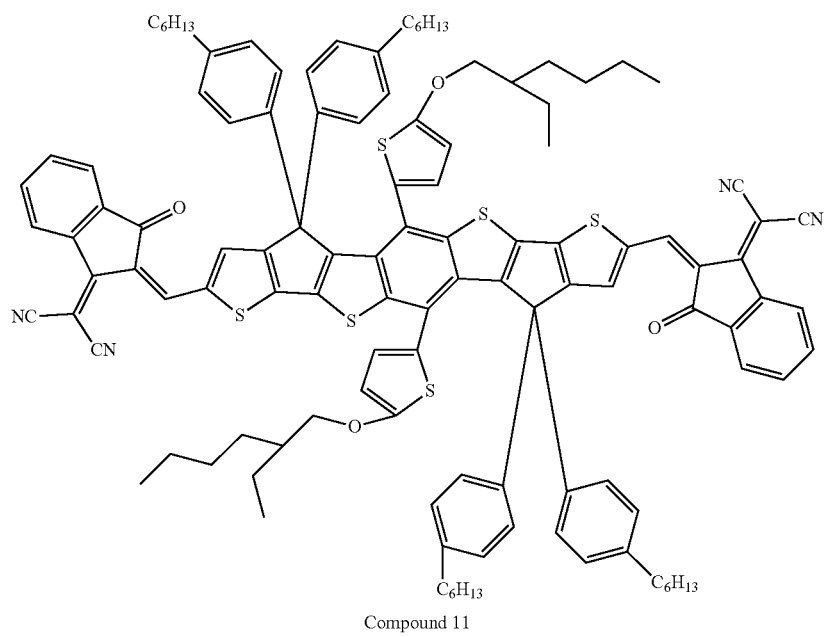

Compound 11

Compound 11 was prepared in the same manner as in Preparation Example 1, except that in 4,8-bis(5-((2-ethylhexyl)oxy)thiophen-2-yl)benzo[1,2-b':4,5-b]dithiophene-2,6-diyl)bis(trimethylstannane) was used instead of 4,8-bis(5-((2-ethylhexyl)thio)thiophen-2-yl)benzo[1,2-b':4,5-b']dithiophene-2,6-diyl)bis(trimethylstannane) in Preparation Example 1.

<Preparation Examples 12 to 15> Preparation of Compounds 12 to 15

The following Compounds 12 to 15 were prepared in the same manner as in Preparation Example 11, except that the respective materials in the following Table 3 were used instead of 2-(3-oxo-2,3-dihydro-1H-inden-1-ylidene)malononitrile in Preparation Example 11.

TABLE 3

| Target compound | Used material |
|---|---|
| Compound 12 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |
| Compound 13 | 2-(5,6-difluoro-3-oxo-2,3-dihydro-1H-inden-1-ylidene)malononitrile |
| Compound 14 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 15 | 2-(5,6-dimethyl-3-oxo-2,3-dihydro-1H-inden-1-ylidene)malononitrile |

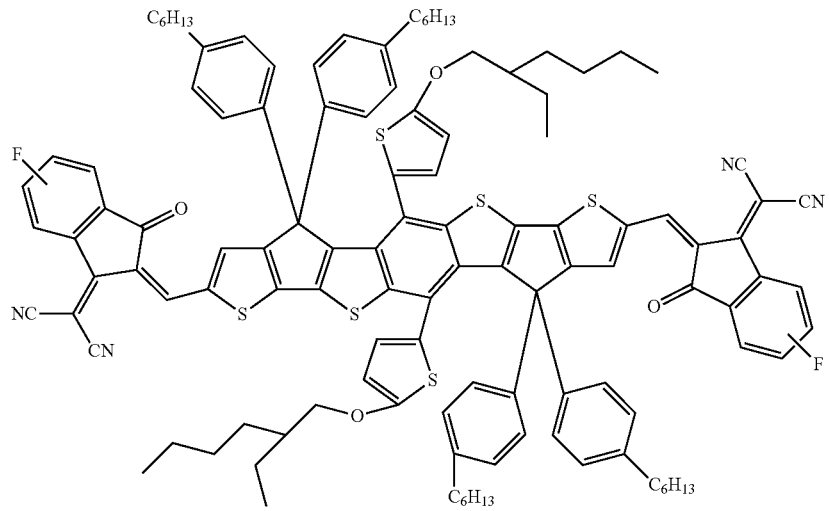

[Compound 12]

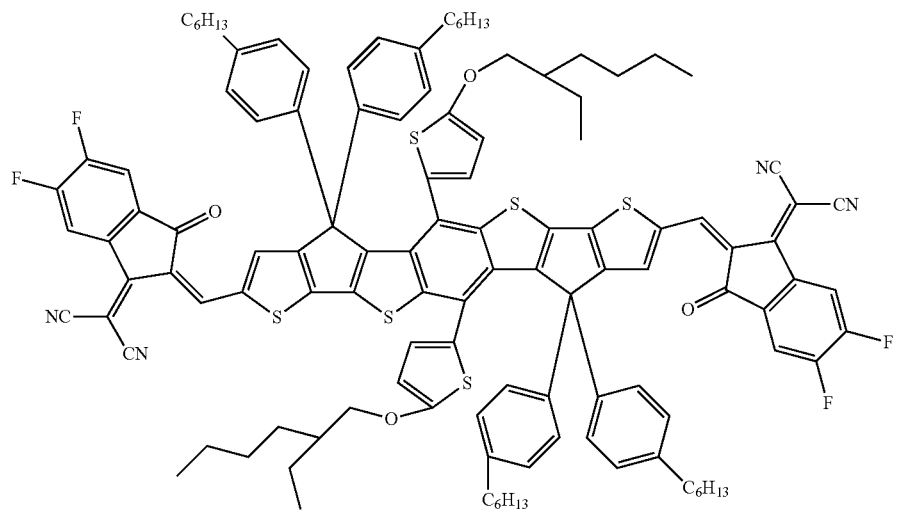

[Compound 13]

[Compound 14]
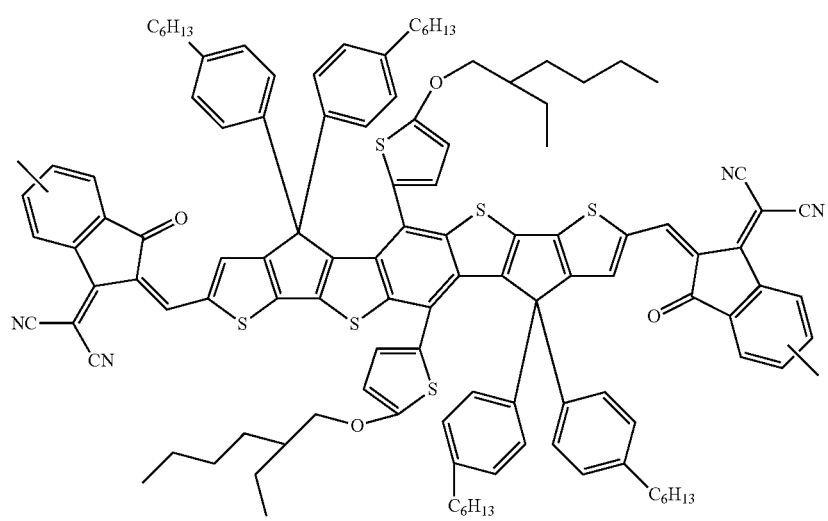
[Compound 15]
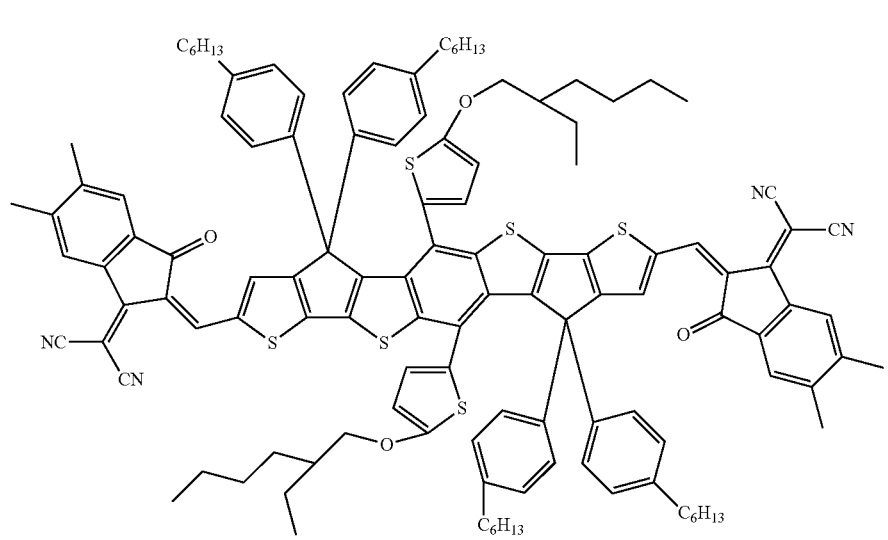
<Preparation Example 16> Preparation of Compound 16
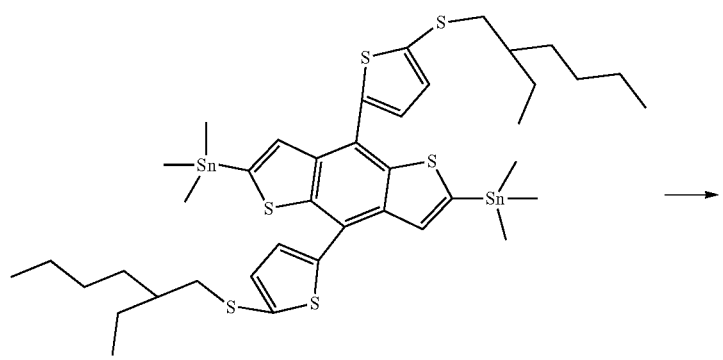

-continued
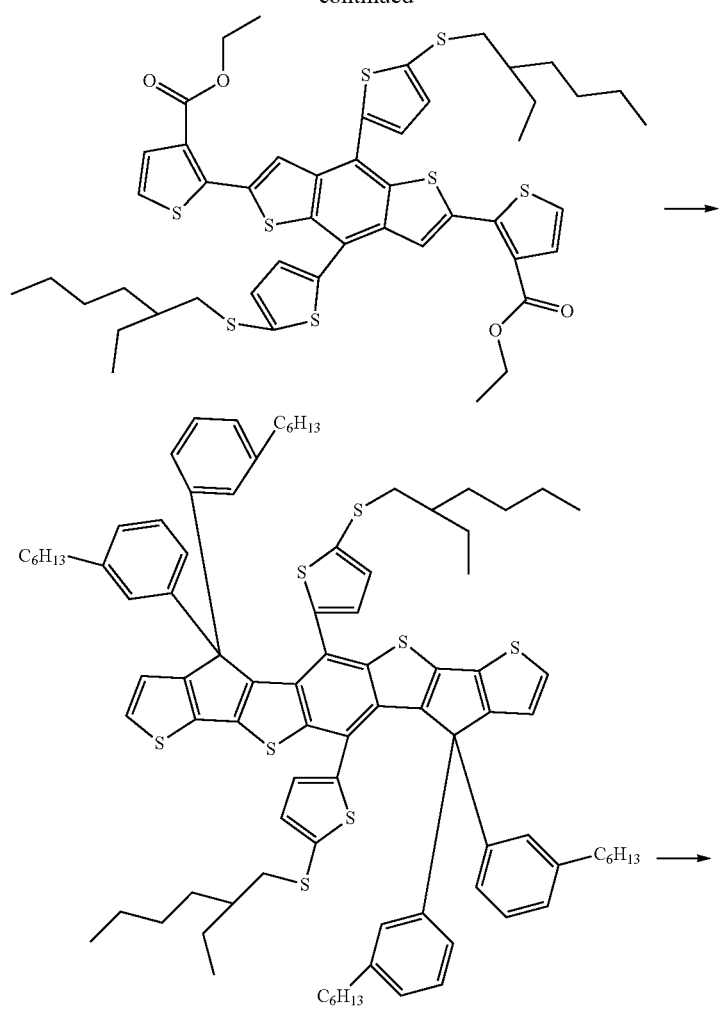
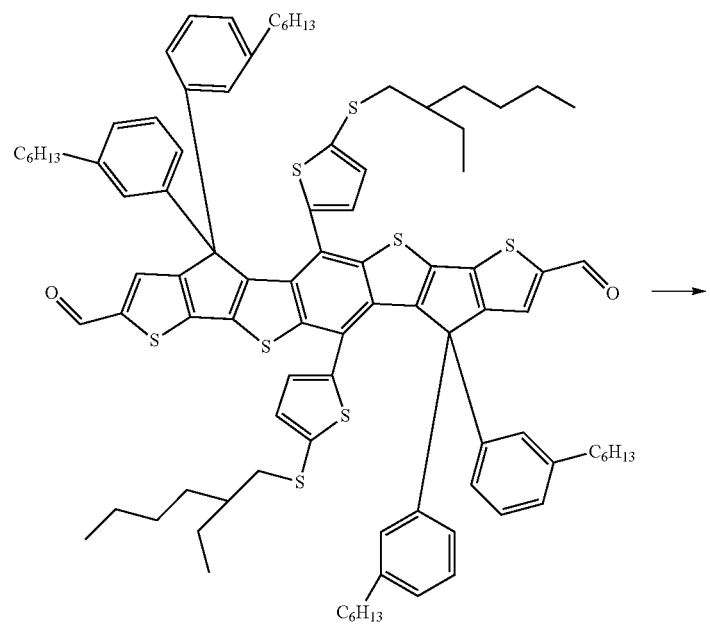

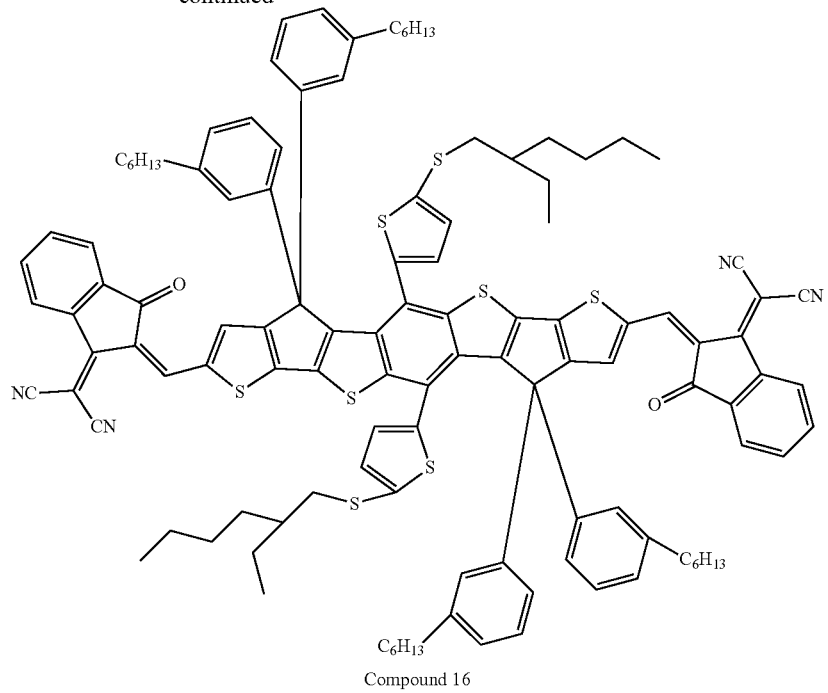

Compound 16

Compound 16 was prepared in the same manner as in Preparation Example 1, except that 3-bromo-4-hexylbenzene was used instead of 1-bromo-4-hexylbenzene in Preparation Example 1.

<Preparation Examples 17 to 20> Preparation of Compounds 17 to 20

The following Compounds 17 to 20 were prepared in the same manner as in Preparation Example 16, except that the respective materials in the following Table 4 were used instead of 2-(3-oxo-2,3-dihydro-1H-inden-1-ylidene)malononitrile in Preparation Example 16.

TABLE 4

| Target compound | Used material |
| --- | --- |
| Compound 17 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |
| Compound 18 | 2-(5,6-difluoro-3-oxo-2,3-dihydro-1H-inden-1-ylidene)malononitrile |
| Compound 19 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 20 | 2-(5,6-dimethyl-3-oxo-2,3-dihydro-1H-inden-1-ylidene)malononitrile |

[Compound 17]
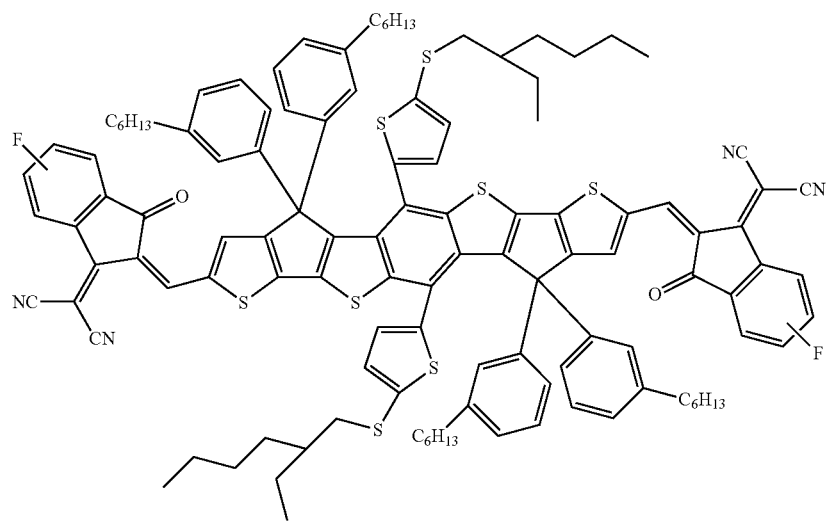
[Compound 18]
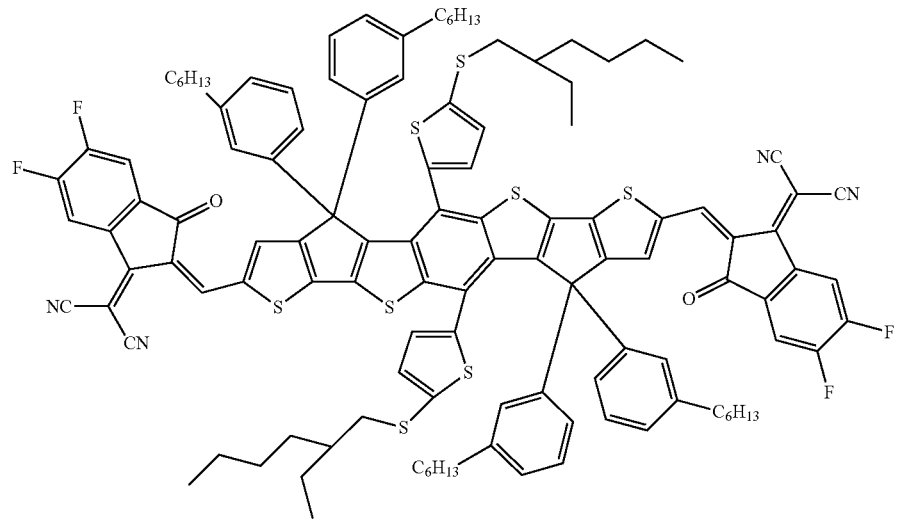
[Compound 19]
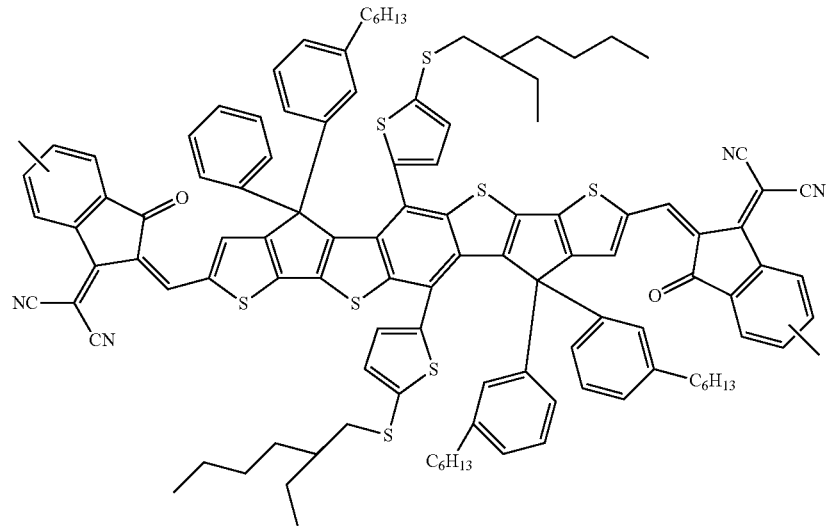

[Compound 20]
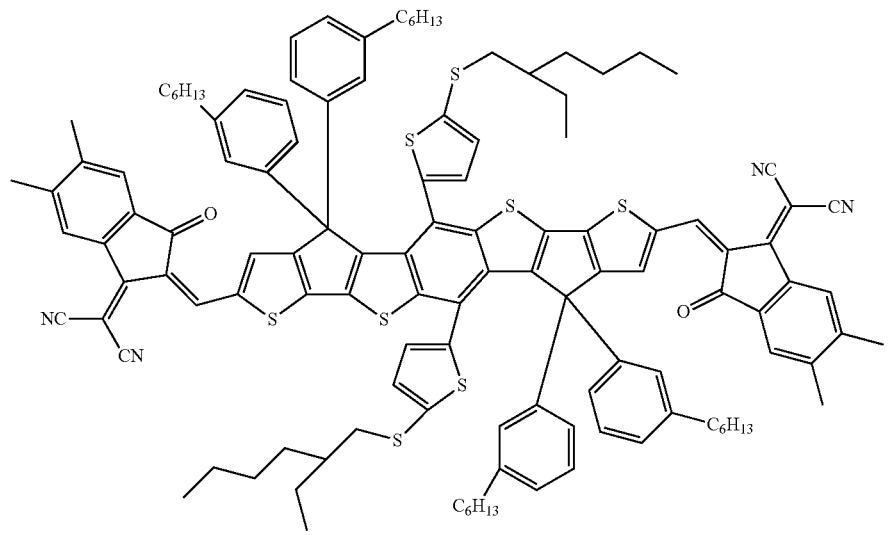
<Preparation Example 21> Preparation of Compound 21
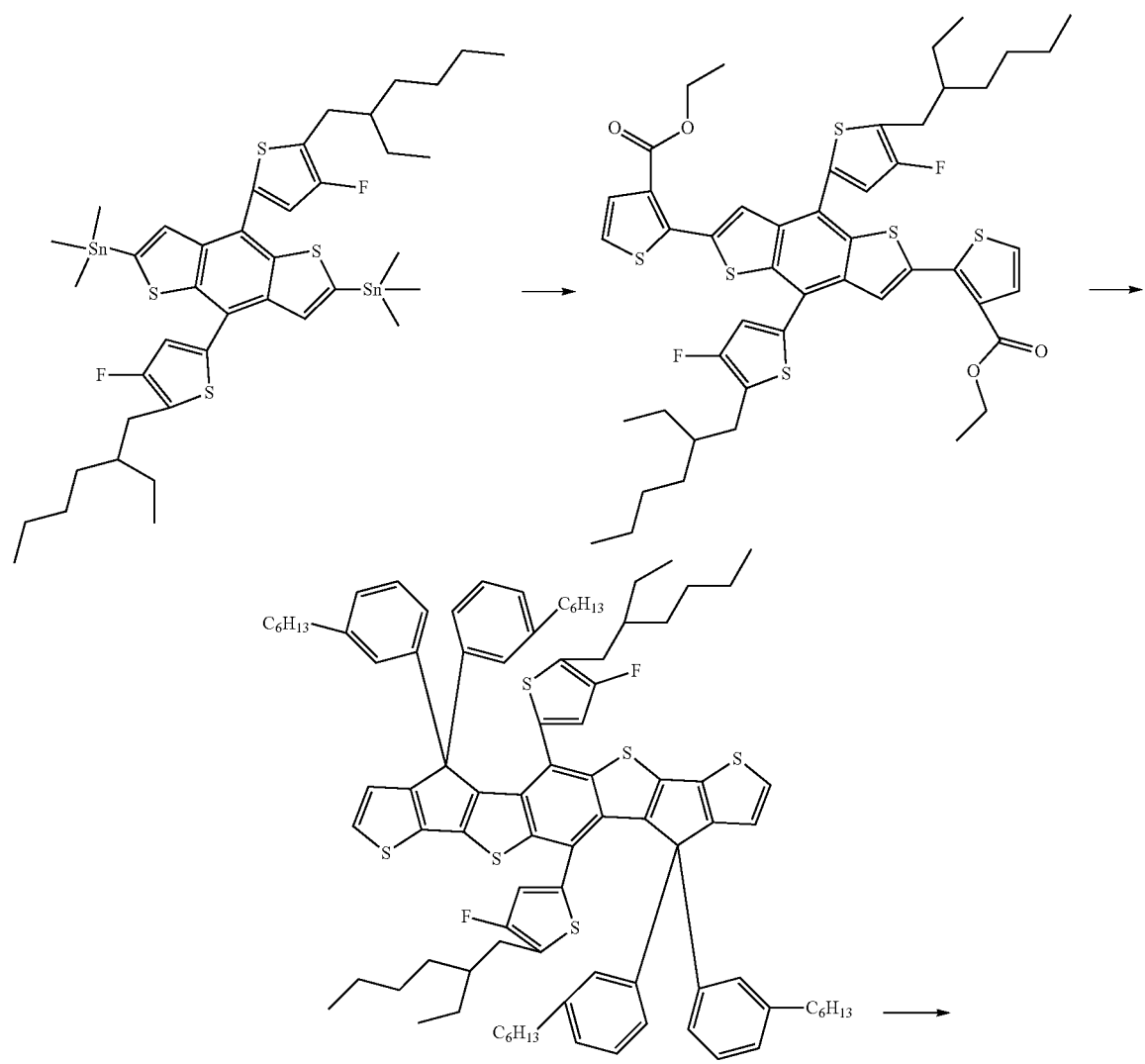

-continued

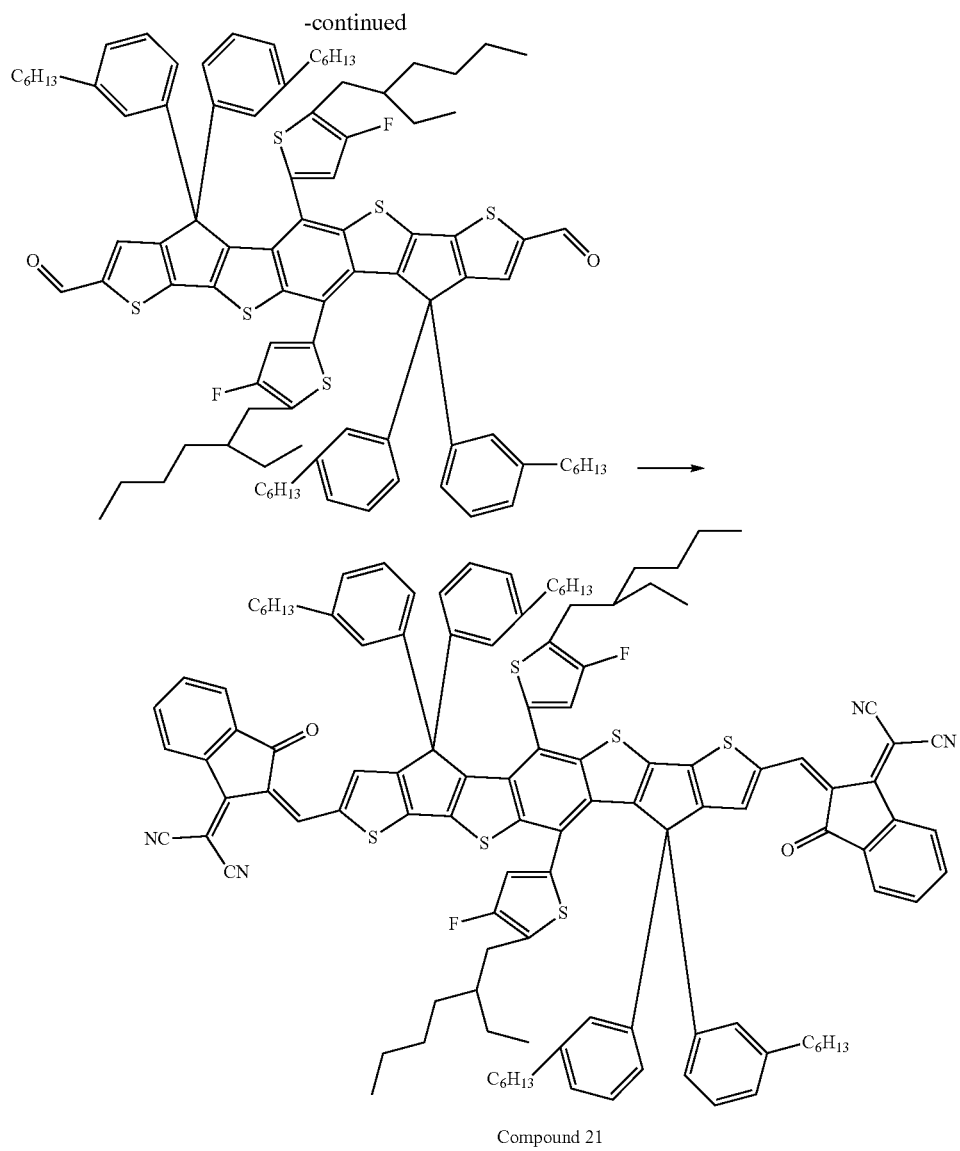

Compound 21

Compound 21 was prepared in the same manner as in Preparation Example 6 except that 3-bromo-4-hexylbenzene was used instead of 1-bromo-4-hexylbenzene in Preparation Example 6.

<Preparation Examples 22 to 25> Preparation of Compounds 22 to 25

The following Compounds 22 to 25 were prepared in the same manner as in Preparation Example 21, except that the respective materials in the following Table 5 were used instead of 2-(3-oxo-2,3-dihydro-1H-inden-1-ylidene)malononitrile in Preparation Example 21.

TABLE 5

| Target compound | Used material |
|---|---|
| Compound 22 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |

TABLE 5-continued
| Target compound | Used material |
|---|---|
| Compound 23 | 2-(5,6-difluoro-3-oxo-2,3-dihydro-1H-inden-1-ylidene)malononitrile |
| Compound 24 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 25 | 2-(5,6-dimethyl-3-oxo-2,3-dihydro-1H-inden-1-ylidene)malononitrile |
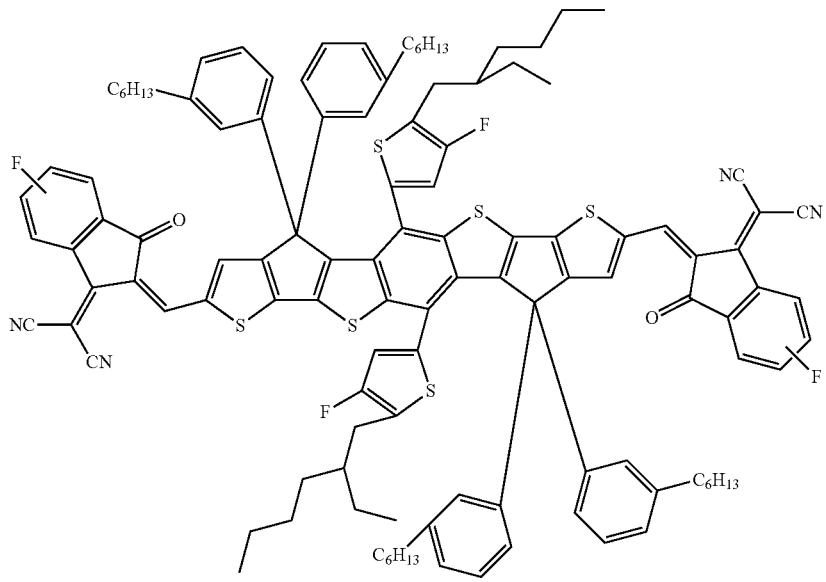
[Compound 22]
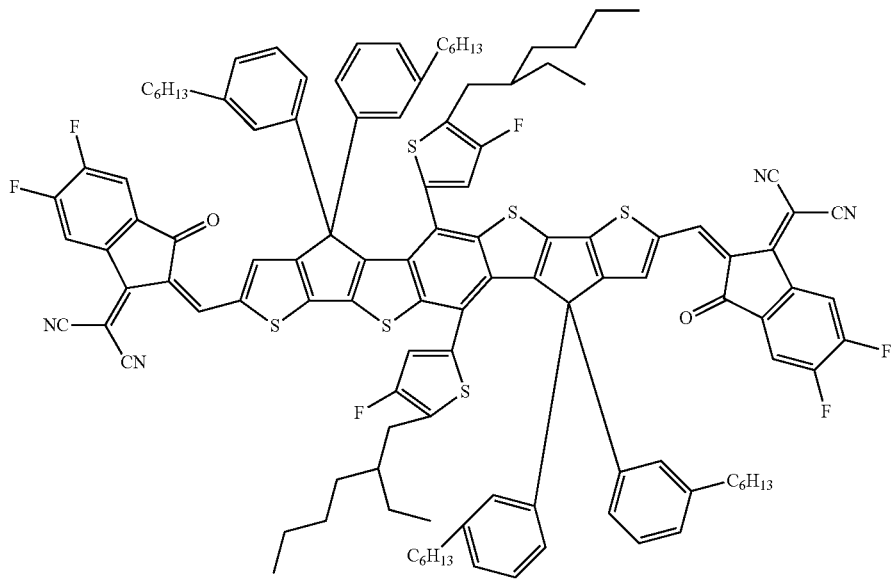
[Compound 23]

[Compound 24]
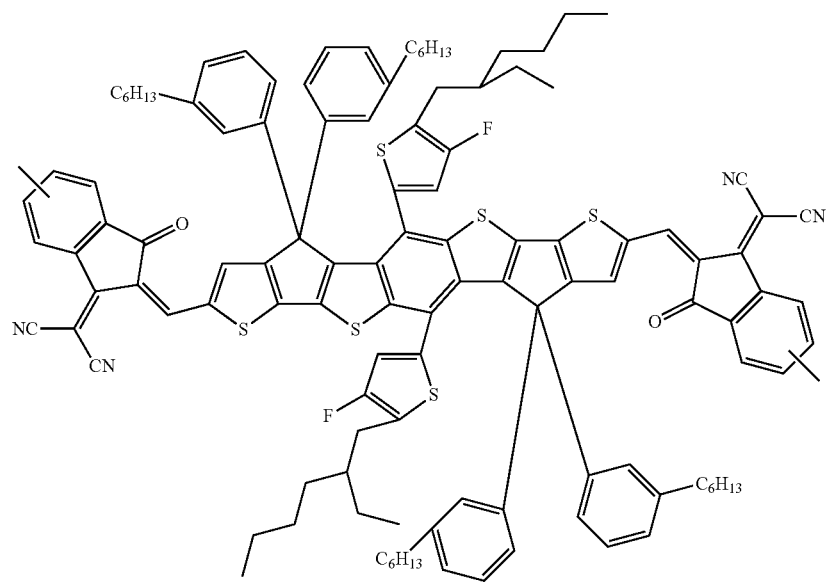
[Compound 25]
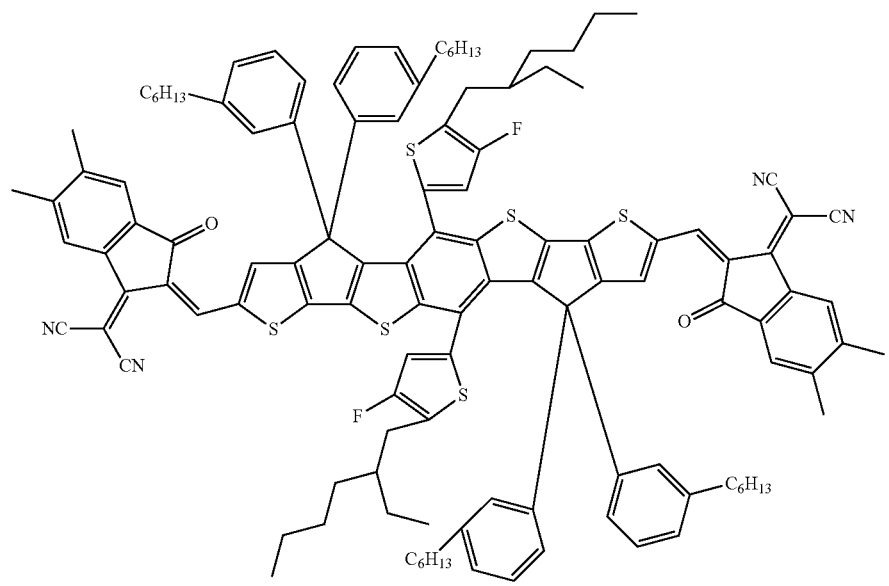

<Preparation Example 26> Preparation of Compound 26
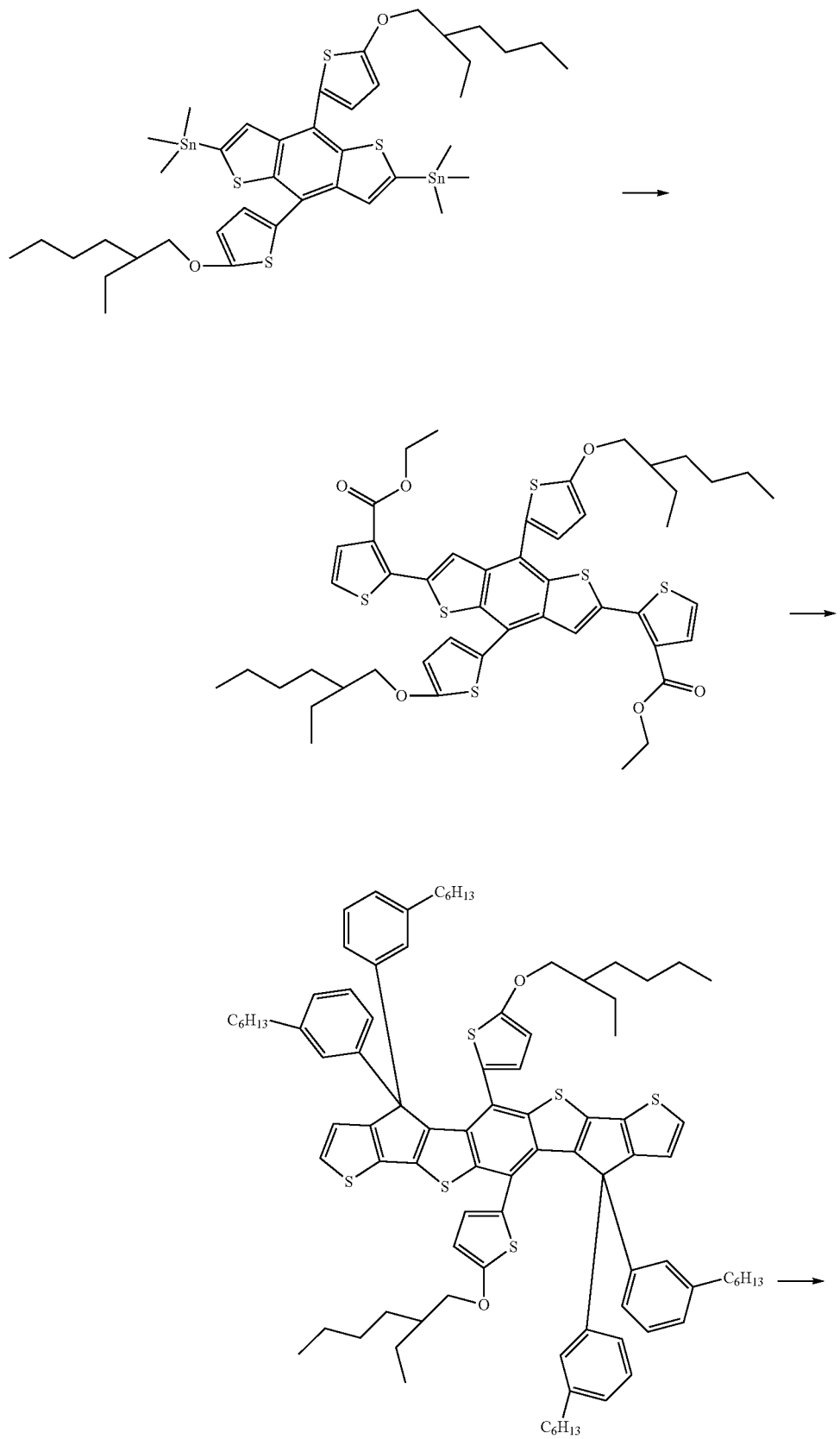

-continued

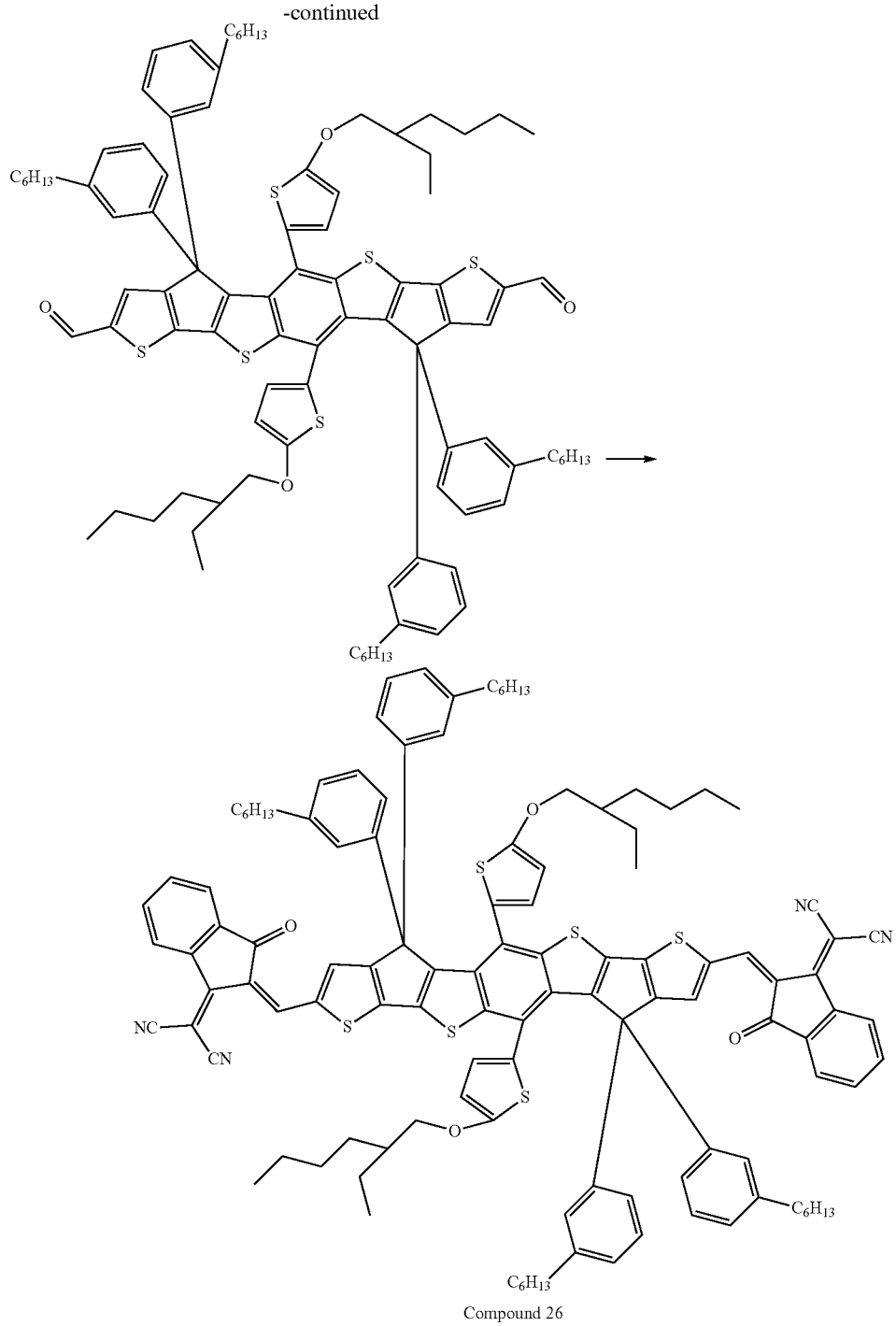

Compound 26

Compound 26 was prepared in the same manner as in Preparation Example 11, except that 3-bromo-4-hexylbenzene was used instead of 1-bromo-4-hexylbenzene in Preparation Example 11.

<Preparation Examples 27 to 30> Preparation of Compounds 27 to 30

The following Compounds 27 to 30 were prepared in the same manner as in Preparation Example 26, except that the respective materials in the following Table 6 were used instead of 2-(3-oxo-2,3-dihydro-1H-inden-1-ylidene)malononitrile in Preparation Example 26.

TABLE 6

| Target compound | Used material |
|---|---|
| Compound 27 | Compound in which 2-(6-fluoro-3-oxo-2,3-dihydro-1H-inden-1-ylidene)malononitrile and 2-(5-fluoro-3-oxo-2,3-dihydro-1H-inden-1-ylidene)malononitrile are mixed at a mass ratio of 3:7 |
| Compound 28 | 2-(5,6-difluoro-3-oxo-2,3-dihydro-1H-inden-1-ylidene)malononitrile |
| Compound 29 | Compound in which 2-(6-methyl-3-oxo-2,3-dihydro-1H-inden-1-ylidene)malononitrile and 2-(5-methyl-3-oxo-2,3-dihydro-1H-inden-1-ylidene)malononitrile are mixed at a mass ratio of 3:7 |
| Compound 30 | 2-(5,6-dimethyl-3-oxo-2,3-dihydro-1H-inden-1-ylidene)malononitrile |

[Compound 27]

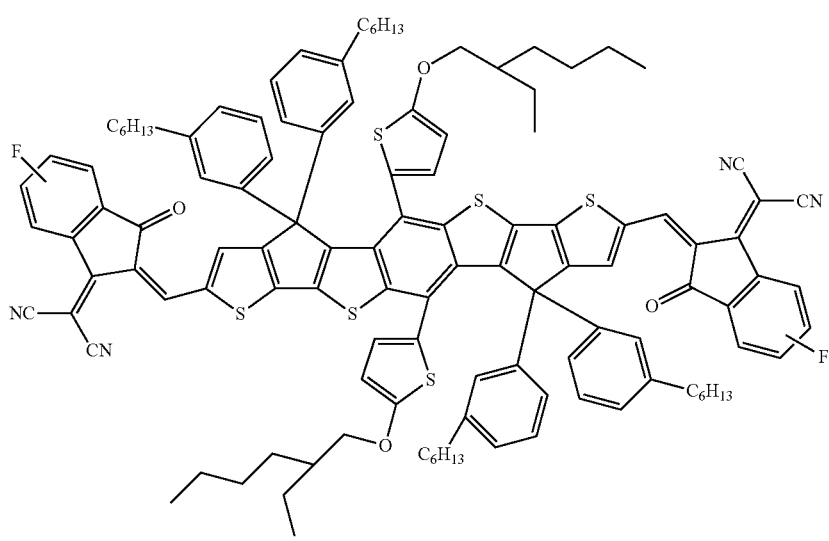

[Compound 28]

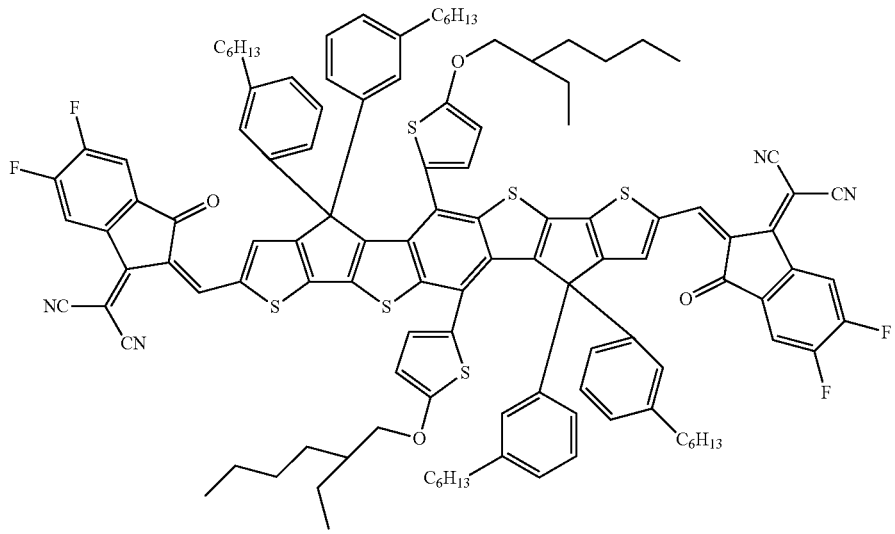

[Compound 29]
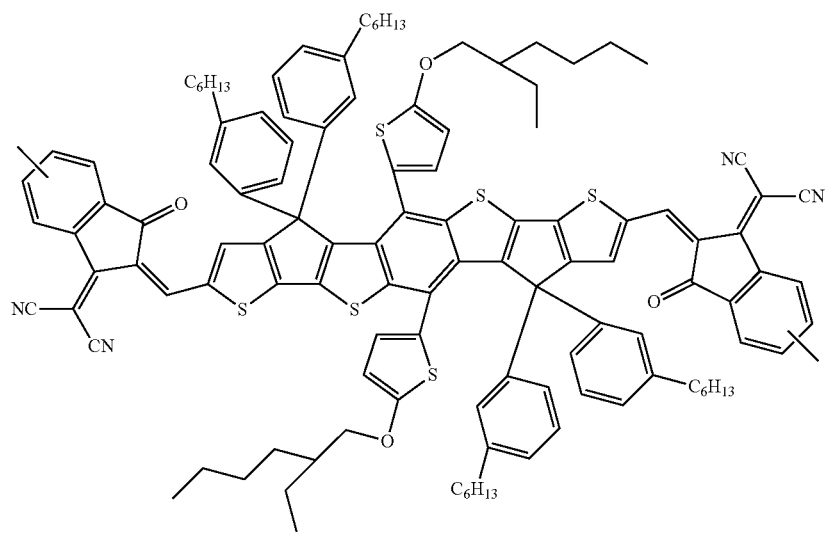
[Compound 30]
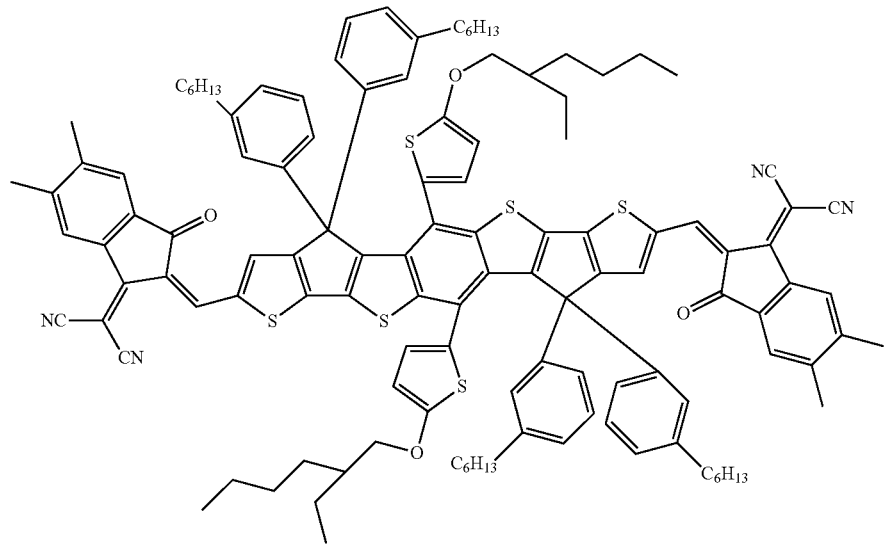
[Comparative Example Compound 1(BT-IC)]
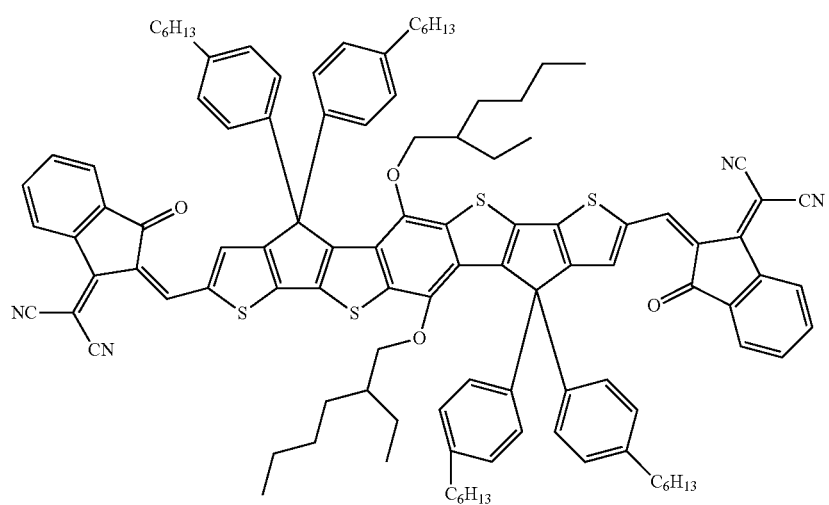

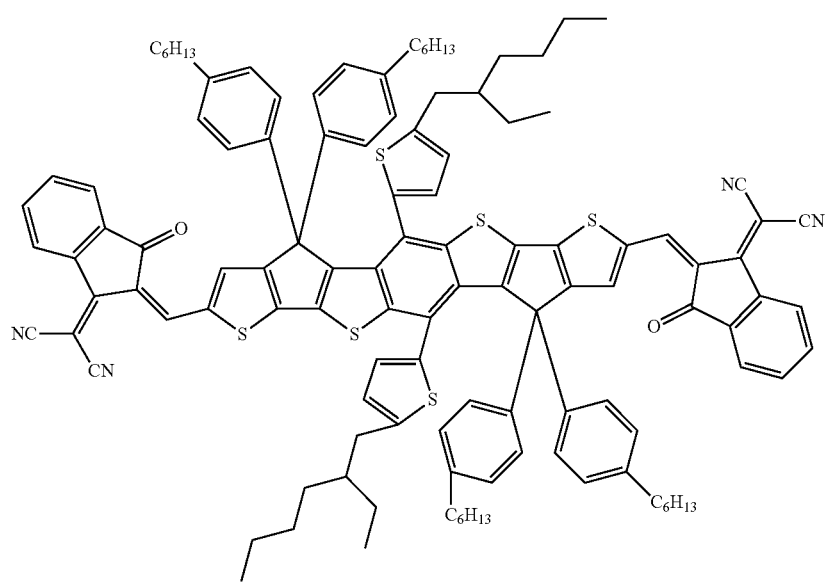

[Comparative Example Compound 2(ITIC2)]

Comparative Example Compounds 1 and 2 were purchased from Solarmer Materials Inc., and then used.

The following Table 7 exhibits optical properties of Compounds 1, 3, 6, 8, and 16 to 25. The results of the following Table 7 were measured by FIGS. 6 and 7, and the following results were obtained by measuring UV-vis spectra in a solution state and in a film state. Further, physical properties of Compounds 1 to 25 were measured, and are shown in the following Table 8.

TABLE 7

|  | Solution | Film | |
| --- | --- | --- | --- |
|  | $\lambda_{max, abs}$ (nm) | $\lambda_{max}$ (nm) | $\lambda_{edge}$ (nm) |
| Compound 1 | 670 | 704 | 794 |
| Compound 3 | 683 | 711 | 809 |
| Compound 6 | 678 | 579 | 779 |
| Compound 8 | 691 | 623 | 786 |
| Compound 16 | 680 | 681 | 805 |
| Compound 17 | 681 | 683 | 826 |
| Compound 18 | 683 | 685 | 832 |
| Compound 19 | 678 | 680 | 789 |
| Compound 20 | 676 | 678 | 784 |
| Compound 21 | 677 | 680 | 821 |
| Compound 22 | 678 | 681 | 837 |
| Compound 23 | 679 | 682 | 810 |
| Compound 24 | 675 | 677 | 843 |
| Compound 25 | 675 | 678 | 800 |

TABLE 8

|  | Optical bandgap (eV) | HOMO (eV) | LUMO (eV) |
| --- | --- | --- | --- |
| Compound 1 | 1.55 | −5.73 | −4.18 |
| Compound 2 | 1.54 | −5.80 | −4.26 |
| Compound 3 | 1.52 | −5.86 | −4.34 |
| Compound 4 | 1.58 | −5.83 | −4.25 |
| Compound 5 | 1.56 | −5.79 | −4.23 |
| Compound 6 | 1.55 | −5.88 | −4.34 |
| Compound 7 | 1.54 | −5.96 | −4.46 |
| Compound 8 | 1.52 | −6.04 | −4.55 |
| Compound 9 | 1.58 | −5.87 | −4.30 |
| Compound 10 | 1.56 | −5.82 | −4.24 |
| Compound 11 | 1.55 | −5.73 | −4.18 |
| Compound 12 | 1.54 | −5.80 | −4.26 |
| Compound 13 | 1.52 | −5.86 | −4.34 |
| Compound 14 | 1.58 | −5.83 | −4.25 |
| Compound 15 | 1.56 | −5.79 | −4.23 |
| Compound 16 | 1.54 | −5.88 | −4.34 |
| Compound 17 | 1.50 | −5.96 | −4.46 |
| Compound 18 | 1.49 | −6.04 | −4.55 |
| Compound 19 | 1.57 | −5.87 | −4.30 |
| Compound 20 | 1.58 | −5.82 | −4.24 |
| Compound 21 | 1.51 | −5.99 | −4.48 |
| Compound 22 | 1.48 | −6.00 | −4.53 |
| Compound 23 | 1.53 | −5.75 | −4.22 |
| Compound 24 | 1.47 | −5.80 | −4.33 |
| Compound 25 | 1.55 | −5.82 | −4.27 |

In Table 7, Solution $\lambda_{max}$, Film $\lambda_{max}$, and Film $\lambda_{edge}$ mean the maximum absorption wavelength in a solution state, the maximum absorption wavelength in a film state, and an absorption edge wavelength in a film state, respectively, and in Table 8, optical bandgap, HOMO, and LUMO mean the optical bandgap, the highest occupied molecular orbital, and the lowest unoccupied molecular orbital, respectively.

Compounds 1, 3, 6, 8, and 16 to 25 have excellent ability to withdraw electrons as in the results in Table 7 and thus can absorb light in a long wavelength region.

Comparative Example 1-1. Manufacture of Organic Solar Cell

A composite solution was prepared by dissolving the following compound PBDB-T and Comparative Example Compound 1 (BT-IC) at a ratio of 1:2 in chlorobenzene (CB). In this case, the concentration was adjusted to 2 wt/vol %, the composite solution was stirred at 700 rpm at 70° C. overnight, 0.25% of diphenyl ether (DPE) was added to the composite solution, and the composite solution was annealed at 100° C. to 120° C. An organic solar cell was made to have an inverted structure of ITO/ZnO NP/a photoactive layer/MoO₃/Ag.

A bar-type glass substrate (11.5Ω/□) coated with ITO with 1.5 cm×1.5 cm was ultrasonically washed by using distilled water, acetone, and 2-propanol, the ITO surface was treated with ozone for 10 minutes, and then ZnO NP (2.5 wt % of ZnO nanograde N-10 in 1-butanol, filtered by a 0.45 μm PTFE) was prepared, the ZnO NP solution was spin-coated at 4,000 rpm for 40 seconds, and then the remaining solvent was removed by performing a heat treatment at 80° C. for 10 minutes, thereby completing an electron transport layer. For the coating of the photoactive layer, the annealed composite solution was spin-coated at 1,500 rpm for 15 seconds. In a thermal evaporator, $MoO_3$ was thermally deposited to have a thickness of 10 nm at a rate of 0.2 Å/s under $10^{-7}$ Torr, thereby manufacturing a hole transport layer. After the manufacture in the above order, Ag was deposited to have a thickness of 100 nm at a rate of 1 Å/s in the thermal evaporator, thereby manufacturing an organic solar cell having an inverted structure.

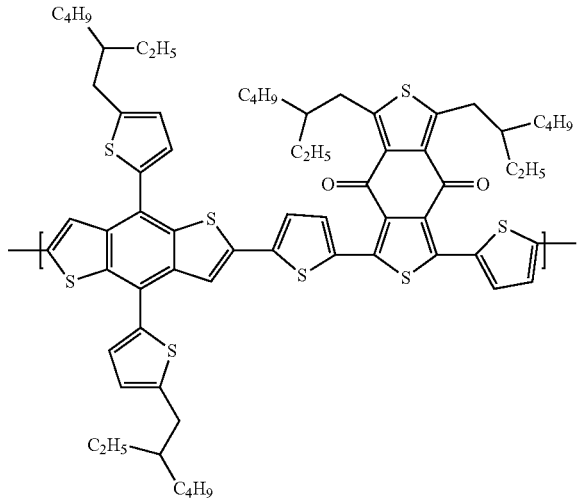

[PBDB-T]

Comparative Examples 1-2 to 1-4. Manufacture of Organic Solar Cell

Organic solar cells were manufactured in the same manner as in Comparative Example 1-1, except that for the coating of the photoactive layer in Comparative Example 1-1, the composite solution was spin-coated at the spin-speed described in the following Table 9 instead of 1,500 rpm.

The photoelectric conversion characteristics of the organic solar cells manufactured in Comparative Examples 1-1 to 1-4 were measured under the condition of 100 mW/cm² (AM 1.5), and the results thereof are shown in the following Table 9.

TABLE 9

| | Spin-speed (rpm) | $V_{oc}$ (V) | $J_{sc}$ (mA/cm²) | FF (%) | η (%) | Average η N |
|---|---|---|---|---|---|---|
| Comparative Example 1-1 | 1500 | 1.027 | 13.289 | 0.550 | 7.50 | 7.44 |
| | | 1.023 | 13.140 | 0.549 | 7.37 | |
| Comparative Example 1-2 | 1700 | 1.030 | 13.286 | 0.567 | 7.75 | 7.75 |
| | | — | — | — | — | |

TABLE 9-continued

| | Spin-speed (rpm) | $V_{oc}$ (V) | $J_{sc}$ (mA/cm²) | FF (%) | η (%) | Average η N |
|---|---|---|---|---|---|---|
| Comparative Example 1-3 | 1900 | 1.030 | 13.539 | 0.592 | 8.26 | 8.19 |
| | | 1.028 | 13.220 | 0.597 | 8.11 | |
| Comparative Example 1-4 | 2200 | 1.030 | 13.340 | 0.610 | 8.38 | 8.41 |
| | | 1.026 | 13.620 | 0.603 | 8.43 | |

Comparative Examples 2-1 to 2-4. Manufacture of Organic Solar Cell

Organic solar cells were manufactured in the same manner as in Comparative Example 1-1, except that in Comparative Example 1-1, Comparative Example Compound 2 (ITIC2) was used instead of Comparative Example Compound 1, and the composite solution prepared by using Comparative Example Compound 2 (ITIC2) instead of Comparative Example Compound 1 was spin-coated at the spin-speed described in the following Table 10 instead of 1,500 rpm.

The photoelectric conversion characteristics of the organic solar cells manufactured in Comparative Examples 2-1 to 2-4 were measured under the condition of 100 mW/cm² (AM 1.5), and the results thereof are shown in the following Table 10.

TABLE 10

| | Spin-speed (rpm) | $V_{oc}$ (V) | $J_{sc}$ (mA/cm²) | FF (%) | η (%) | Average η N |
|---|---|---|---|---|---|---|
| Comparative Example 2-1 | 1500 | 1.021 | 13.870 | 0.586 | 8.30 | 8.19 |
| | | 1.017 | 14.232 | 0.557 | 8.07 | |
| Comparative Example 2-2 | 1700 | 1.024 | 13.775 | 0.582 | 8.22 | 8.59 |
| | | 1.018 | 14.853 | 0.592 | 8.95 | |
| Comparative Example 2-3 | 1900 | 1.028 | 14.635 | 0.602 | 9.07 | 9.18 |
| | | 1.024 | 14.720 | 0.616 | 9.29 | |
| Comparative Example 2-4 | 2200 | 1.023 | 13.914 | 0.620 | 8.83 | 8.87 |
| | | 1.021 | 14.230 | 0.613 | 8.91 | |

Examples 1-1 to 1-6. Manufacture of Organic Solar Cell

Organic solar cells were manufactured in the same manner as in Comparative Example 1-1, except that in Comparative Example 1-1, Compound 1 was used instead of Comparative Example Compound 1, and the composite solution prepared by using Compound 1 instead of Comparative Example Compound 1 was spin-coated at the spin-speed described in the following Table 11 instead of 1,500 rpm.

The photoelectric conversion characteristics of the organic solar cells manufactured in Examples 1-1 to 1-6 were measured under the condition of 100 mW/cm² (AM 1.5), and the results thereof are shown in the following Table 11.

TABLE 11

| | Spin-speed (rpm) | $V_{oc}$ (V) | $J_{sc}$ (mA/cm²) | FF (%) | η (%) | Average η N |
|---|---|---|---|---|---|---|
| Example 1-1 | 1000 | 0.917 | 15.654 | 0.739 | 10.60 | 10.41 |
| | | 0.916 | 15.163 | 0.736 | 10.22 | |
| Example 1-2 | 1200 | 0.912 | 15.198 | 0.726 | 10.06 | 9.90 |
| | | 0.907 | 14.647 | 0.733 | 9.73 | |
| Example 1-3 | 1400 | 0.914 | 13.305 | 0.737 | 8.97 | 9.22 |
| | | 0.911 | 13.933 | 0.746 | 9.47 | |

TABLE 11-continued

| | Spin-speed (rpm) | $V_{oc}$ (V) | $J_{sc}$ (mA/cm²) | FF (%) | η (%) | Average η N |
|---|---|---|---|---|---|---|
| Example 1-4 | 1600 | 0.913 | 13.379 | 0.746 | 9.11 | 9.09 |
| | | 0.910 | 13.383 | 0.745 | 9.07 | |
| Example 1-5 | 1800 | 0.910 | 13.132 | 0.744 | 8.89 | 9.09 |
| | | 0.907 | 13.772 | 0.744 | 9.29 | |
| Example 1-6 | 2000 | 0.898 | 12.880 | 0.724 | 8.37 | 8.29 |
| | | 0.902 | 12.235 | 0.743 | 8.21 | |

Examples 2-1 to 2-5. Manufacture of Organic Solar Cell

Organic solar cells were manufactured in the same manner as in Comparative Example 1-1, except that in Comparative Example 1-1, Compound 3 was used instead of Comparative Example Compound 1, and the composite solution prepared by using Compound 3 instead of Comparative Example Compound 1 was spin-coated at the spin-speed described in the following Table 12 instead of 1,500 rpm.

The photoelectric conversion characteristics of the organic solar cells manufactured in Examples 2-1 to 2-5 were measured under the condition of 100 mW/cm² (AM 1.5), and the results thereof are shown in the following Table 12.

TABLE 12

| | Spin-speed (rpm) | $V_{oc}$ (V) | $J_{sc}$ (mA/cm²) | FF (%) | η (%) | Average η N |
|---|---|---|---|---|---|---|
| Example 2-1 | 800 | 0.896 | 16.173 | 0.681 | 9.87 | 9.78 |
| | | 0.885 | 16.248 | 0.673 | 9.68 | |
| Example 2-2 | 1000 | 0.889 | 16.464 | 0.703 | 10.29 | 10.38 |
| | | 0.890 | 16.796 | 0.700 | 10.46 | |
| Example 2-3 | 1200 | 0.887 | 16.080 | 0.708 | 10.10 | 10.39 |
| | | 0.885 | 17.294 | 0.698 | 10.68 | |
| Example 2-4 | 1400 | 0.891 | 15.483 | 0.711 | 9.81 | 9.90 |
| | | 0.887 | 15.981 | 0.705 | 9.99 | |
| Example 2-5 | 1600 | 0.884 | 15.481 | 0.717 | 9.82 | 9.82 |
| | | 0.887 | 15.467 | 0.716 | 9.82 | |

Examples 3-1 to 3-5. Manufacture of Organic Solar Cell

Organic solar cell were manufactured in the same manner as in Comparative Example 1-1, except that in Comparative Example 1-1, Compound 6 was used instead of Comparative Example Compound 1, and the composite solution prepared by using Compound 6 instead of Comparative Example Compound 1 was spin-coated at the spin-speed described in the following Table 13 instead of 1,500 rpm.

The photoelectric conversion characteristics of the organic solar cells manufactured in Examples 3-1 to 3-5 were measured under the condition of 100 mW/cm² (AM 1.5), and the results thereof are shown in the following Table 13.

TABLE 13

| | Spin-speed (rpm) | $V_{oc}$ (V) | $J_{sc}$ (mA/cm²) | FF (%) | η (%) | Average η N |
|---|---|---|---|---|---|---|
| Example 3-1 | 800 | 0.853 | 16.132 | 0.669 | 9.20 | 9.23 |
| | | 0.851 | 16.508 | 0.659 | 9.26 | |

TABLE 13-continued

| | Spin-speed (rpm) | $V_{oc}$ (V) | $J_{sc}$ (mA/cm²) | FF (%) | η (%) | Average η N |
|---|---|---|---|---|---|---|
| Example 3-2 | 1000 | 0.856 | 15.895 | 0.680 | 9.24 | 9.32 |
| | | 0.856 | 15.843 | 0.693 | 9.39 | |
| Example 3-3 | 1200 | 0.849 | 15.137 | 0.697 | 8.96 | 9.04 |
| | | 0.845 | 15.487 | 0.696 | 9.11 | |
| Example 3-4 | 1400 | 0.849 | 15.018 | 0.699 | 8.92 | 8.91 |
| | | 0.847 | 14.925 | 0.705 | 8.90 | |
| Example 3-5 | 1600 | 0.849 | 14.443 | 0.706 | 8.65 | 8.73 |
| | | 0.846 | 14.574 | 0.714 | 8.81 | |

Examples 4-1 to 4-4. Manufacture of Organic Solar Cell

Organic solar cells were manufactured in the same manner as in Comparative Example 1-1, except that in Comparative Example 1-1, Compound 8 was used instead of Comparative Example Compound 1, and the composite solution prepared by using Compound 8 instead of Comparative Example Compound 1 was spin-coated at the spin-speed described in the following Table 14 instead of 1,500 rpm.

The photoelectric conversion characteristics of the organic solar cells manufactured in Examples 4-1 to 4-4 were measured under the condition of 100 mW/cm² (AM 1.5), and the results thereof are shown in the following Table 14.

TABLE 14

| | Spin-speed (rpm) | $V_{oc}$ (V) | $J_{sc}$ (mA/cm²) | FF (%) | η (%) | Average η N |
|---|---|---|---|---|---|---|
| Example 4-1 | 1000 | 0.893 | 15.852 | 0.705 | 9.97 | 9.97 |
| | | — | — | — | — | |
| Example 4-2 | 1200 | 0.895 | 15.829 | 0.704 | 9.98 | 9.99 |
| | | 0.889 | 15.778 | 0.713 | 10.00 | |
| Example 4-3 | 1400 | 0.894 | 15.318 | 0.696 | 9.53 | 9.83 |
| | | 0.886 | 16.118 | 0.710 | 10.13 | |
| Example 4-4 | 1600 | 0.893 | 15.519 | 0.713 | 9.89 | 9.97 |
| | | 0.891 | 15.714 | 0.718 | 10.04 | |

From the results of Tables 9 to 14, it can be seen that the organic solar cell comprising the heterocyclic compound represented by Formula 1 according to an exemplary embodiment of the present specification has better fill factor, and photoelectric conversion efficiency than those of the organic solar cell comprising Comparative Example Compounds 1 and 2.

Comparative Example 3-1. Manufacture of Organic Solar Cell

A composite solution was prepared by dissolving Compound PBDB-T and Comparative Example Compound 2 (ITIC2) at a ratio of 1:2 in chlorobenzene (CB). In this case, the concentration was adjusted to 2 wt/vol %, the composite solution was stirred at 700 rpm at 70° C. overnight, 0.5% of 1,8-diiodooctane (DIO) was added to the composite solution, and the composite solution was annealed at 100° C. to 120° C. An organic solar cell was made to have an inverted structure of ITO/ZnO NP/a photoactive layer/MoO₃/Ag.

A bar-type glass substrate (11.5Ω/□) coated with ITO with 1.5 cm×1.5 cm was ultrasonically washed by using distilled water, acetone, and 2-propanol, the ITO surface was treated with ozone for 10 minutes, and then ZnO NP (2.5 wt % of ZnO nanograde N-10 in 1-butanol, filtered by a 0.45

µm PTFE) was prepared, the ZnO NP solution was spin-coated at 4,000 rpm for 40 seconds, and then the remaining solvent was removed by performing a heat treatment at 80° C. for 10 minutes, thereby completing an electron transport layer. For the coating of the photoactive layer, the annealed composite solution was spin-coated at 800 rpm for 15 seconds. In a thermal evaporator, $MoO_3$ was thermally deposited to have a thickness of 10 nm at a rate of 0.2 Å/s under $10^{-7}$ Torr, thereby manufacturing a hole transport layer. After the manufacture in the above order, Ag was deposited to have a thickness of 100 nm at a rate of 1 Å/s in the thermal evaporator, thereby manufacturing an organic solar cell having an inverted structure.

Comparative Examples 3-2 to 3-4. Manufacture of Organic Solar Cell

Organic solar cells were manufactured in the same manner as in Comparative Example 3-1, except that for the coating of the photoactive layer in Comparative Example 3-1, the composite solution was spin-coated at the spin-speed described in the following Table 15 instead of 800 rpm.

Examples 5-1 to 5-4. Manufacture of Organic Solar Cell

Organic solar cells were manufactured in the same manner as in Comparative Example 3-1, except that in Comparative Example 3-1, Compound 1 was used instead of Comparative Example Compound 2, and the composite solution prepared by using Compound 1 instead of Comparative Example Compound 2 was spin-coated at the spin-speed described in the following Table 15 instead of 800 rpm.

Figure 8:
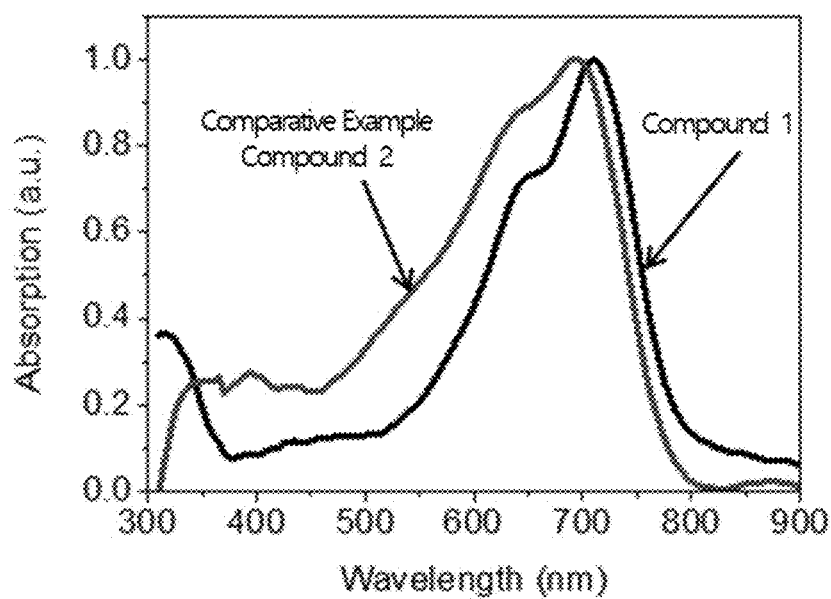
FIG. 8 is a view illustrating UV-vis absorption spectra of Compound 1 according to an exemplary embodiment of the present specification and Comparative Example Compound 2 (ITIC2) in a solution state.

FIG. 8 is a view illustrating UV-vis absorption spectra of Compound 1 and Comparative Example Compound 2 (ITIC2) in a solution state.

Specifically, FIG. 8 illustrates data obtained by measuring the UV-vis absorption spectrum after each of Compound 1 and Comparative Example Compound 2 (ITIC2) was dissolved in chlorobenzene.

In FIG. 8, it could be confirmed that the UV-Vis absorption region of Compound 1 was transferred more toward the long wavelength than that of Comparative Example Compound 2, due to the introduction of a thioalkoxy group. Further, in FIG. 8, a shoulder peak at 720 nm appearing at the UV-Vis absorption spectrum of Compound 1 may be seen as a proof that Compound 1 has a better π-π stacking than Comparative Example Compound 2, which may be an indirect proof that the hole/electron mobility of the molecule itself is excellent. This becomes an important element which exhibits a high short-circuit current in an organic solar cell.

Examples 6-1 to 6-4. Manufacture of Organic Solar Cell

Organic solar cells were manufactured in the same manner as in Comparative Example 3-1, except that in Comparative Example 3-1, Compound 6 was used instead of Comparative Example Compound 2, and the composite solution prepared by using Compound 6 instead of Comparative Example Compound 2 was spin-coated at the spin-speed described in the following Table 15 instead of 800 rpm.

Figure 9:
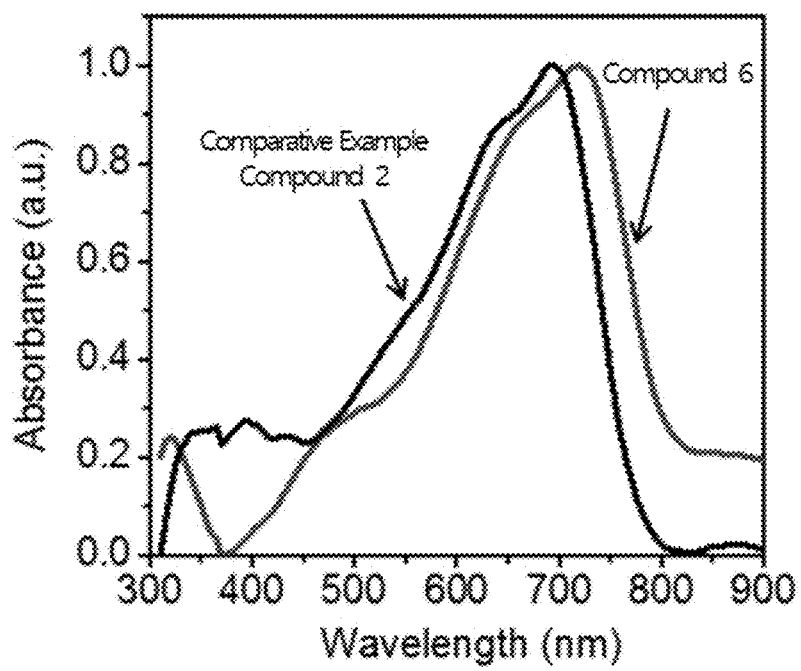
FIG. 9 is a view illustrating UV-vis absorption spectra of Compound 6 according to an exemplary embodiment of the present specification and Comparative Example Compound 2 (ITIC2) in a solution state.

FIG. 9 is a view illustrating UV-vis absorption spectra of Compound 6 and Comparative Example Compound 2 (ITIC2) in a solution state.

Specifically, FIG. 9 illustrates data obtained by measuring the UV-vis absorption spectrum after each of Compound 6 and Comparative Example Compound 2 (ITIC2) was dissolved in chlorobenzene.

In FIG. 9, it could be confirmed that the UV-Vis absorption region of Compound 6 was transferred more toward the long wavelength than that of Comparative Example Compound 2, due to the introduction of F atoms, and this becomes an important element exhibiting high short-circuit current in an organic solar cell.

Examples 7-1 to 7-4. Manufacture of Organic Solar Cell

Organic solar cells were manufactured in the same manner as in Comparative Example 3-1, except that in Comparative Example 3-1, Compound 11 was used instead of Comparative Example Compound 2, and the composite solution prepared by using Compound 11 instead of Comparative Example Compound 2 was spin-coated at the spin-speed described in the following Table 15 instead of 800 rpm.

Figure 10:
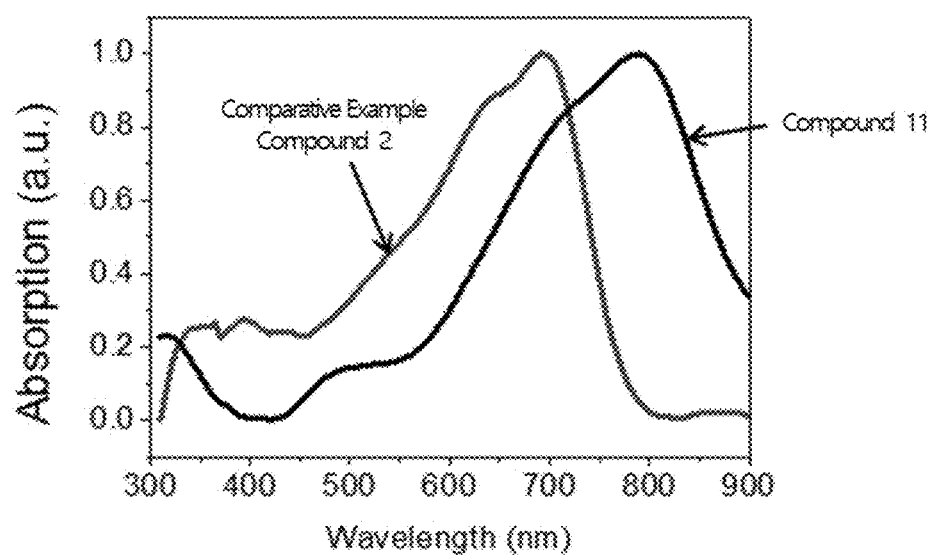
FIG. 10 is a view illustrating UV-vis absorption spectra of Compound 11 according to an exemplary embodiment of the present specification and Comparative Example Compound 2 (ITIC2) in a solution state.

FIG. 10 is a view illustrating UV-vis absorption spectra of Compound 11 and Comparative Example Compound 2 (ITIC2) in a solution state.

Specifically, FIG. 10 illustrates data obtained by measuring the UV-vis absorption spectrum after each of Compound 11 and Comparative Example Compound 2 (ITIC2) was dissolved in chlorobenzene.

In FIG. 10, it could be confirmed that the UV-Vis absorption region of Compound 11 was transferred more toward the longer wavelength than that of Comparative Example Compound 2, due to the introduction of an alkoxy group.

Further, it can be seen that the long wavelength transfer range of the UV-Vis spectrum is wide due to the introduction of oxygen atoms having an excellent ability to donate electrons. This becomes an important element which exhibits a high short-circuit current in an organic solar cell.

Examples 8-1 to 8-4. Manufacture of Organic Solar Cell

Organic solar cells were manufactured in the same manner as in Comparative Example 3-1, except that in Comparative Example 3-1, Compound 16 was used instead of Comparative Example Compound 2, and the composite solution prepared by using Compound 16 instead of Comparative Example Compound 2 was spin-coated at the spin-speed described in the following Table 15 instead of 800 rpm.

Examples 9-1 to 9-4. Manufacture of Organic Solar Cell

Organic solar cells were manufactured in the same manner as in Comparative Example 3-1, except that in Comparative Example 3-1, Compound 17 was used instead of Comparative Example Compound 2, and the composite solution prepared by using Compound 17 instead of Comparative Example Compound 2 was spin-coated at the spin-speed described in the following Table 15 instead of 800 rpm.

Examples 10-1 to 10-4. Manufacture of Organic Solar Cell

Organic solar cells were manufactured in the same manner as in Comparative Example 3-1, except that in Comparative Example 3-1, Compound 18 was used instead of Comparative Example Compound 2, and the composite solution prepared by using Compound 18 instead of Comparative Example Compound 2 was spin-coated at the spin-speed described in the following Table 15 instead of 800 rpm.

Examples 11-1 to 11-4. Manufacture of Organic Solar Cell

Organic solar cells were manufactured in the same manner as in Comparative Example 3-1, except that in Comparative Example 3-1, Compound 19 was used instead of Comparative Example Compound 2, and the composite solution prepared by using Compound 19 instead of Comparative Example Compound 2 was spin-coated at the spin-speed described in the following Table 15 instead of 800 rpm.

Examples 12-1 to 12-4. Manufacture of Organic Solar Cell

Organic solar cells were manufactured in the same manner as in Comparative Example 3-1, except that in Comparative Example 3-1, Compound 20 was used instead of Comparative Example Compound 2, and the composite solution prepared by using Compound 20 instead of Comparative Example Compound 2 was spin-coated at the spin-speed described in the following Table 15 instead of 800 rpm.

Examples 13-1 to 13-4. Manufacture of Organic Solar Cell

Organic solar cells were manufactured in the same manner as in Comparative Example 3-1, except that in Comparative Example 3-1, Compound 21 was used instead of Comparative Example Compound 2, and the composite solution prepared by using Compound 21 instead of Comparative Example Compound 2 was spin-coated at the spin-speed described in the following Table 15 instead of 800 rpm.

Examples 14-1 to 14-4. Manufacture of Organic Solar Cell

Organic solar cells were manufactured in the same manner as in Comparative Example 3-1, except that in Comparative Example 3-1, Compound 22 was used instead of Comparative Example Compound 2, and the composite solution prepared by using Compound 22 instead of Comparative Example Compound 2 was spin-coated at the spin-speed described in the following Table 15 instead of 800 rpm.

Examples 15-1 to 15-4. Manufacture of Organic Solar Cell

Organic solar cells were manufactured in the same manner as in Comparative Example 3-1, except that in Comparative Example 3-1, Compound 23 was used instead of Comparative Example Compound 2, and the composite solution prepared by using Compound 23 instead of Comparative Example Compound 2 was spin-coated at the spin-speed described in the following Table 15 instead of 800 rpm.

Examples 16-1 to 16-4. Manufacture of Organic Solar Cell

Organic solar cells were manufactured in the same manner as in Comparative Example 3-1, except that in Comparative Example 3-1, Compound 24 was used instead of Comparative Example Compound 2, and the composite solution prepared by using Compound 24 instead of Comparative Example Compound 2 was spin-coated at the spin-speed described in the following Table 15 instead of 800 rpm.

Examples 17-1 to 17-4. Manufacture of Organic Solar Cell

Organic solar cells were manufactured in the same manner as in Comparative Example 3-1, except that in Comparative Example 3-1, Compound 25 was used instead of Comparative Example Compound 2, and the composite solution prepared by using Compound 25 instead of Comparative Example Compound 2 was spin-coated at the spin-speed described in the following Table 15 instead of 800 rpm.

The photoelectric conversion characteristics of the organic solar cells manufactured in Comparative Examples 3-1 to 3-4 and Examples 5-1 to 5-4, 6-1 to 6-4, 7-1 to 7-4, 8-1 to 8-4, 9-1 to 9-4, 10-1 to 10-4, 11-1 to 11-4, 12-1 to 12-4, 13-1 to 13-4, 14-1 to 14-4, 15-1 to 15-4, 16-1 to 16-4 and 17-1 to 17-4 were measured under the condition of 100 mW/cm$^2$ (AM 1.5), and the results thereof are shown in the following Table 15.

TABLE 15

| | Spin-speed (rpm) | $V_{oc}$ (V) | $J_{sc}$ (mA/cm$^2$) | FF (%) | η (%) | Average η N |
|---|---|---|---|---|---|---|
| Comparative Example 3-1 | 800 | 0.941 | 12.427 | 0.613 | 7.17 | 7.47 |
| | | 0.943 | 13.388 | 0.614 | 7.76 | |
| Comparative Example 3-2 | 1000 | 0.953 | 13.422 | 0.628 | 8.04 | 8.01 |
| | | 0.948 | 13.140 | 0.641 | 7.98 | |
| Comparative Example 3-3 | 1200 | 0.953 | 12.747 | 0.642 | 7.80 | 7.69 |
| | | 0.898 | 12.250 | 0.688 | 7.58 | |
| Comparative Example 3-4 | 1400 | 0.951 | 12.124 | 0.654 | 7.54 | 7.41 |
| | | 0.940 | 11.910 | 0.649 | 7.27 | |
| Example 5-1 | 900 | 0.903 | 15.876 | 0.648 | 9.28 | 9.18 |
| | | 0.901 | 15.765 | 0.639 | 9.08 | |
| Example 5-2 | 1000 | 0.897 | 16.246 | 0.630 | 9.18 | 9.31 |
| | | 0.895 | 16.520 | 0.638 | 9.43 | |
| Example 5-3 | 1100 | 0.902 | 16.189 | 0.662 | 9.67 | 9.56 |
| | | 0.898 | 16.193 | 0.649 | 9.44 | |
| Example 5-4 | 1200 | 0.892 | 15.891 | 0.650 | 9.21 | 9.35 |
| | | 0.891 | 16.078 | 0.663 | 9.49 | |
| Example 6-1 | 800 | 0.896 | 15.976 | 0.651 | 9.32 | 9.32 |
| | | — | — | — | — | |
| Example 6-2 | 1000 | 0.890 | 16.125 | 0.658 | 9.44 | 9.32 |
| | | 0.884 | 16.258 | 0.640 | 9.20 | |
| Example 6-3 | 1200 | 0.890 | 15.849 | 0.655 | 9.23 | 9.07 |
| | | 0.884 | 15.225 | 0.662 | 8.91 | |
| Example 6-4 | 1400 | 0.891 | 14.998 | 0.672 | 8.98 | 8.43 |
| | | 0.872 | 13.914 | 0.649 | 7.88 | |
| Example 7-1 | 800 | 0.910 | 16.294 | 0.638 | 9.46 | 9.54 |
| | | 0.908 | 16.279 | 0.651 | 9.62 | |
| Example 7-2 | 1000 | 0.896 | 16.082 | 0.649 | 9.34 | 9.34 |
| | | — | — | — | — | |
| Example 7-3 | 1200 | 0.906 | 16.134 | 0.649 | 9.49 | 9.49 |
| | | — | — | — | — | |

TABLE 15-continued

| | Spin-speed (rpm) | $V_{oc}$ (V) | $J_{sc}$ (mA/cm$^2$) | FF (%) | η (%) | Average η N |
|---|---|---|---|---|---|---|
| Example 7-4 | 1400 | 0.878 | 15.819 | 0.616 | 8.55 | 8.74 |
| | | 0.878 | 15.998 | 0.636 | 8.93 | |
| Example 8-1 | 900 | 0.778 | 19.044 | 0.546 | 8.08 | 8.08 |
| | | — | — | — | — | |
| Example 8-2 | 1000 | 0.786 | 19.295 | 0.643 | 9.75 | 9.30 |
| | | 0.781 | 18.962 | 0.598 | 8.85 | |
| Example 8-3 | 1200 | 0.794 | 18.833 | 0.638 | 9.54 | 9.47 |
| | | 0.789 | 18.593 | 0.640 | 9.40 | |
| Example 8-4 | 1500 | 0.789 | 18.662 | 0.660 | 9.72 | 9.47 |
| | | 0.781 | 18.439 | 0.640 | 9.22 | |
| Example 9-1 | 900 | 0.784 | 19.355 | 0.607 | 9.20 | 9.09 |
| | | 0.783 | 18.976 | 0.604 | 8.97 | |
| Example 9-2 | 1000 | 0.788 | 19.218 | 0.612 | 9.26 | 9.38 |
| | | 0.783 | 19.438 | 0.624 | 9.50 | |
| Example 9-3 | 1200 | 0.779 | 18.926 | 0.596 | 8.78 | 9.34 |
| | | 0.784 | 19.280 | 0.655 | 9.90 | |
| Example 9-4 | 1500 | 0.776 | 18.641 | 0.635 | 9.19 | 9.39 |
| | | 0.775 | 18.649 | 0.663 | 9.58 | |
| Example 10-1 | 900 | 0.769 | 19.386 | 0.583 | 8.70 | 8.53 |
| | | 0.760 | 19.424 | 0.567 | 8.36 | |
| Example 10-2 | 1000 | 0.773 | 19.192 | 0.617 | 9.16 | 9.20 |
| | | 0.768 | 19.429 | 0.620 | 9.24 | |
| Example 10-3 | 1200 | 0.763 | 18.754 | 0.620 | 8.87 | 8.40 |
| | | 0.751 | 18.869 | 0.560 | 7.93 | |
| Example 10-4 | 1500 | 0.762 | 18.471 | 0.619 | 8.71 | 8.65 |
| | | 0.761 | 18.551 | 0.608 | 8.58 | |
| Example 11-1 | 900 | 0.770 | 19.887 | 0.610 | 9.34 | 9.60 |
| | | 0.768 | 20.060 | 0.640 | 9.86 | |
| Example 11-2 | 1000 | 0.769 | 19.104 | 0.642 | 9.43 | 9.63 |
| | | 0.766 | 19.389 | 0.662 | 9.83 | |
| Example 11-3 | 1200 | 0.771 | 18.935 | 0.659 | 9.62 | 9.47 |
| | | 0.764 | 18.859 | 0.646 | 9.31 | |
| Example 11-4 | 1500 | 0.766 | 18.062 | 0.683 | 9.45 | 9.40 |
| | | 0.763 | 18.600 | 0.659 | 9.34 | |
| Example 12-1 | 900 | 0.920 | 18.173 | 0.601 | 10.05 | 10.05 |
| | | — | — | — | — | |
| Example 12-2 | 1000 | 0.914 | 17.674 | 0.614 | 9.92 | 9.83 |
| | | 0.909 | 17.856 | 0.600 | 9.74 | |
| Example 12-3 | 1200 | — | — | — | — | 10.41 |
| | | 0.930 | 17.694 | 0.633 | 10.41 | |
| Example 12-4 | 1500 | 0.913 | 17.485 | 0.620 | 9.90 | 9.76 |
| | | 0.904 | 17.271 | 0.616 | 9.62 | |
| Example 13-1 | 900 | 0.924 | 18.016 | 0.618 | 10.29 | 10.19 |
| | | 0.922 | 17.784 | 0.615 | 10.08 | |
| Example 13-2 | 1000 | 0.868 | 17.605 | 0.588 | 8.99 | 8.99 |
| | | — | — | — | — | |
| Example 13-3 | 1200 | 0.851 | 18.257 | 0.575 | 8.93 | 8.93 |
| | | — | — | — | — | |
| Example 13-4 | 1500 | 0.926 | 17.557 | 0.629 | 10.22 | 10.18 |
| | | 0.919 | 17.563 | 0.628 | 10.13 | |
| Example 14-1 | 900 | 0.900 | 18.221 | 0.616 | 10.09 | 10.03 |
| | | 0.895 | 17.866 | 0.623 | 9.96 | |
| Example 14-2 | 1000 | 0.908 | 17.777 | 0.627 | 10.12 | 10.11 |
| | | 0.903 | 17.405 | 0.642 | 10.09 | |
| Example 14-3 | 1200 | 0.879 | 17.090 | 0.621 | 9.33 | 9.33 |
| | | — | — | — | — | |
| Example 14-4 | 1500 | 0.910 | 16.689 | 0.655 | 9.95 | 9.95 |
| | | — | — | — | — | |
| Example 15-1 | 900 | 0.894 | 17.816 | 0.626 | 9.98 | 9.93 |
| | | 0.882 | 17.675 | 0.633 | 9.87 | |
| Example 15-2 | 1000 | 0.906 | 17.776 | 0.632 | 10.18 | 10.20 |
| | | 0.901 | 17.634 | 0.643 | 10.21 | |
| Example 15-3 | 1200 | 0.891 | 17.264 | 0.646 | 9.94 | 9.91 |
| | | 0.886 | 17.474 | 0.638 | 9.87 | |
| Example 15-4 | 1500 | 0.913 | 16.946 | 0.650 | 10.06 | 10.05 |
| | | 0.904 | 16.974 | 0.654 | 10.04 | |
| Example 16-1 | 1000 | 0.824 | 16.884 | 0.644 | 8.97 | 8.84 |
| | | 0.823 | 15.880 | 0.666 | 8.70 | |
| Example 16-2 | 1100 | 0.810 | 16.636 | 0.649 | 8.74 | 8.43 |
| | | 0.803 | 16.731 | 0.603 | 8.11 | |
| Example 16-3 | 1200 | 0.825 | 17.252 | 0.625 | 8.90 | 9.14 |
| | | 0.826 | 17.193 | 0.660 | 9.37 | |
| Example 16-4 | 1300 | 0.827 | 14.906 | 0.660 | 8.14 | 8.14 |
| | | — | — | — | — | |
| Example 17-1 | 1000 | 0.823 | 17.250 | 0.653 | 9.27 | 9.45 |
| | | 0.823 | 17.345 | 0.675 | 9.62 | |
| Example 17-2 | 1100 | 0.825 | 16.715 | 0.681 | 9.39 | 9.48 |
| | | 0.822 | 17.113 | 0.681 | 9.57 | |
| Example 17-3 | 1300 | 0.818 | 15.994 | 0.691 | 9.04 | 9.06 |
| | | 0.816 | 16.323 | 0.681 | 9.07 | |
| Example 17-4 | 1500 | 0.825 | 15.365 | 0.684 | 8.67 | 8.74 |
| | | 0.823 | 15.355 | 0.696 | 8.80 | |

In Tables 9 to 15, $V_{oc}$, $J_{sc}$, FF, and PCE(η) mean an open-circuit voltage, a short-circuit current, a fill factor, and energy conversion efficiency, respectively. The open-circuit voltage and the short-circuit current are an X axis intercept and an Y axis intercept, respectively, in the fourth quadrant of the voltage-current density curve, and as the two values are increased, the efficiency of the solar cell is preferably increased. In addition, the fill factor is a value obtained by dividing the area of a rectangle, which may be drawn within the curve, by the product of the short-circuit current and the open-circuit voltage. The energy conversion efficiency may be obtained when these three values are divided by the intensity of the irradiated light, and the higher value is preferred.

Since Compound 1 comprising the thioalkoxy group (Example 5) absorbs light in a longer wavelength region than Comparative Example Compound 2, an organic solar cell, to which Compound 1 was applied, exhibited a high short-circuit current of 15.5 mA/cm$^2$ or more and high photoelectric conversion efficiency of 9% or more.

Since Compound 6 comprising the F (Example 6) absorbs light in a longer wavelength region than Comparative Example Compound 2, an organic solar cell, to which Compound 6 was applied, exhibited a high short-circuit current of 13.9 mA/cm$^2$ or more and high photoelectric conversion efficiency of 8.4% or more.

Since Compound 11 comprising the alkoxy group (Example 7) absorbs light in a longer wavelength region than Comparative Example Compound 2, an organic solar cell, to which Compound 11 was applied, exhibited a high short-circuit current of 15.5 mA/cm$^2$ or more and high photoelectric conversion efficiency of 8.5% or more.

Compounds 16 to 25 used in Examples 8-1 to 8-4, 9-1 to 9-4, 10-1 to 10-4, 11-1 to 11-4, 12-1 to 12-4, 13-1 to 13-4, 14-1 to 14-4, 15-1 to 15-4, 16-1 to 16-4 and 17-1 to 17-4 have a structure comprising a hexyl group at the meta position of Ar1 to Ar4, and the high photoelectric conversion efficiencies thereof are high.

EXPLANATION OF REFERENCE NUMERALS AND SYMBOLS

10: First electrode
20: Second electrode
30: Photoactive layer
100: Organic electronic device

What is claimed is:
1. A heterocyclic compound having a structure of Formula 1:

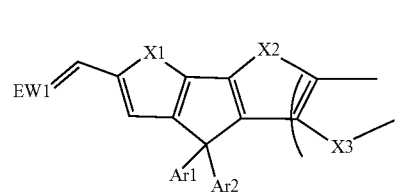

[Formula 1]

-continued

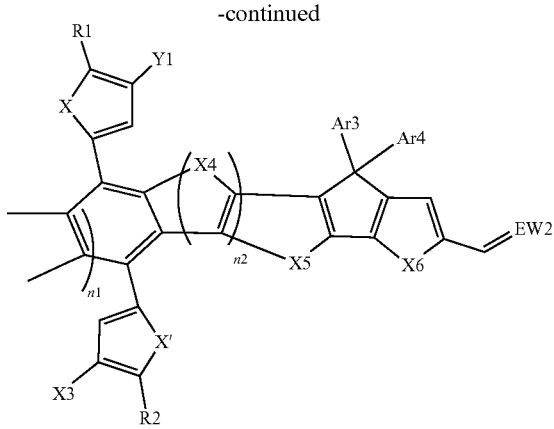

wherein:
X, X' and X1 to X6 are the same as or different from each other, and are each independently O, S, or Se;
R1 and R2 are the same as or different from each other, and are each independently a substituted or unsubstituted straight-chained or branched alkyl group, a substituted or unsubstituted straight-chained or branched alkoxy group, or a substituted or unsubstituted straight-chained or branched thioalkoxy group;
Y1 and Y2 are the same as or different from each other, and are each independently hydrogen, a halogen group, a substituted or unsubstituted straight-chained or branched alkyl group, or a substituted or unsubstituted straight-chained or branched alkoxy group;
EW1 and EW2 are the same as or different from each other, and are each independently a group having a structure of Formula a:

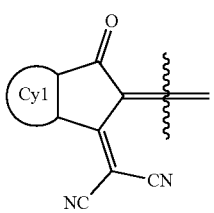

[Formula a]

wherein:
Cy1 is a benzene ring that is unsubstituted or substituted with a halogen group, a straight-chained or branched alkyl group, or a straight-chained or branched alkoxy group, and

is the attachment to Formula 1;
Ar1 to Ar4 are the same as or different from each other, and are each independently a substituted or unsubstituted aryl group or a substituted or unsubstituted heteroaryl group; and
n1 and n2 are each 1.

2. The heterocyclic compound of claim 1, wherein R1 and R2 are the same as or different from each other, and are each independently a branched alkyl group, a branched alkoxy group, or a branched thioalkoxy group.

3. The heterocyclic compound of claim 1, wherein Y1 and Y2 are the same as or different from each other, and are each independently hydrogen or a halogen group.

4. The heterocyclic compound of claim 1, wherein Ar1 to Ar4 are the same as or different from each other, and are each independently an aryl group or a heteroaryl group each of which is unsubstituted or substituted with a straight-chained or branched alkyl group, a straight-chained or branched alkoxy group, or a straight-chained or branched thioalkoxy group.

5. The heterocyclic compound of claim 1, wherein Ar1 to Ar4 are the same as or different from each other, and are each independently any one selected from the following structures:

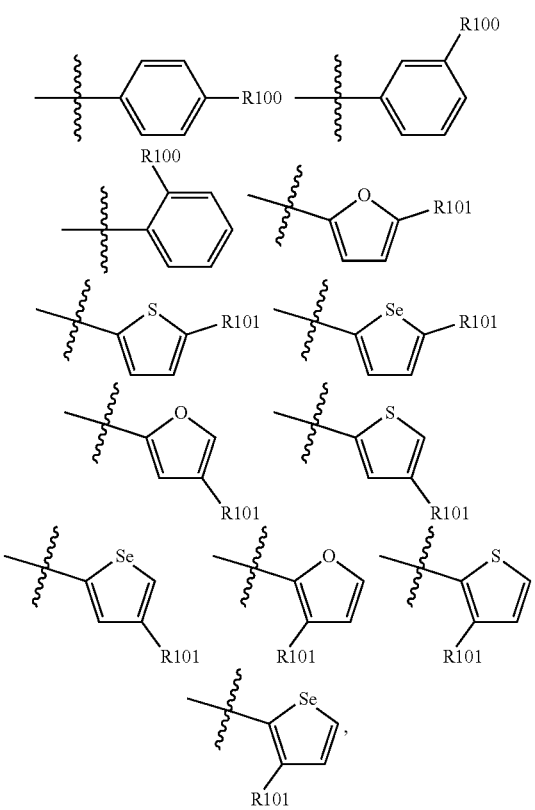

wherein:
R100 and R101 are the same as or different from each other, and are each independently a straight-chained or branched alkyl group, a straight-chained or branched alkoxy group, or a straight-chained or branched thioalkoxy group, and

is the attachment to Formula 1.

6. The heterocyclic compound of claim 1, wherein Formula 1 is a compound of Formula 1-2:

[Formula 1-2]

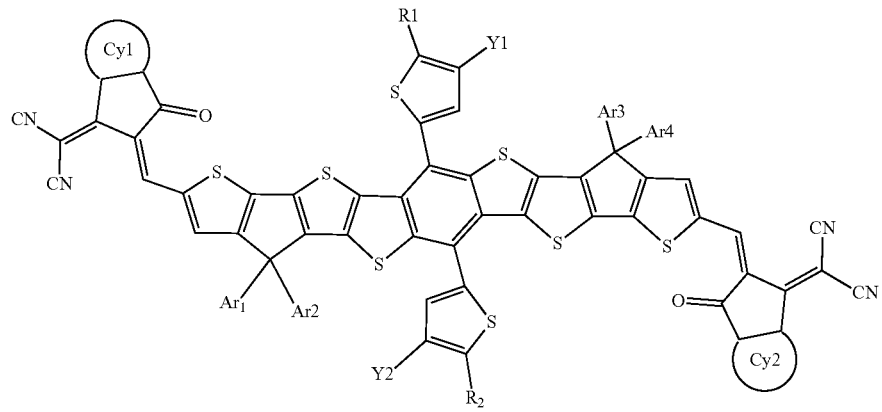

wherein:
the definitions of R1, R2, Y1, Y2, and Ar1 to Ar4 are the same as those defined in Formula 1; and
Cy1 and Cy2 are the same as or different from each other, and are each independently a benzene ring that is unsubstituted or substituted with a halogen group, a straight-chained or branched alkyl group, or a straight-chained or branched alkoxy group.

7. The heterocyclic compound of claim 1, wherein Formula 1 is a compound of any one of the following Formulae 2-4 to 2-6:

[Formula 2-4]

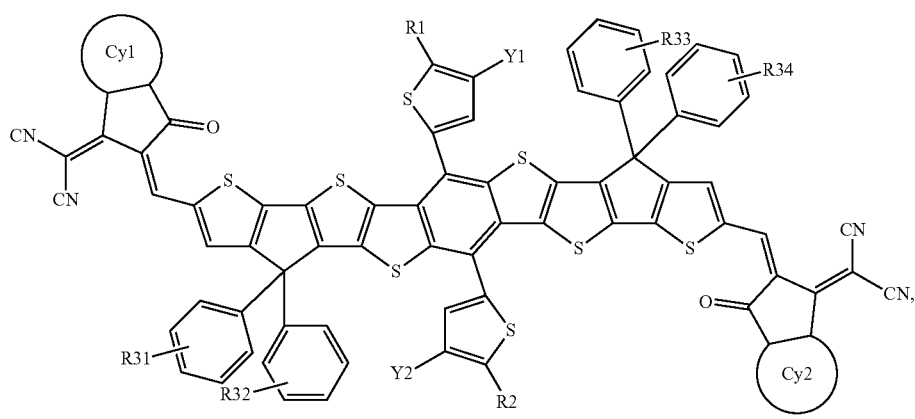

[Formula 2-5]

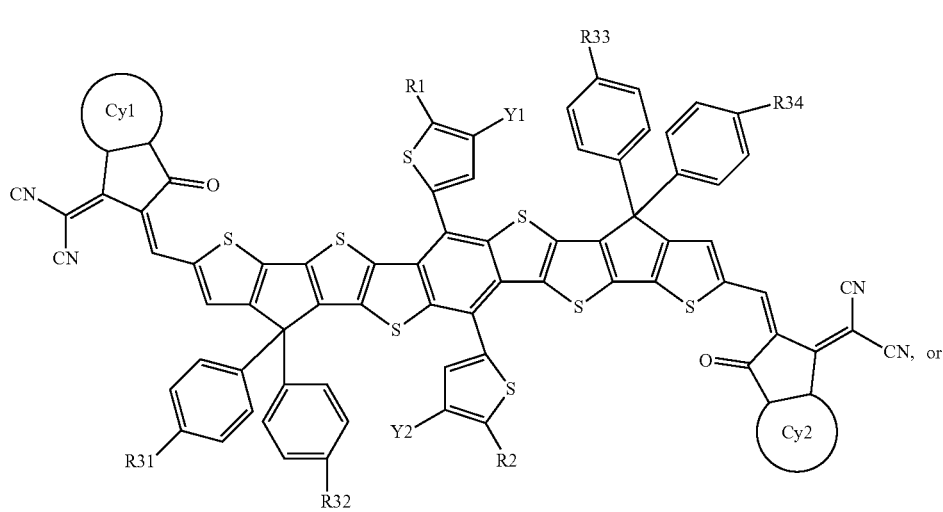

-continued

[Formula 2-6]

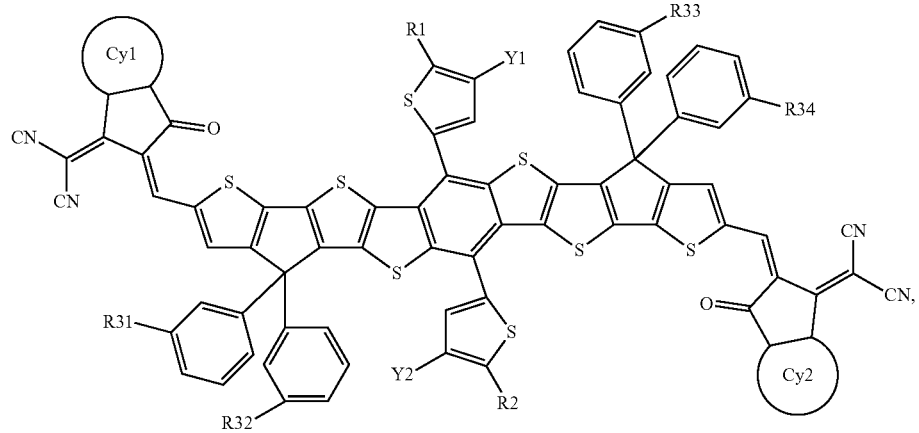

wherein:
the definitions of R1, R2, Y1, and Y2 are the same as those defined in Formula 1;
R31 to R34 are the same as or different from each other, and are each independently a straight-chained or branched alkyl group, a straight-chained or branched alkoxy group, or a straight-chained or branched thioalkoxy group; and
Cy1 and Cy2 are the same as or different from each other, and are each independently a benzene ring that is unsubstituted or substituted with a halogen group, a straight-chained or branched alkyl group, or a straight-chained or branched alkoxy group.

8. A composition for an organic electronic device, the composition comprising the heterocyclic compound of claim 1.

9. The composition of claim 8, comprising an electron donor material and an electron acceptor material, and the electron acceptor material comprises the heterocyclic compound.

10. The composition of claim 9, wherein the electron donor material and the electron acceptor material constitute a bulk heterojunction (BHJ).

11. An organic electronic device comprising:
a first electrode;
a second electrode facing the first electrode; and
an organic material layer comprising one or more layers between the first electrode and the second electrode,
wherein the one or more layers of the organic material layer comprise the composition for the organic electronic device of claim 8.

12. The organic electronic device of claim 11, wherein the organic electronic device is selected from the group consisting of an organic photoelectric device, an organic transistor, an organic solar cell, and an organic light emitting device.

13. The organic electronic device of claim 11, wherein the organic electronic device is an organic solar cell.

14. The organic electronic device of claim 13, wherein the organic material layer comprises a photoactive layer, and the photoactive layer comprises the composition for the organic electronic device.

* * * * *